United States Patent
Gao et al.

(10) Patent No.: US 11,751,474 B2
(45) Date of Patent: Sep. 5, 2023

(54) COMPOUND AND ORGANIC LIGHT EMITTING DISPLAY DEVICE

(71) Applicant: Shanghai Tianma AM-OLED Co., Ltd., Shanghai (CN)

(72) Inventors: Wei Gao, Shanghai (CN); Ying Liu, Shanghai (CN); Lei Zhang, Shanghai (CN); Wenpeng Dai, Shanghai (CN); Jinghua Niu, Shanghai (CN); Gaojun Huang, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 1009 days.

(21) Appl. No.: 16/590,297

(22) Filed: Oct. 1, 2019

(65) Prior Publication Data

US 2020/0411769 A1     Dec. 31, 2020

(30) Foreign Application Priority Data

Jun. 29, 2019   (CN) .......... 201910580662.3

(51) Int. Cl.

| | | |
|---|---|---|
| H01L 51/54 | (2006.01) | |
| H10K 85/60 | (2023.01) | |
| C07D 209/86 | (2006.01) | |
| C07D 401/14 | (2006.01) | |
| C07D 403/14 | (2006.01) | |
| C07D 409/14 | (2006.01) | |
| C07F 5/02 | (2006.01) | |
| C07F 9/572 | (2006.01) | |
| H10K 85/30 | (2023.01) | |
| H10K 50/11 | (2023.01) | |
| H10K 101/10 | (2023.01) | |
| H10K 101/30 | (2023.01) | |

(52) U.S. Cl.
CPC ....... *H10K 85/6572* (2023.02); *C07D 209/86* (2013.01); *C07D 401/14* (2013.01); *C07D 403/14* (2013.01); *C07D 409/14* (2013.01); *C07F 5/027* (2013.01); *C07F 9/5728* (2013.01); *H10K 85/322* (2023.02); *H10K 85/654* (2023.02); *H10K 85/6576* (2023.02); *H10K 50/11* (2023.02); *H10K 2101/10* (2023.02); *H10K 2101/30* (2023.02)

(58) Field of Classification Search
None
See application file for complete search history.

(56) References Cited

FOREIGN PATENT DOCUMENTS

| | | |
|---|---|---|
| CN | 104277824 A | 1/2015 |
| CN | 106104838 A | 11/2016 |
| CN | 109134882 A | 1/2019 |
| CN | 109897055 A | 6/2019 |
| JP | 6313048 A | 1/1988 |
| JP | 2005011732 A | 1/2005 |
| KR | 20160117823 A | 10/2016 |

OTHER PUBLICATIONS

Palash Pandit et al; "Acid/base-regulated reversible electron transfer disproportionation of N-N linked bicarbazole and biacridine derivativest"; Chem. Sci., 2015, 6, 4160.

Brandon R Rosen et al; "Total Synthesis of Dixiamycin B by Electrochemical Oxidation"; J. Am. Chem. Soc 2014, 136, 5571-5574.

Xiang-Yang Liu et al; "9,9'-Bicarbazole: New Molecular Skeleton for Organic Light-Emitting Diodes"; Chemistry: A European Journal; DOI: 10.1002/chem.201806314; Jan. 26, 2019.

*Primary Examiner* — Andrew K Bohaty
(74) *Attorney, Agent, or Firm* — KILPATRICK TOWNSEND & STOCKTON LLP

(57) ABSTRACT

The present disclosure relates to the field of organic electroluminescence materials and particularly relates to a compound and an organic light emitting display device. The compound has a structure represented by Formula (I):

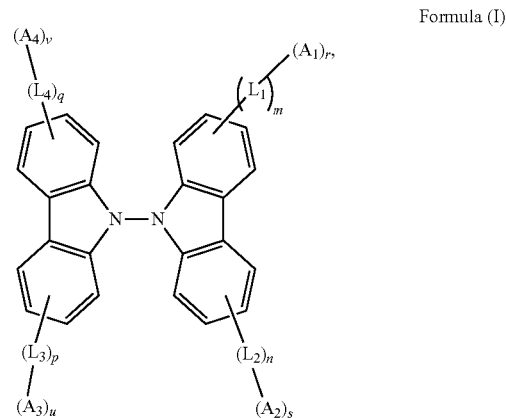

Formula (I)

and, m, n, p, q, r, s, u, and v are each independently selected from 0 or 1, at least one of r and s is 1, at least one of u and v is 1, $L_1$, $L_2$, $L_3$, and $L_4$ are each independently selected from substituted or unsubstituted C6-C40 aryl, or substituted or unsubstituted C3-C40 heterocyclyl, and $A_1$, $A_2$, $A_3$, and $A_4$ each are independently selected from an electron acceptor unit.

20 Claims, 1 Drawing Sheet

COMPOUND AND ORGANIC LIGHT EMITTING DISPLAY DEVICE

CROSS-REFERENCE TO RELATED APPLICATION

This disclosure claims the benefit and priority of Chinese Patent Application No. 201910580662.3, filed on Jun. 29, 2019. The entire disclosure of the above application is incorporated herein by reference.

FIELD

The present disclosure relates to the field of organic electroluminescence materials and particularly relates to a compound and an organic light emitting display device.

BACKGROUND

In accordance with a light emitting mechanism, materials can be used in OLED luminescent layers mainly comprise the following four kinds: fluorescent materials, phosphorescence materials, triplet-triplet annihilation (TTA) materials and thermally activated delayed fluorescence (TADF) materials. The theoretical maximum internal quantum yield of the fluorescent materials does not exceed 25%, and the theoretical maximum internal quantum yield of the TTA materials does not exceed 62.5%, and the theoretical maximum internal quantum yield of the phosphorescence materials and the theoretical maximum internal quantum yield of the TADF materials can both reach 100%.

SUMMARY

The present disclosure provides a compound and an organic light emitting display device.

According to one embodiment of the present disclosure, a compound is provided, and the compound has a structure represented by Formula I:

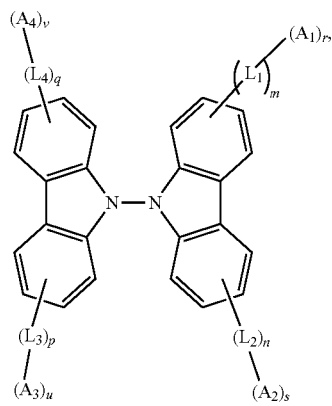

Formula (I)

and, m, n, p, q, r, s, u, and v are each independently selected from 0 or 1, at least one of r and s is 1, at least one of u and v is 1, $L_1$, $L_2$, $L_3$, and $L_4$ are each independently selected from substituted or unsubstituted C6-C40 aryl, or substituted or unsubstituted C3-C40 heterocyclyl, and $A_1$, $A_2$, $A_3$, and $A_4$ are each independently selected from an electron acceptor unit.

According to another embodiment of the present disclosure, an organic light emitting display device is provided, and the device includes an organic electroluminescence apparatus, and the organic electroluminescence apparatus includes:

an organic functional layer including one or more organic film layers, and at least one of the organic film layers serves as a luminescent layer; and the luminescent layer includes a luminescent material, and the luminescent material includes any one or more of the compounds provided by the present disclosure.

DETAILED DESCRIPTION OF THE EMBODIMENTS

Figure 1:
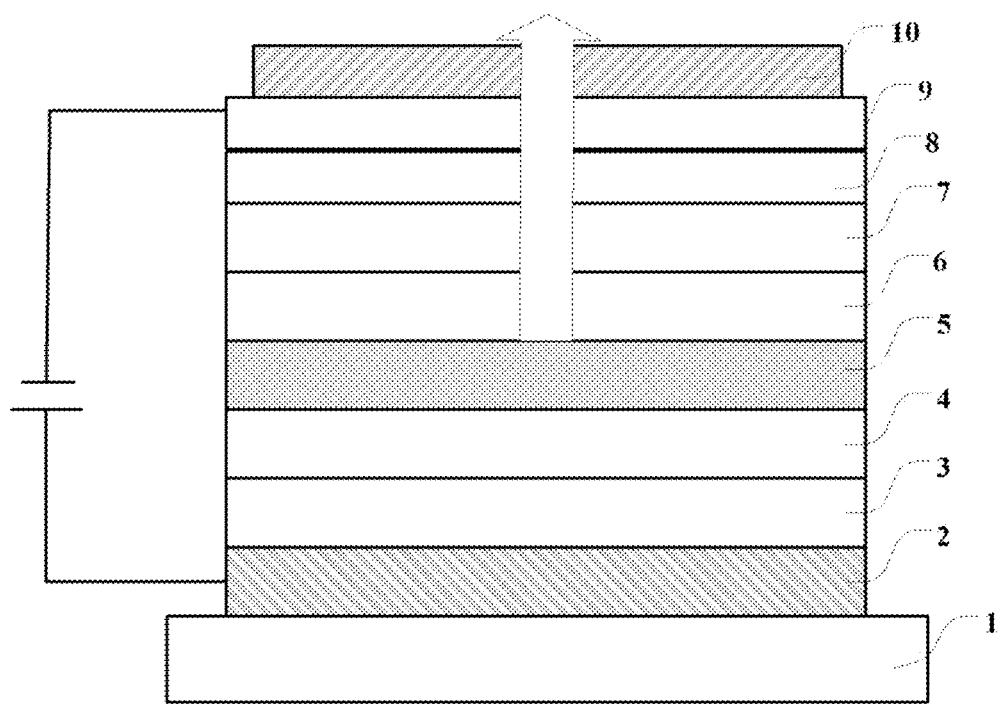
FIG. 1 is a structural schematic diagram of an organic electroluminescence apparatus of the present disclosure.

Some embodiments are only intended to describe the present disclosure, rather than limit contents of the present disclosure, and the present disclosure will be further described and represented below with reference to the embodiments.

The present disclosure provides a compound and an organic light emitting display device.

According to one embodiment of the present disclosure, a compound is provided, and the compound has a structure represented by Formula (I):

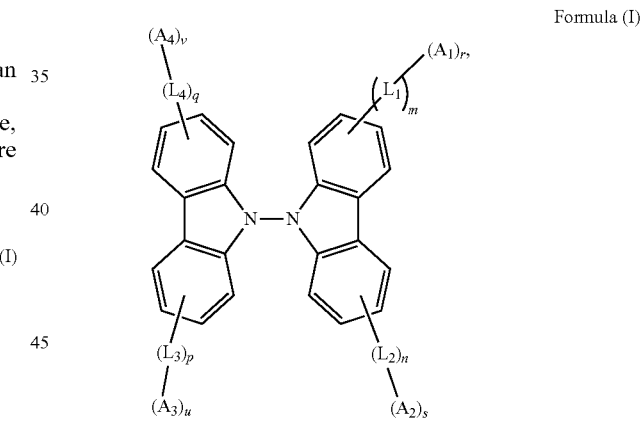

Formula (I)

and, m, n, p, q, r, s, u, and v are each independently selected from 0 or 1, at least one of r and s is 1, at least one of u and v is 1, $L_1$, $L_2$, $L_3$, and $L_4$ are each independently selected from substituted or unsubstituted C6-C40 aryl, or substituted or unsubstituted C3-C40 heterocyclyl, and $A_1$, $A_2$, $A_3$, and $A_4$ are each independently selected from an electron acceptor unit.

Carbazole groups have the following advantages: (1) raw materials are cheap, and the cost is low; (2) the modification of molecule property is easy to perform on the basis of not changing main skeleton structures of molecules; (3) a nitrogen atom is liable to perform functional modification; (4) the carbazole groups have a plurality of connection positions and can be connected with other molecular structures; (5) the thermal stability and chemical stability are good; (6) the triplet energy level is high; and (7) the electron donating capability and light emitting property are excellent, and the hole transport characteristic is excellent.

In the present disclosure, a bicarbazole group is used as an electron donating unit, two carbazole groups are connected in a manner that a N atom and a N atom on carbazoles are connected directly, a bigger dihedral angle is formed between the two carbazole units, the degree of conjugation between the two carbazole groups is reduced, the triplet energy level of a material is effectively increased, and a host material having high triplet energy level is obtained. Meanwhile, the bicarbazole group has more modifiable chemical sites, and other electron acceptor groups can be introduced to bicarbazole through chemical reactions to obtain the bipolar host material.

According to one embodiment of the present disclosure, $L_1$ and $L_3$ are identical.

According to one embodiment of the present disclosure, $L_2$ and $L_4$ are identical.

When $L_1$ and $L_3$ are identical and $L_2$ and $L_4$ are identical, the synthesis is simpler, and the synthesis cost can be effectively reduced.

According to one embodiment of the present disclosure, $A_1$ and $A_3$ are identical.

According to one embodiment of the present disclosure, $A_2$ and $A_4$ are identical.

When $A_1$ and $A_3$ are identical and $A_2$ and $A_4$ are identical, asymmetric structure can be formed, a bigger dihedral angle is formed between bicarbazoles, two D-A structures are formed on the same molecule, and a more sufficient energy transfer process with the guest luminescent material can be generated.

According to one embodiment of the present disclosure, r and u are selected from 1, and s and v are selected from 0. In this way, it can be ensured that two D-A structures interact in the same molecule, meanwhile, the molecular weight is lower, the material is appropriate for evaporation, the evaporating temperature is relatively low, and the energy consumption of evaporation equipment is reduced.

According to one embodiment of the present disclosure, r, s, u, and v are all selected from 1. In this way, the molecular weight is higher, the material is higher in glass transition temperature, and an organic film formed has higher morphology stability. Meanwhile, such material is more appropriate for being processed by solution-method to produce a large-size panel.

Electrical properties of an entire molecule can be adjusted through matching species and quantities of $A_1$, $A_2$, $A_3$, and $A_4$ to obtain various material systems with required electrical properties.

According to one embodiment of the present disclosure, the C6-C40 aryl is selected from one or more of phenyl, biphenyl, terphenyl, naphthyl, binaphthyl, anthryl, bianthryl, diphenylanthryl, benzodihydroanthryl, phenanthryl, dihydrophenanthryl, triphenylene, pyrenyl, fluorenyl, difluorenyl, fluoranthenyl, indenofluorenyl, cyclopentanophenanthryl, spirofluorenyl, benzofluorenyl, indenoanthryl, dibenzofluorenyl, naphthoanthryl, and benzoanthryl.

According to one embodiment of the present disclosure, the C3-C40 heterocyclyl is selected from one or more of thienyl, thiazolyl, pyridyl, furyl, pyranyl, pyrrolyl, pyrazolyl, imidazolyl, oxazolyl, oxadiazolyl, triazolyl, thiadiazolyl, pyridazinyl, pyrimidinyl, pyrazinyl, triazinyl, benzofuranyl, dibenzofuranyl, benzothienyl, dibenzothienyl, phenoxazinyl, phenazinyl, phenothiazinyl, thiaoxazinyl, thianthryl, indolyl, benzimidazolyl, benzothiazolyl, purinyl, quinolyl, isoquinolyl, quinoxalyl, and phenanthrolinyl.

According to the present disclosure, substituents in the "substituted . . . " may be any one or more of C1-C10 alkyl or cycloalkyl, C2-C10 alkenyl, C1-C6 alkoxy, C6-C30 monocyclic aromatic hydrocarbon or fused-ring aromatic hydrocarbon groups, and C3-C30 monocyclic hetero-aromatic hydrocarbon or fused-ring hetero-aromatic hydrocarbon groups.

According to one embodiment of the present disclosure, $A_1$, $A_2$, $A_3$, and $A_4$ are each independently selected from any one or more of a nitrogen-containing heterocyclic substituent, a cyano substituent, a triaryl boron substituent, a benzophenone substituent, an aromatic heterocyclic ketone substituent, and a sulfone substituent.

According to one embodiment of the present disclosure, the nitrogen-containing heterocyclic substituent is selected from any one or more of the structures below:

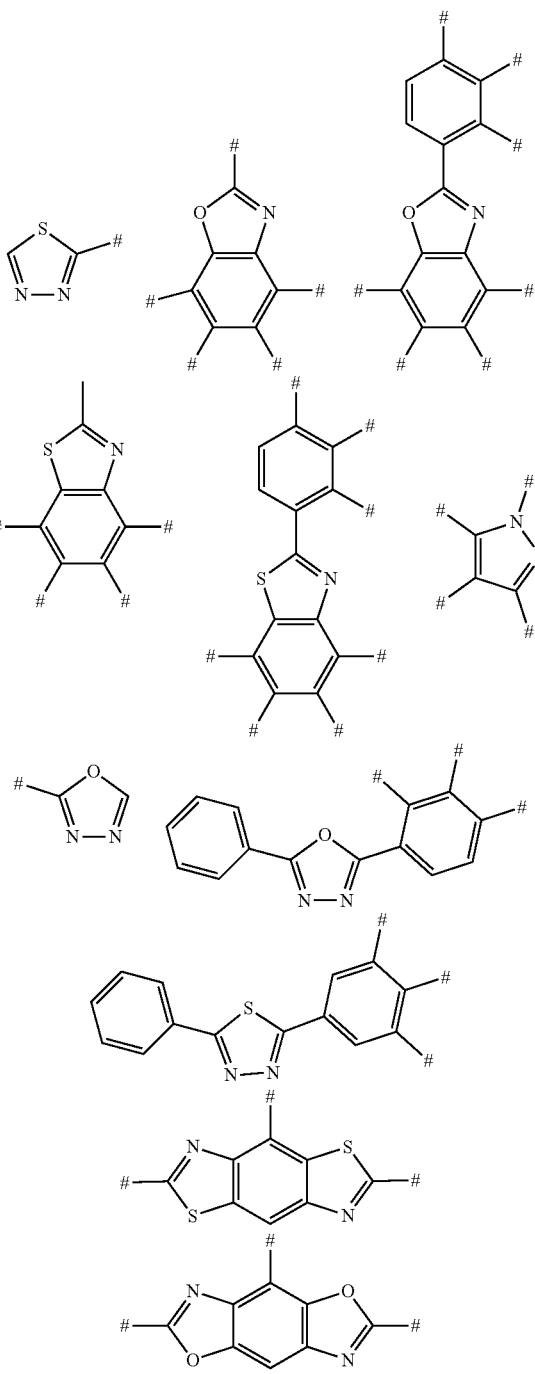

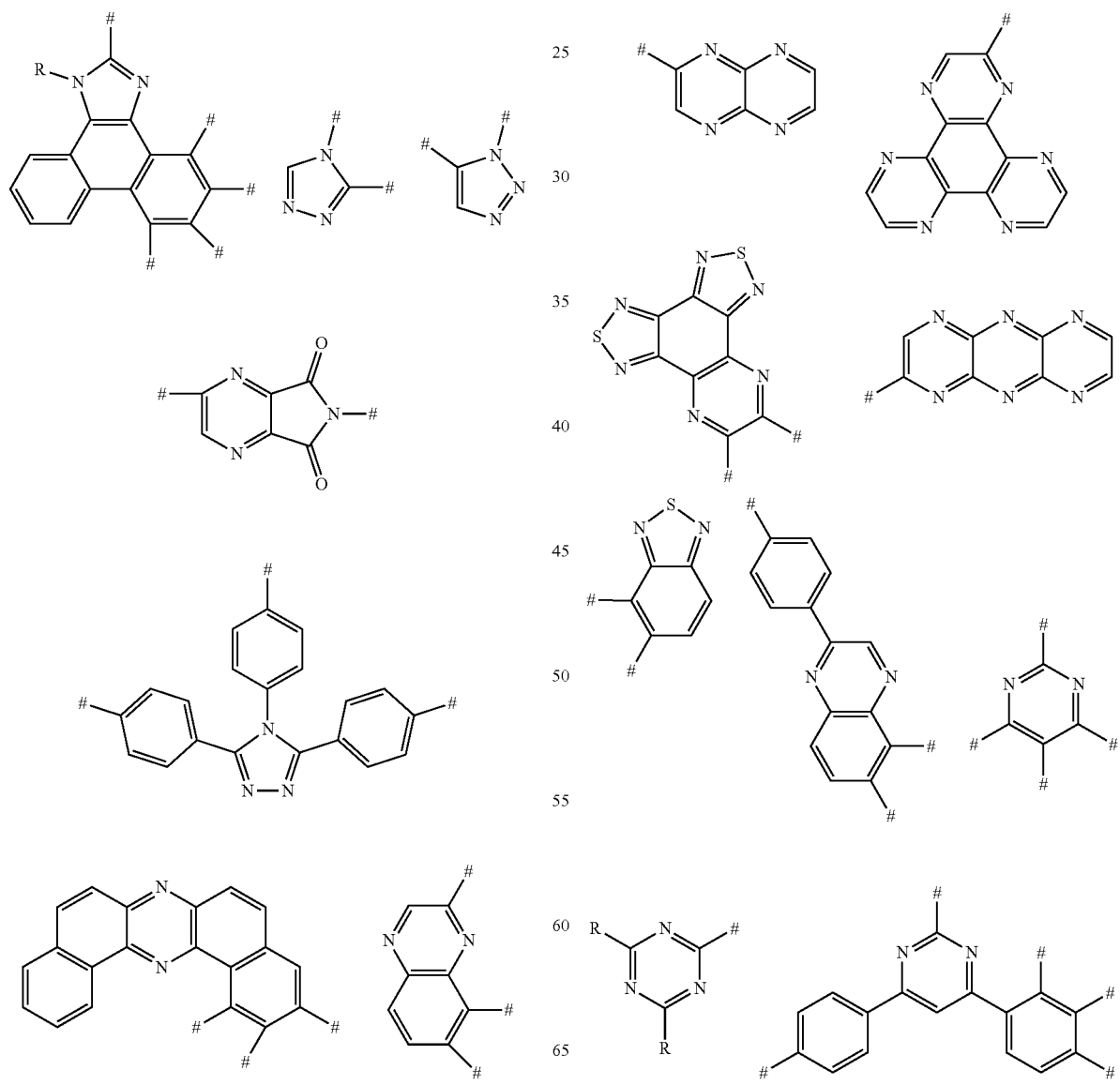

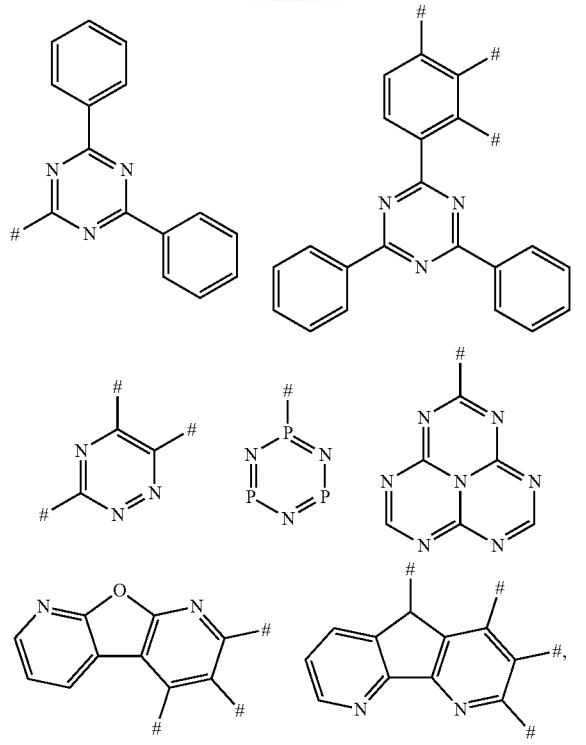

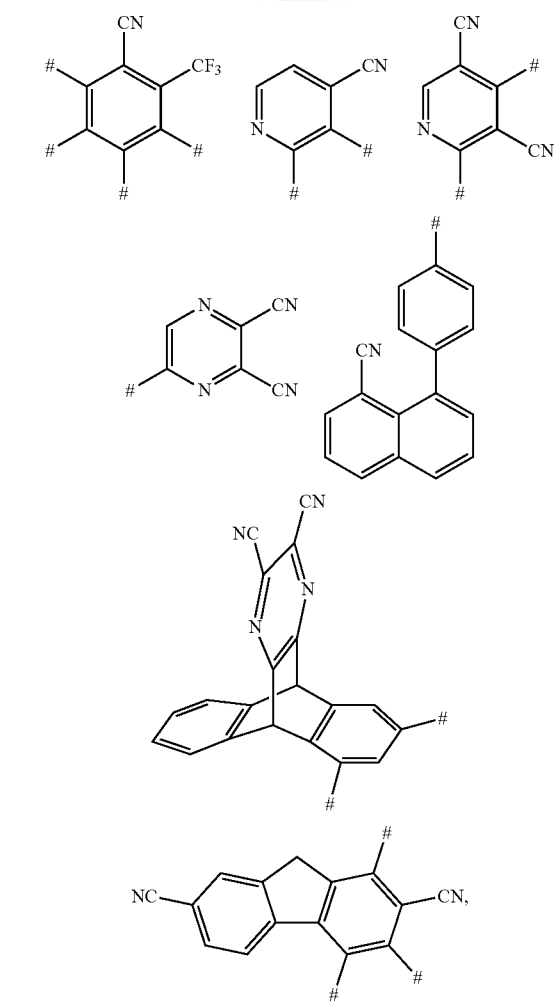

and, # represents a connection position; and R is selected from a hydrogen atom, C1-20 alkyl, C1-20 alkoxy, C4-8 cycloalkyl, C6-40 aryl, and C4-40 heteroaryl.

According to one embodiment of the present disclosure, the cyano substituent is selected from one or more of the structures below:

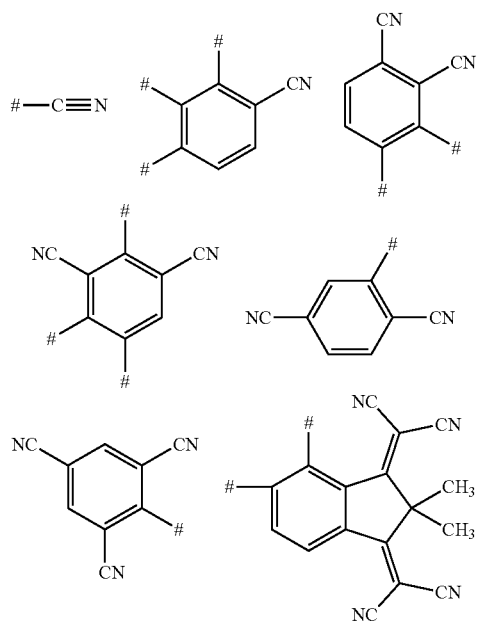

and, # represents a connection position.

The cyano substituent has very high electro-withdrawing ability, non-radiative transition can be effectively inhibited, the radiative transition rate constant kr is effectively increased, and the luminous efficiency is increased.

According to one embodiment of the present disclosure, the aryl boron substituent is selected from one or more of the structures below:

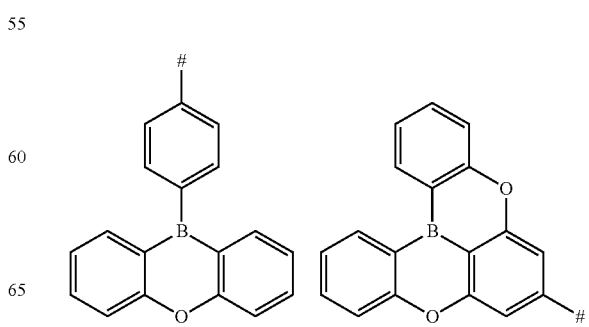

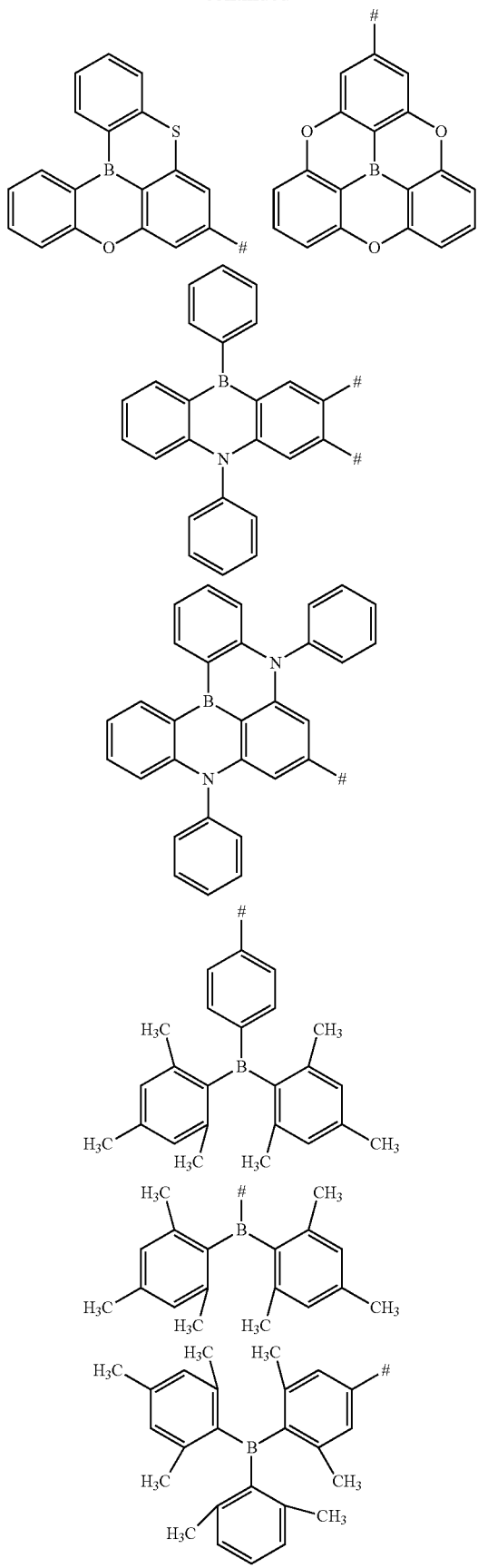

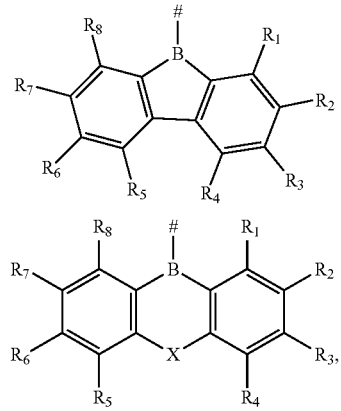

and, # represents a connection position; X is selected from $BR_9$, O, S, or $NR_9$; and $R_1$-$R_9$ are each independently selected from C1-20 alkyl, C1-20 alkoxy, C6-40 aryl, and C4-40 heteroaryl.

A boron atom has an empty p orbit, when an aromatic ring is connected to the boron atom, a conjugate plane can be provided, a substituent on the aromatic ring can protect the boron atom from destruction caused by oxygen gas and water, the entire molecule can have better optical properties and can be used for synthesizing triaryl derivatives, and the obtained triaryl boron substituents can be used for constructing a D-A type bipolar host material.

According to one embodiment of the present disclosure, the aryl ketone substituent and the aromatic heterocyclic ketone substituent are selected from one or more of the structures below:

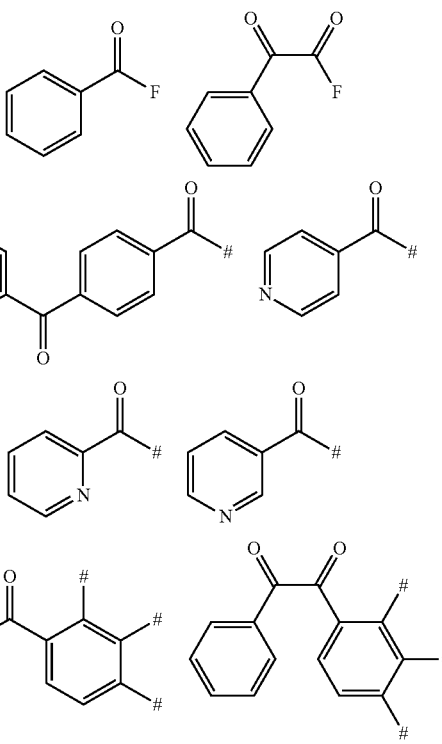

-continued

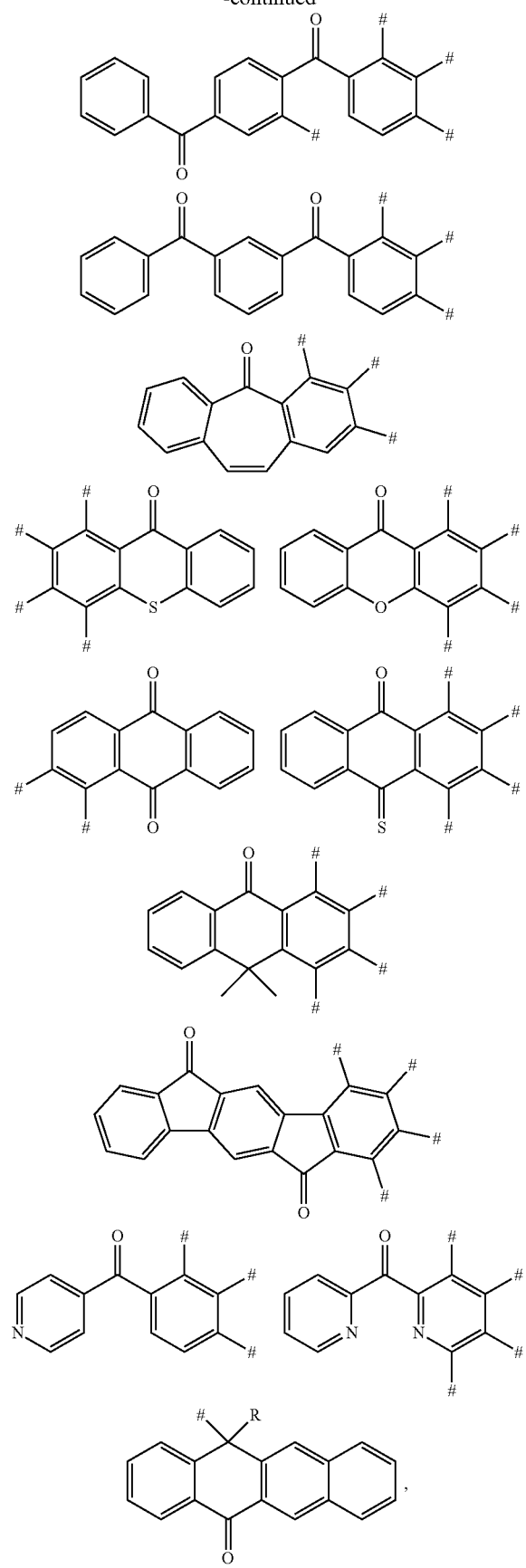

and, # represents a connection position, and R in the structural formula represents C1-20 alkyl, C1-20 alkoxy, C2-20 alkenyl, C2-20 alkynyl, C4-8 cycloalkyl, C6-40 aryl, and C4-40 heteroaryl.

The benzophenone substituent contains an electron-deficient carbonyl group (C=O), the carbonyl group has a bigger torsion angle with a benzene ring when the benzophenone substituent serves as an electron acceptor, the benzophenone substituent is a very efficient organic functional group ($kISC=10^{11}$ $s^{-1}$) for intersystem crossing, and thus, and is very suitable for being matched with an electron donating group as the electron acceptor to construct a D-A type bipolar host material.

According to one embodiment of the present disclosure, the sulfone substituent is selected from one or more of the structures below:

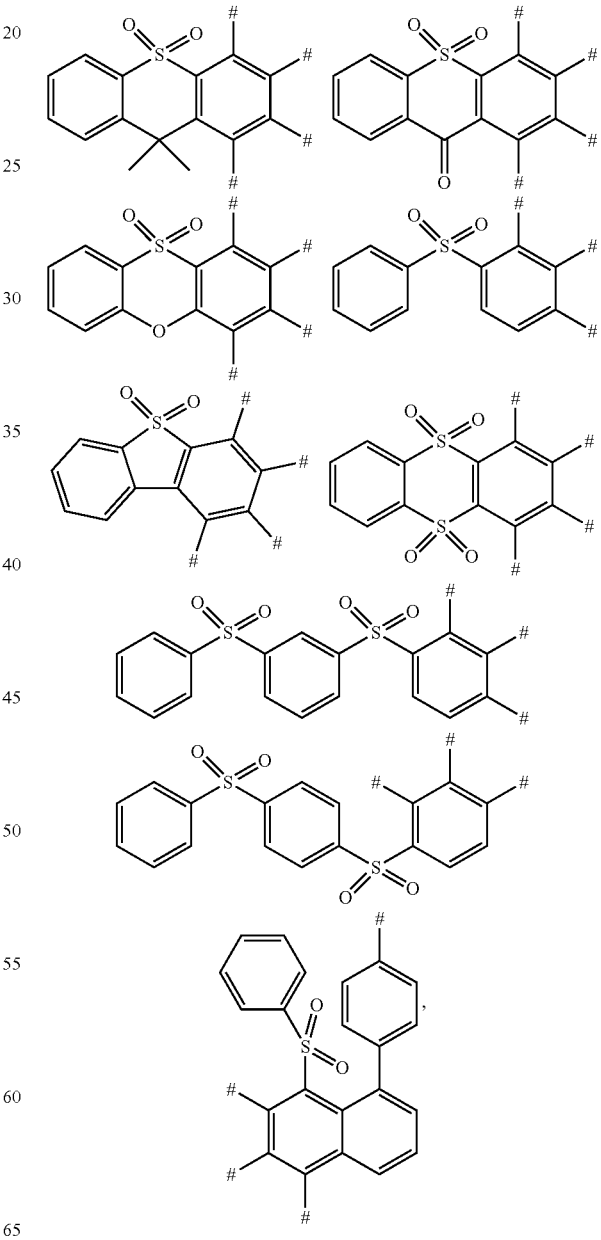

and, # represents a connection position.

The sulfone substituent has good electro-withdrawing ability as an electron acceptor, a certain torsion angle is present in the center of the molecule, a photophysical process of intersystem crossing between a singlet state and a triplet state can be improved, the sulfone substituent can be used for constructing a D-A type TADF molecule as an electron acceptor, and an excellent energy transfer process is formed between the D-A type TADF molecule and a luminescent guest molecule.

According to one embodiment of the present disclosure, $A_1, A_2, A_3$, and $A_4$ are each independently selected from one or more of the structures below:

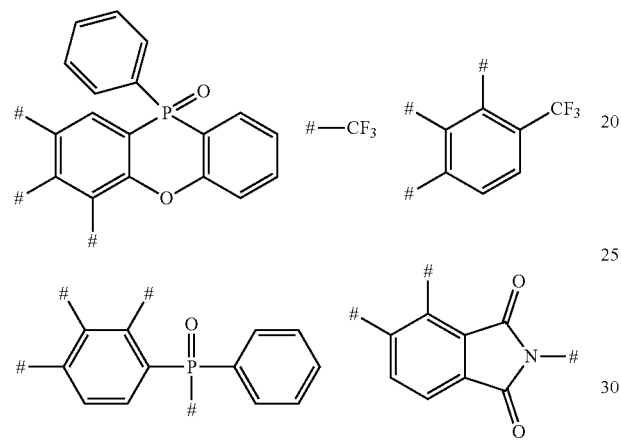

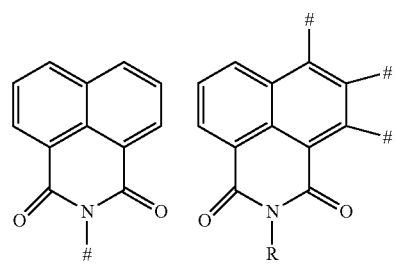

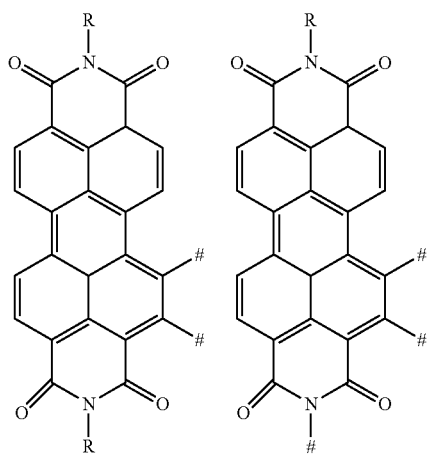

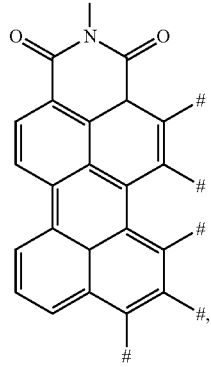

-continued and, # represents a connection position, and R in each structural formula each independently represents C1-20 alkyl, C1-20 alkoxy, C2-20 alkenyl, C2-20 alkynyl, C4-8 cycloalkyl, C6-40 aryl, and C4-40 heteroaryl.

According to one embodiment of the present disclosure, r and u are selected from 1, s and v are selected from 0, and the C6-C40 aryl is selected from one or more of phenyl, biphenyl, terphenyl, naphthyl, binaphthyl, anthryl, bianthryl, diphenylanthryl, benzodihydroanthryl, phenanthryl, dihydrophenanthryl, triphenylene, pyrenyl, fluorenyl, difluorenyl, fluoranthenyl, indenofluorenyl, cyclopentanophenanthryl, spirofluorenyl, benzofluorenyl, indenoanthryl, dibenzofluorenyl, naphthoanthryl, and benzoanthryl; and the C3-C40 heterocyclyl is selected from one or more of thienyl, thiazolyl, pyridyl, furyl, pyranyl, pyrrolyl, pyrazolyl, imidazolyl, oxazolyl, oxadiazolyl, triazolyl, thiadiazolyl, pyridazinyl, pyrimidinyl, pyrazinyl, triazinyl, benzofuranyl, dibenzofuranyl, benzothienyl, dibenzothienyl, phenoxazinyl, phenazinyl, phenothiazinyl, thiaoxazinyl, thiaanthryl, indolyl, benzimidazolyl, benzothiazolyl, purinyl, quinolyl, isoquinolyl, quinoxalyl, and phenanthrolinyl.

According to one embodiment of the present disclosure, r and u are selected from 1, s and v are selected from 0, and $A_1, A_2, A_3$, and $A_4$ are each independently selected from one or more of the structures below:

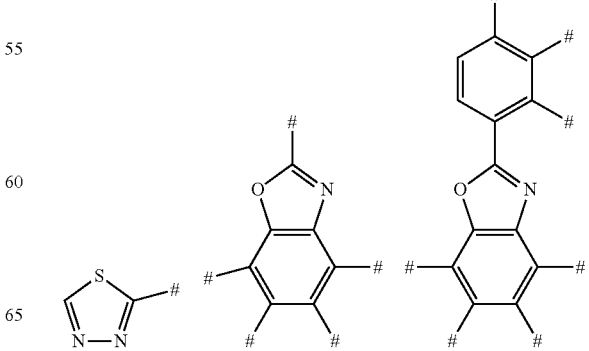

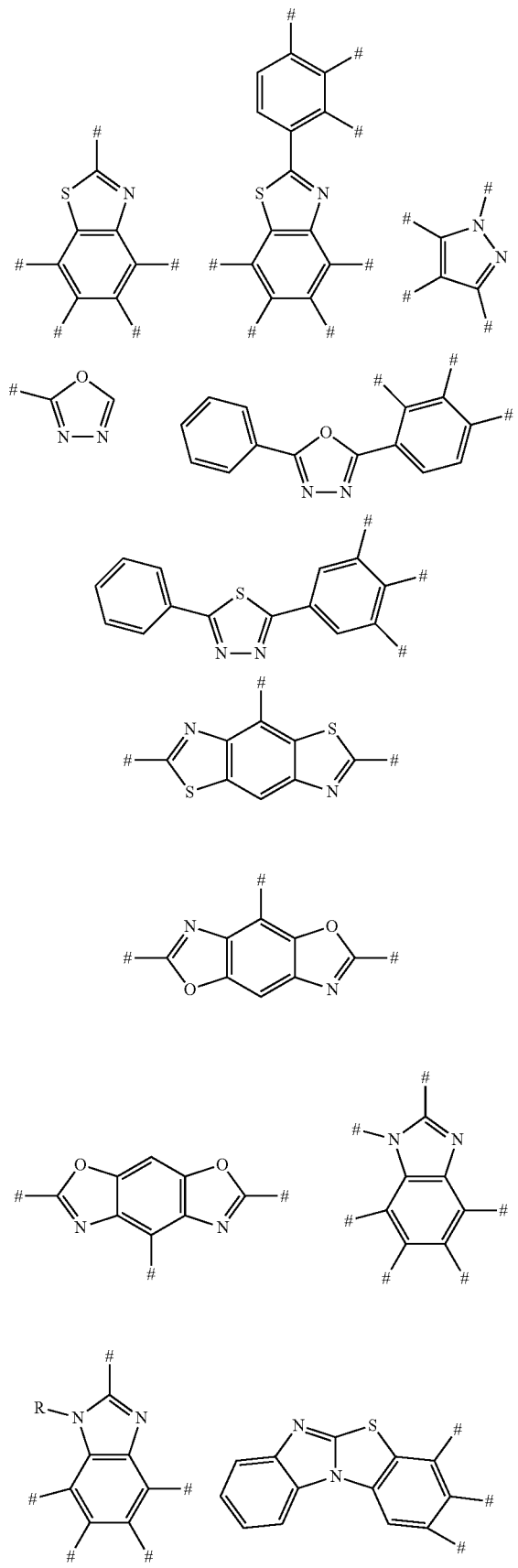
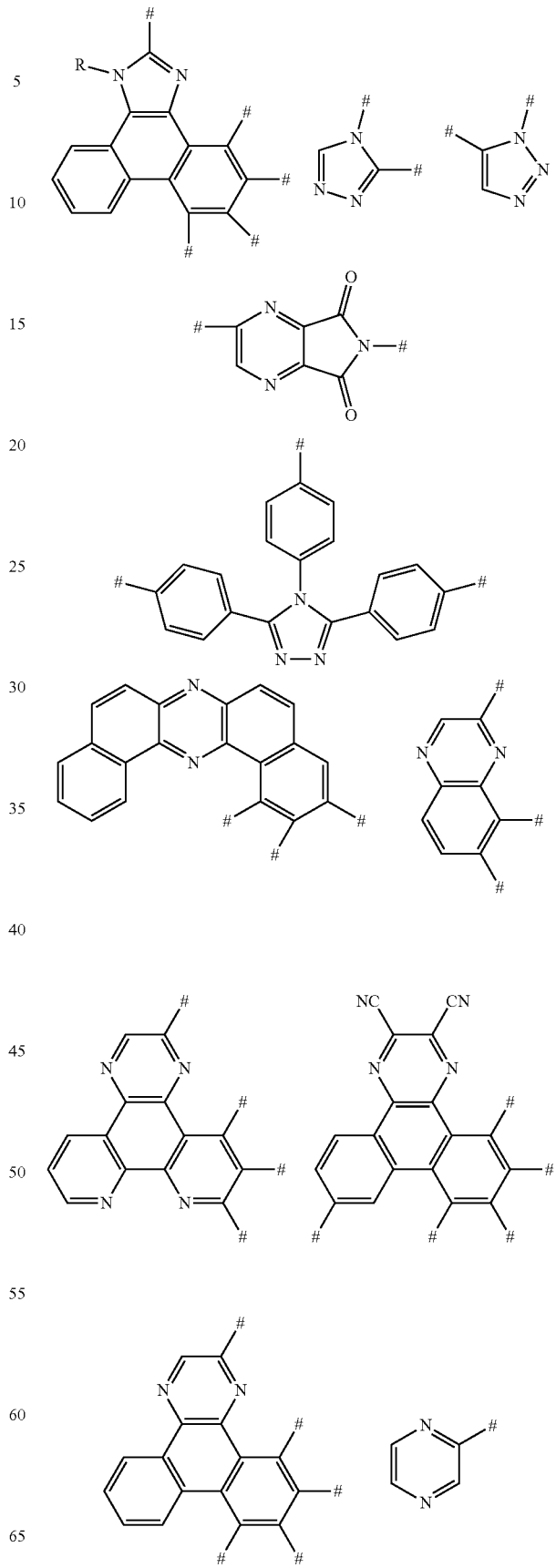

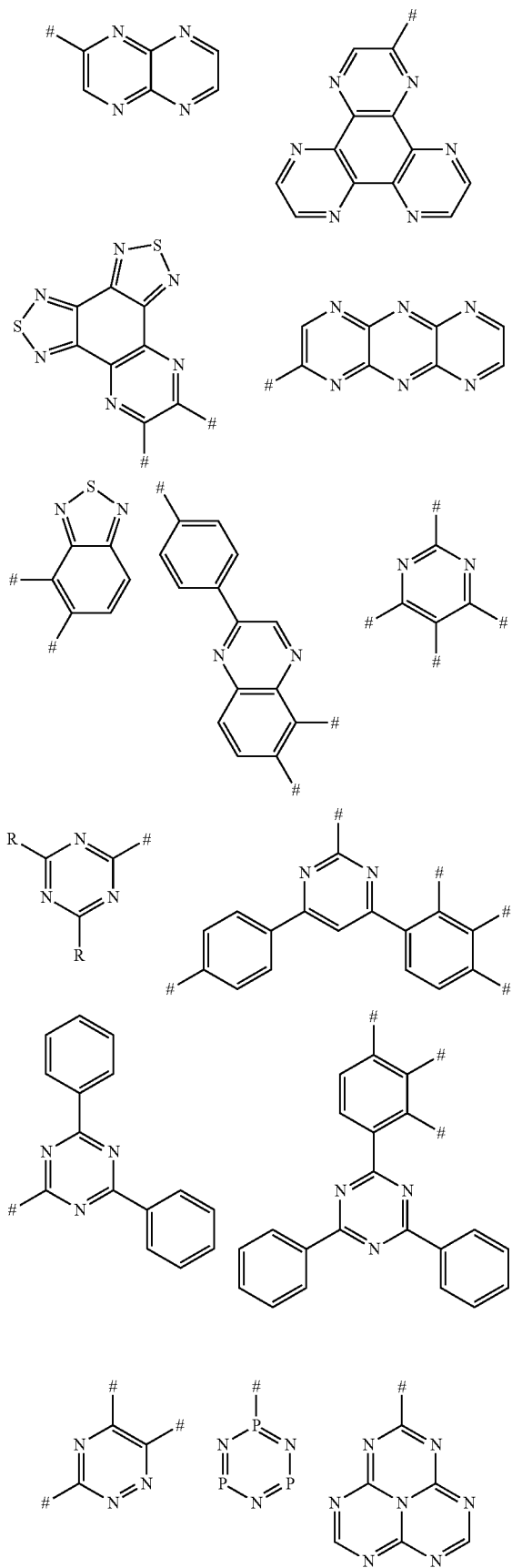
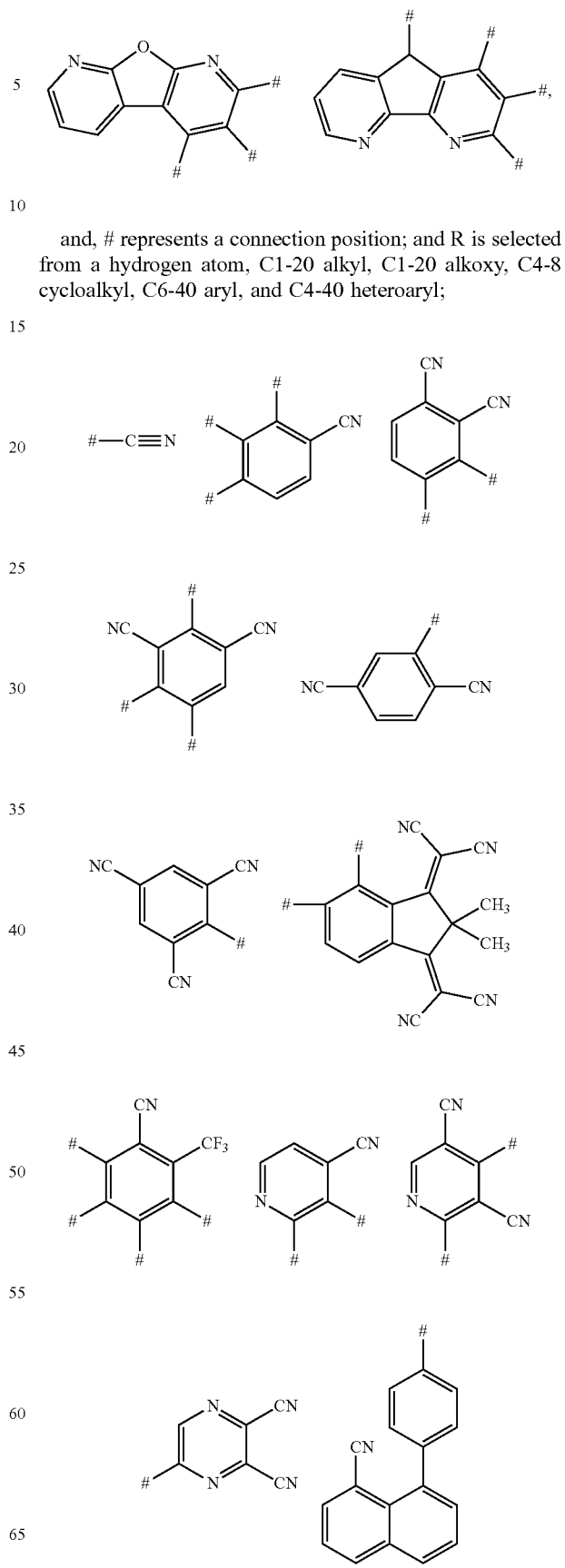
and, # represents a connection position; and R is selected from a hydrogen atom, C1-20 alkyl, C1-20 alkoxy, C4-8 cycloalkyl, C6-40 aryl, and C4-40 heteroaryl;

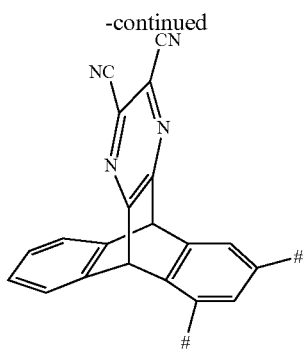
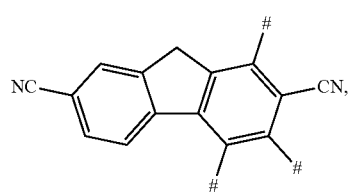
and, # represents a connection position;
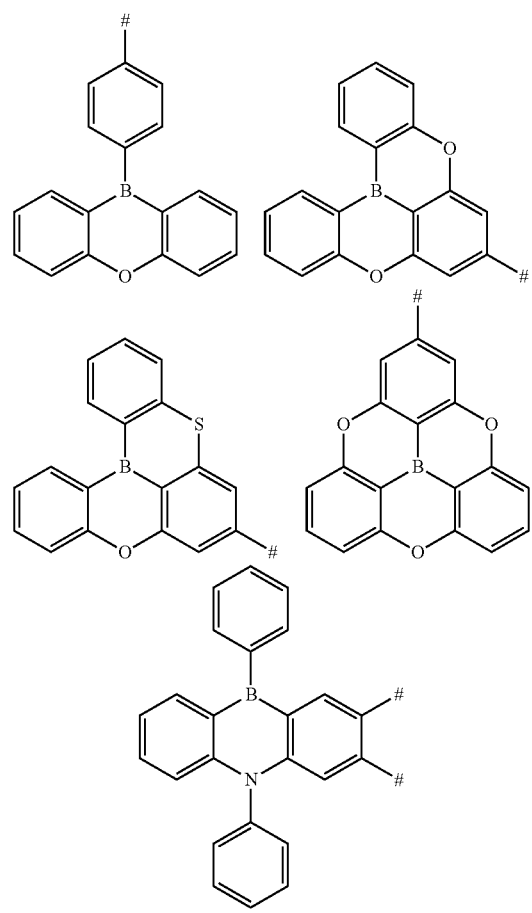
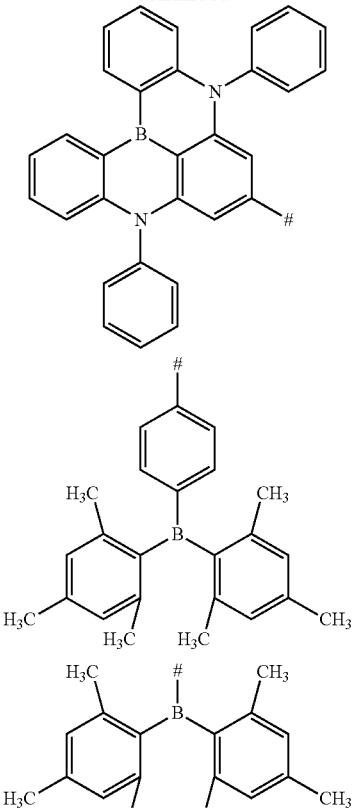
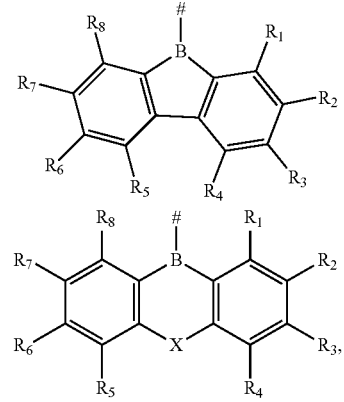
and, # represents a connection position; X is selected from BR$_9$, O, S, or NR$_9$; and R$_1$-R$_9$ are each independently selected from C1-20 alkyl, C1-20 alkoxy, C6-40 aryl, and C4-40 heteroaryl;

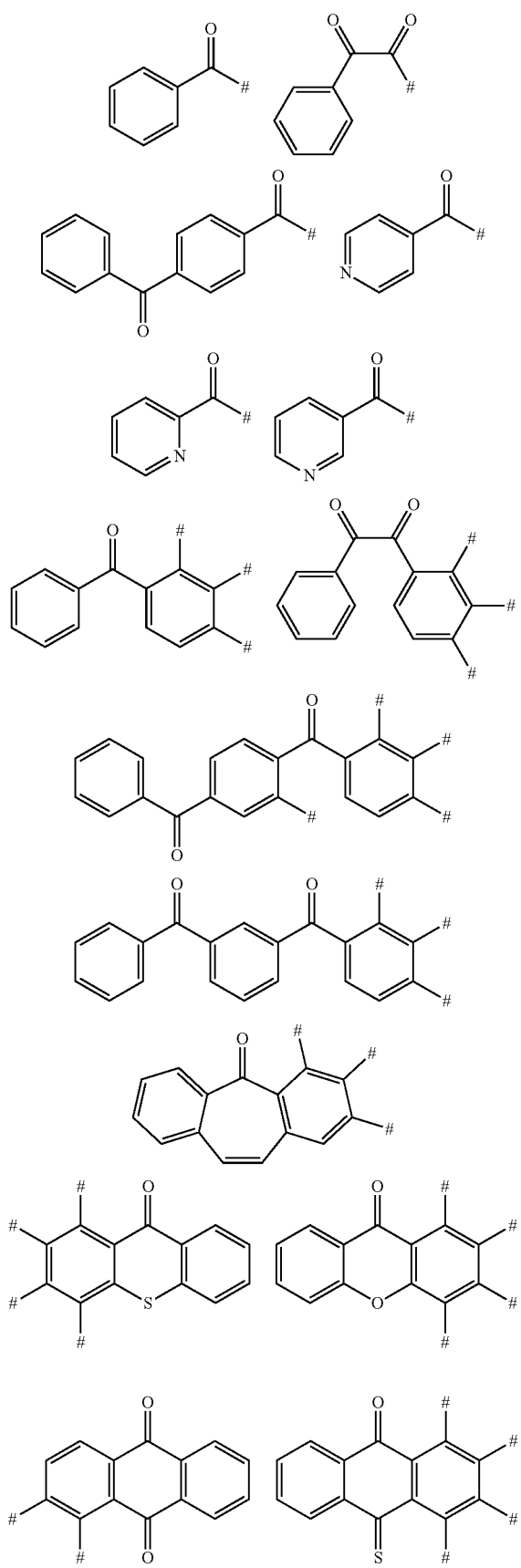
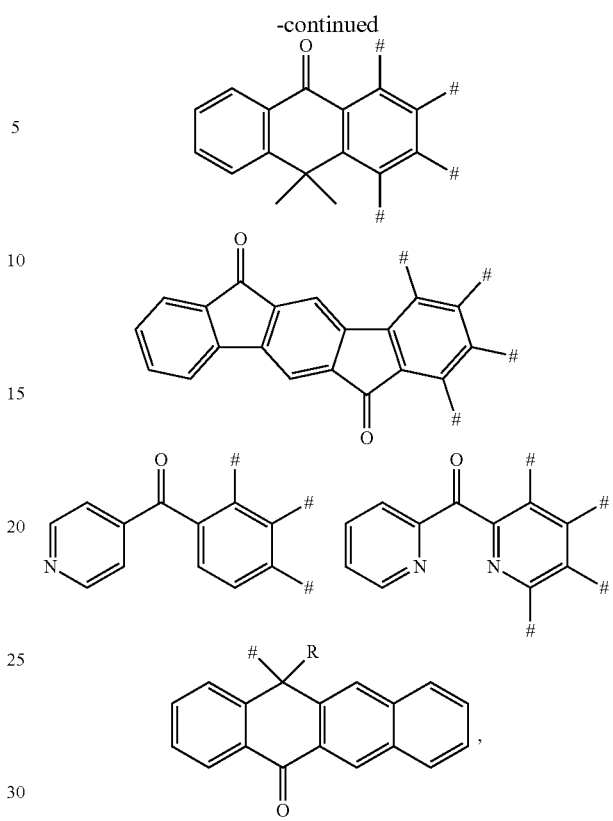
and, # represents a connection position, and in a structural formula, R represents C1-20 alkyl, C1-C20 alkoxy, C2-20 alkenyl, C2-20 alkynyl, C4-8 cycloalkyl, C6-40 aryl, and C4-40 heteroaryl;
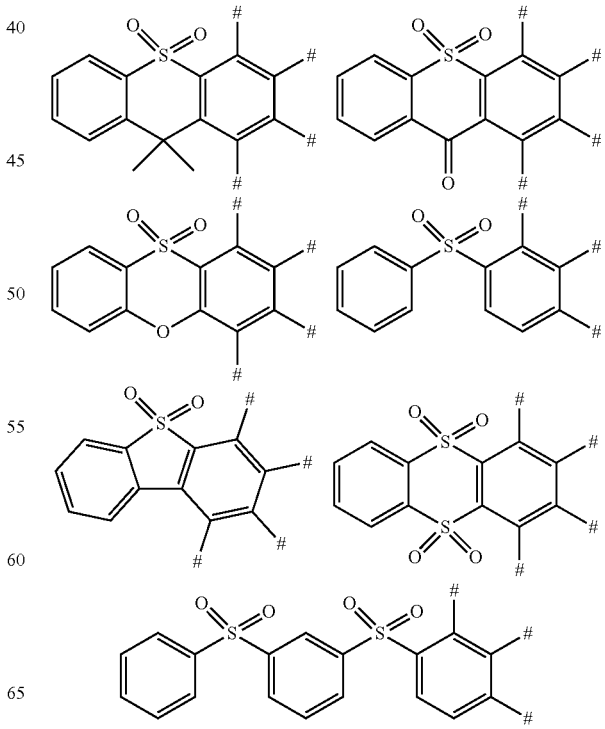

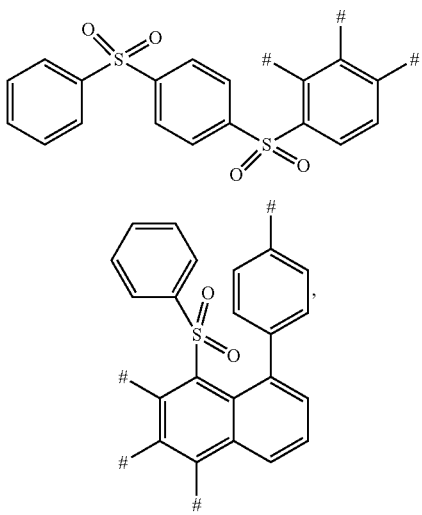

and, # represents a connection position;

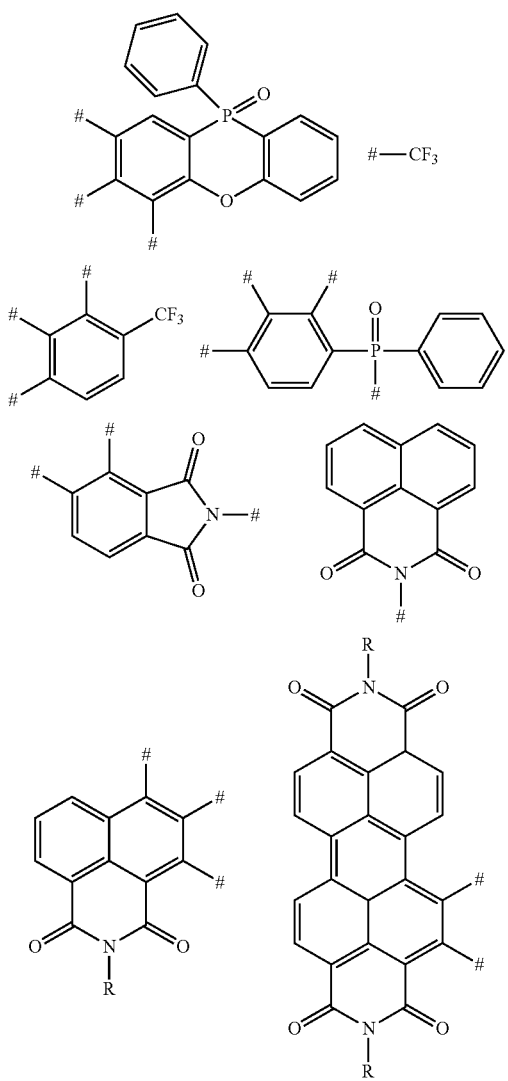

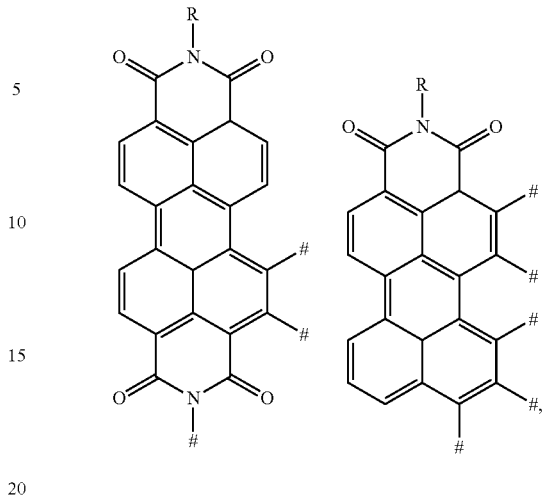

and, # represents a connection position, and R in each structural formula each independently represents C1-20 alkyl, C1-20 alkoxy, C2-20 alkenyl, C2-20 alkynyl, C4-8 cycloalkyl, C6-40 aryl, and C4-40 heteroaryl.

According to one embodiment of the present disclosure, r, s, u, and v are all selected from 1, and the C6-C40 aryl is selected from phenyl; and the C6-C40 heterocyclyl is selected from one or more of thienyl, thiazolyl, pyridyl, furyl, pyranyl, pyrrolyl, pyrazolyl, imidazolyl, oxazolyl, oxadiazolyl, triazolyl, thiadiazolyl, pyridazinyl, pyrimidinyl, pyrazinyl, and triazinyl.

According to one embodiment of the present disclosure, r, s, u, and v are all selected from 1, and $A_1$, $A_2$, $A_3$, and $A_4$ are each independently selected from one or more of

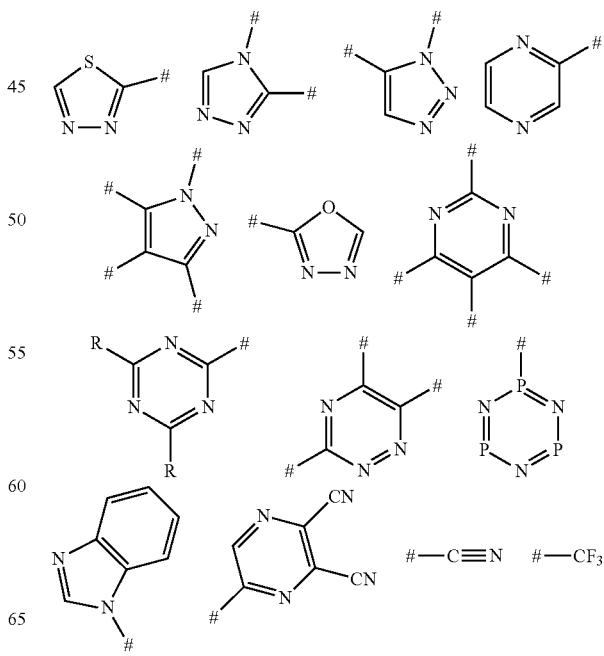

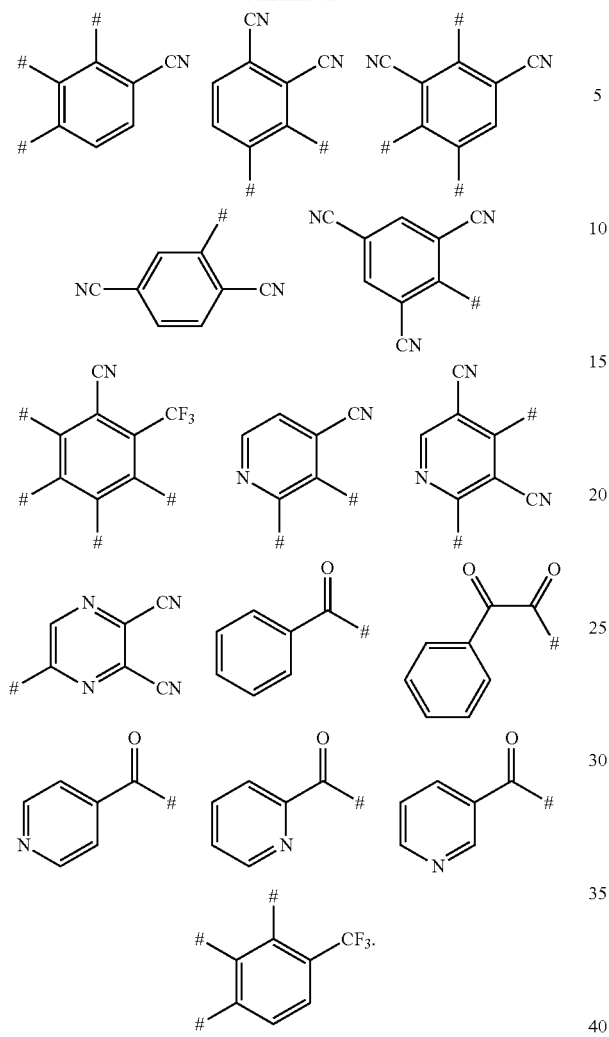
According to one embodiment of the present disclosure, the compound is any one selected from
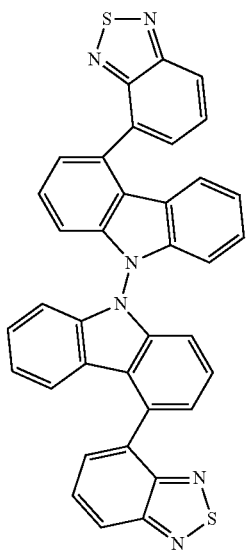
H01
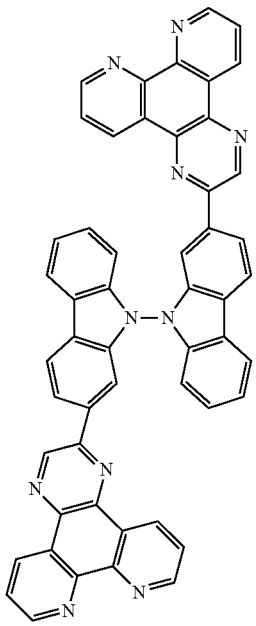
H02
H03

H04
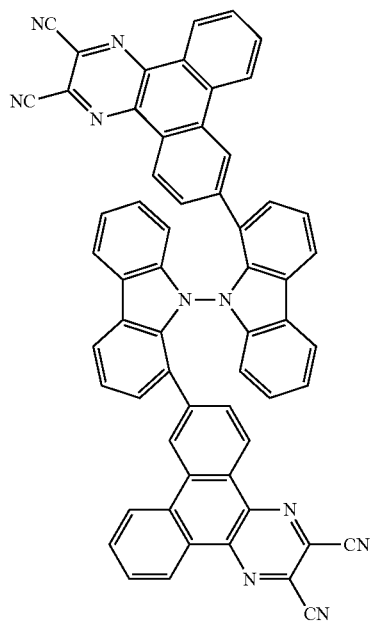
H05
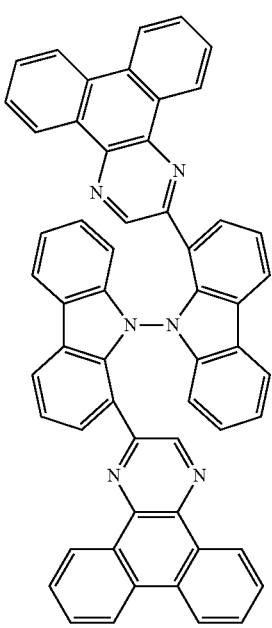
H06
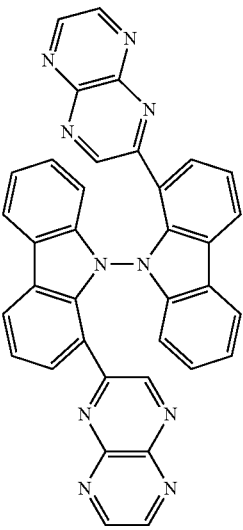
H07
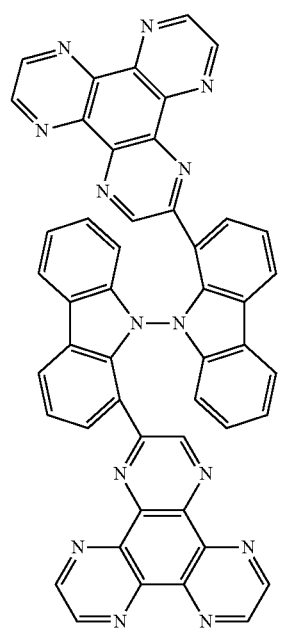

H08
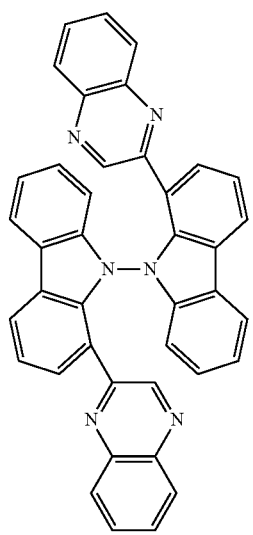
H09
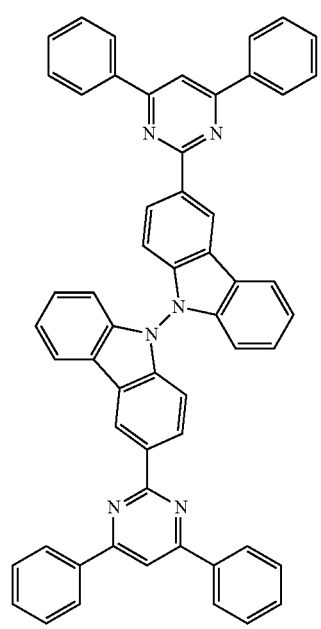
H10
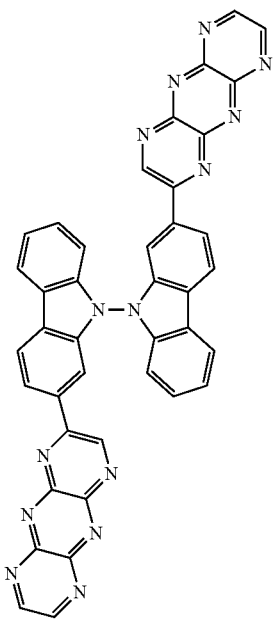
H11
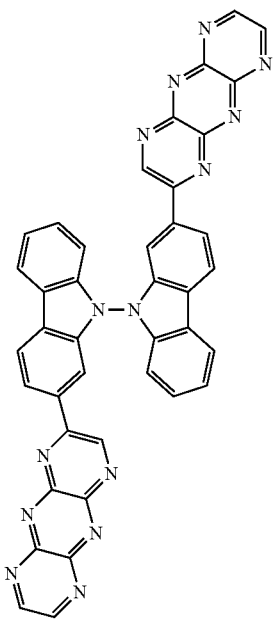

31
-continued
H12
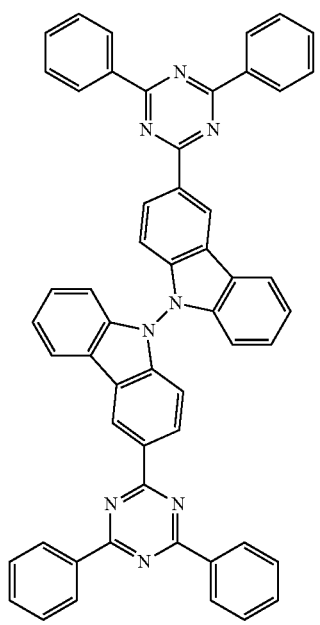
H13
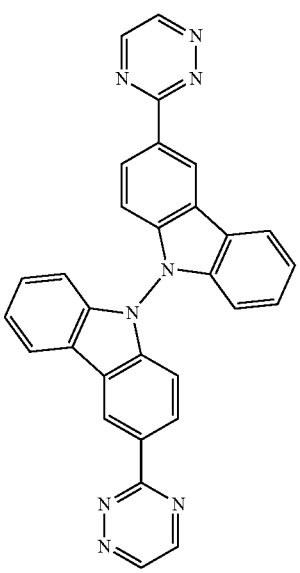
32
-continued
H14
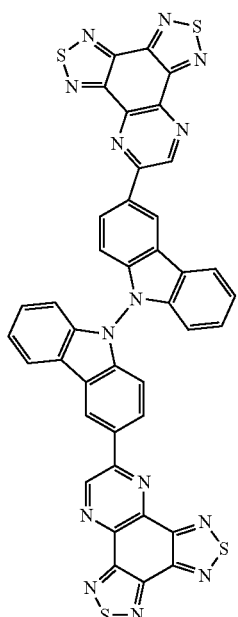
H15

H16
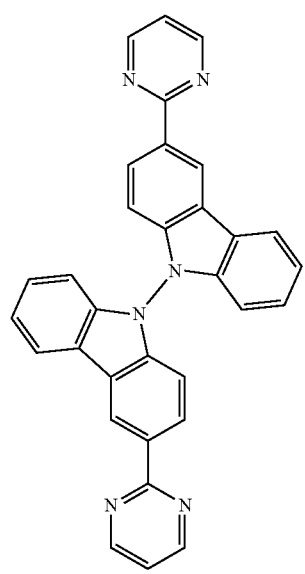
H17
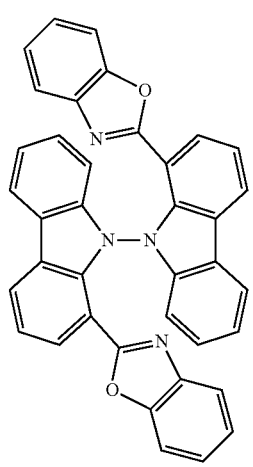
H18
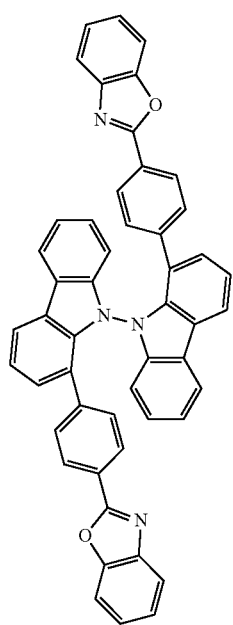
H19
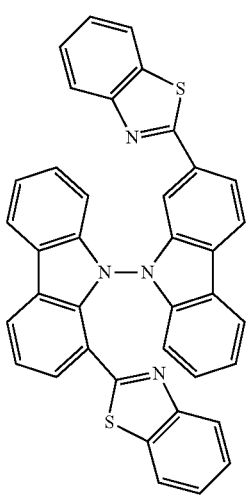
H20
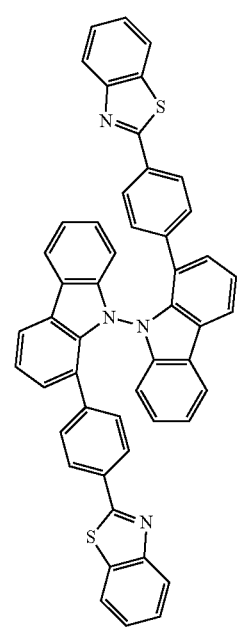

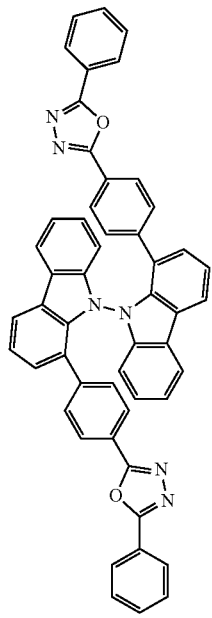 H21
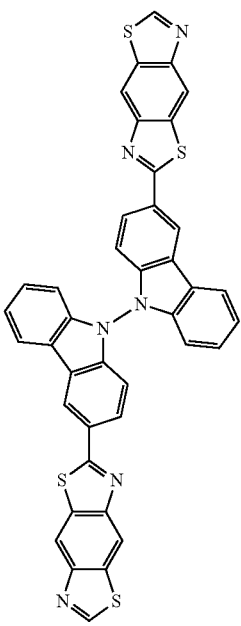 H23
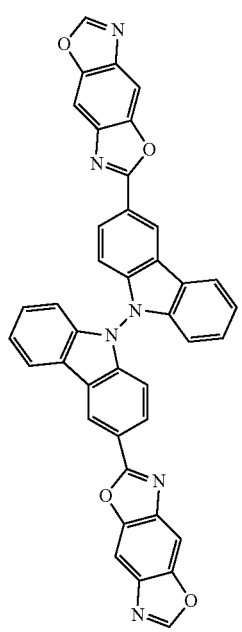 H22
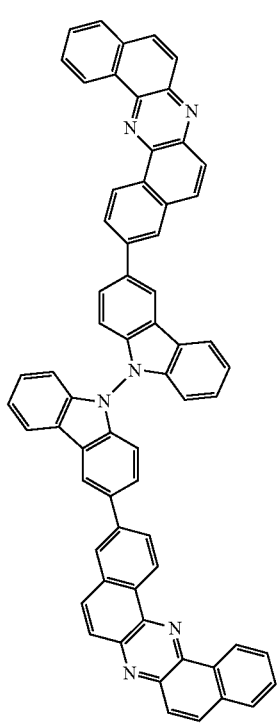 H24

| | |
|---|---|
| H25 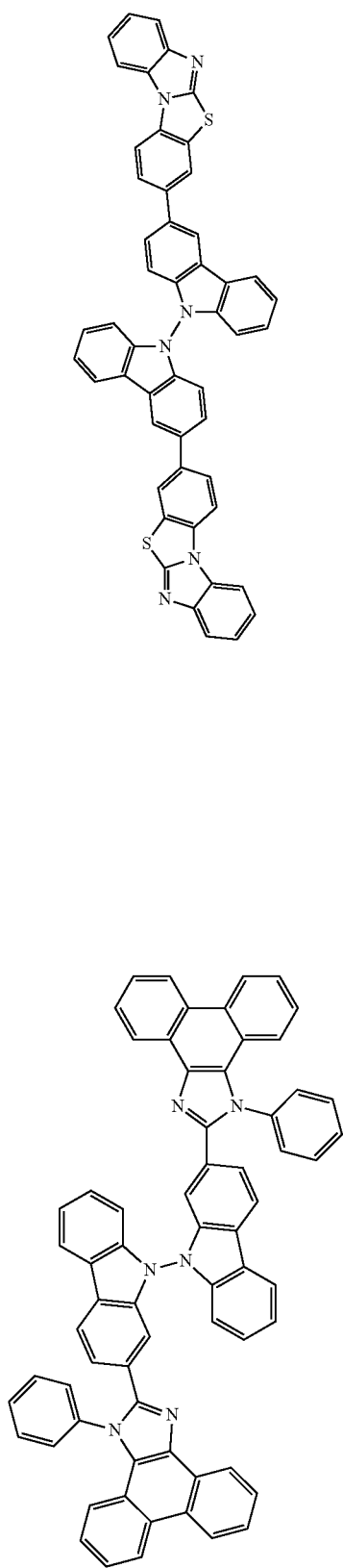 | H27 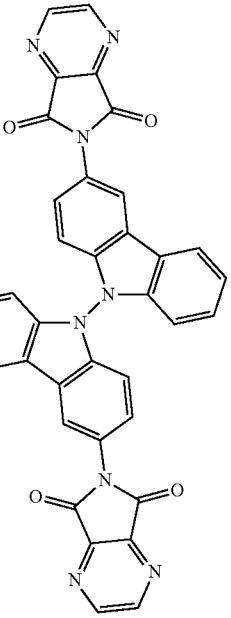 |
| H26 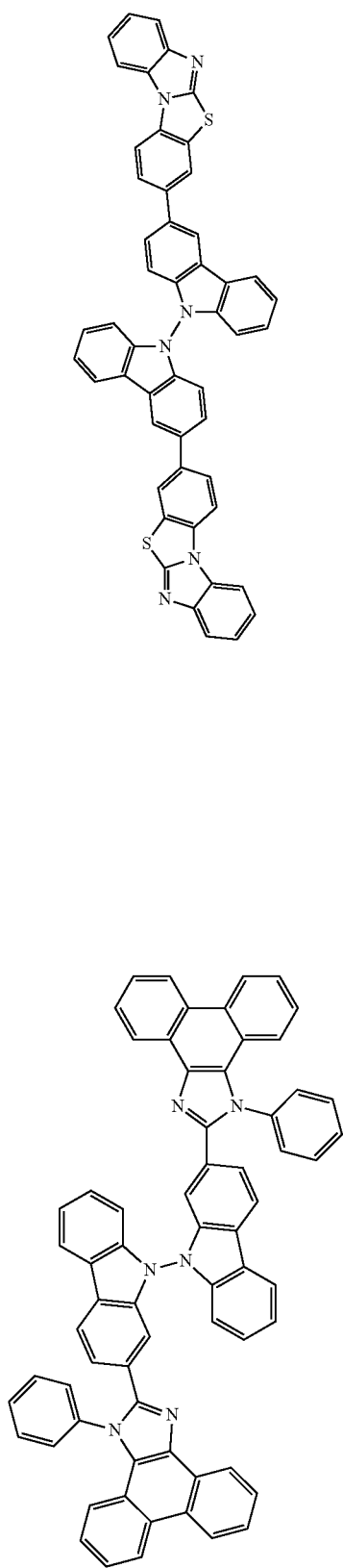 | H28 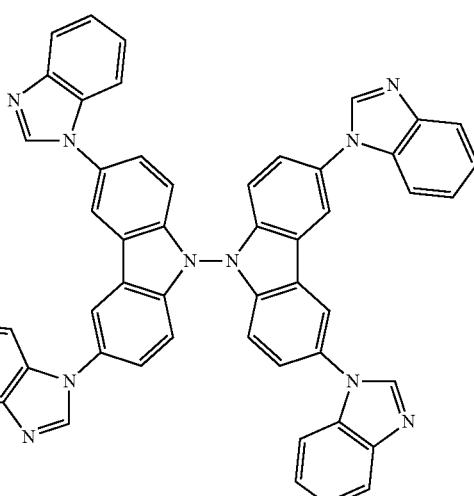 |
| | H29 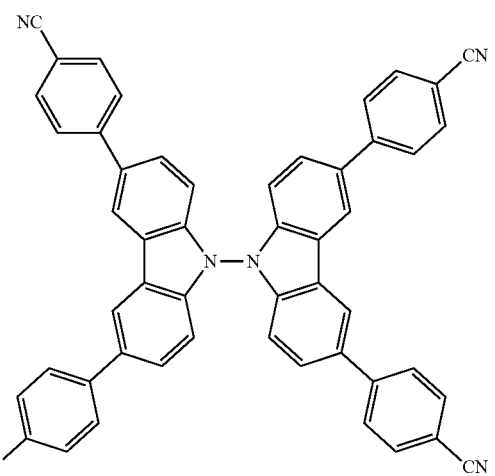 |

-continued
H30
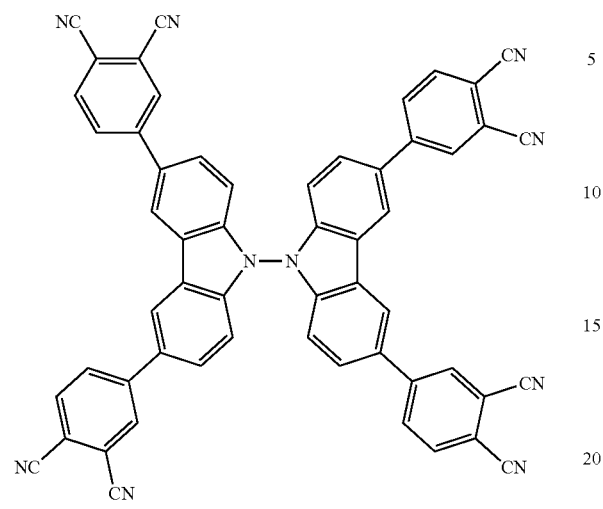
H31
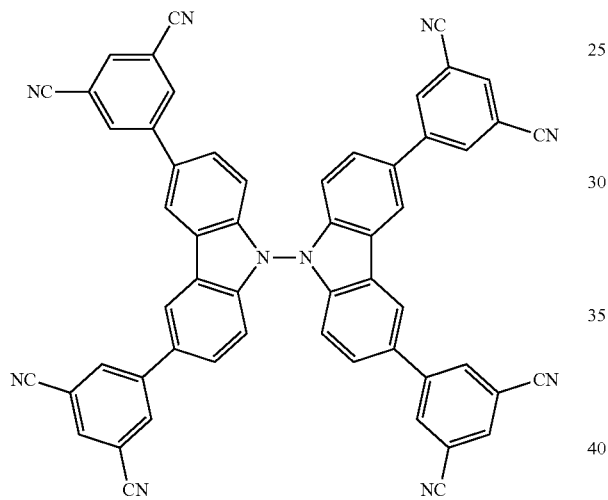
H32
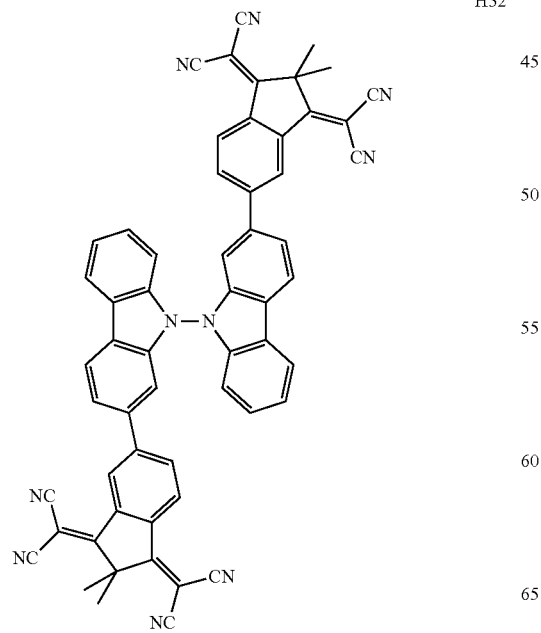
-continued
H33
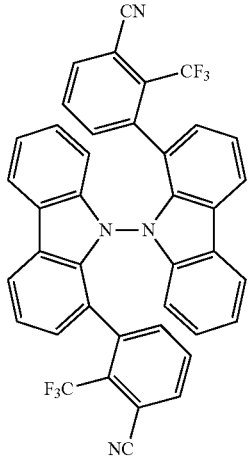
H34
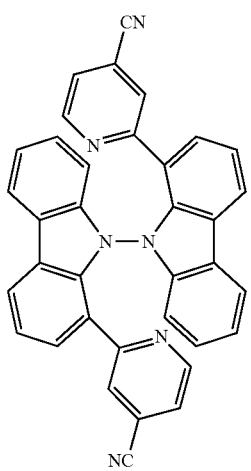
H35
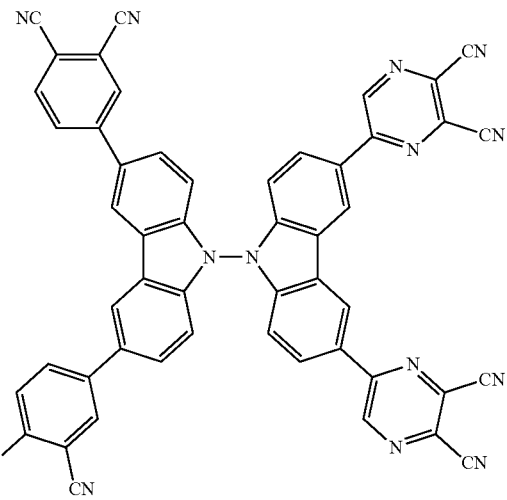

H36
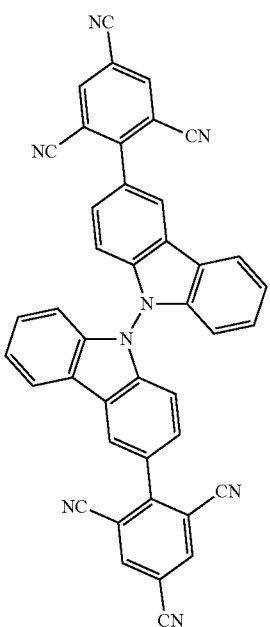
H37
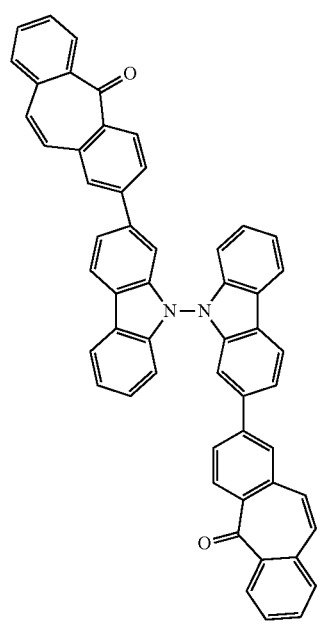
H38
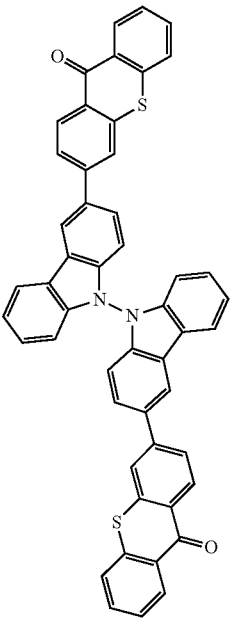
H39
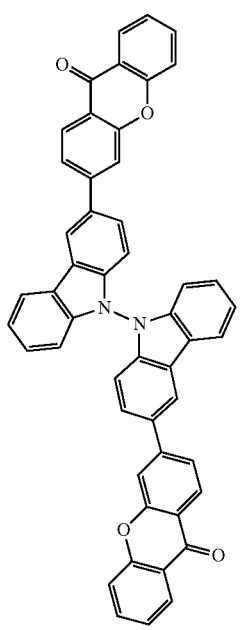

43
-continued
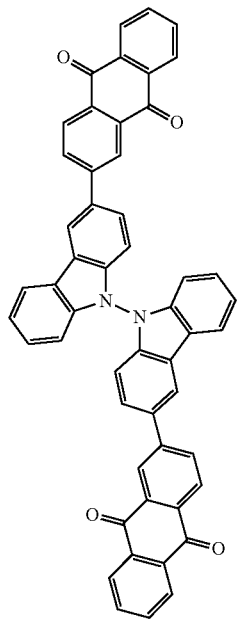
H40
44
-continued
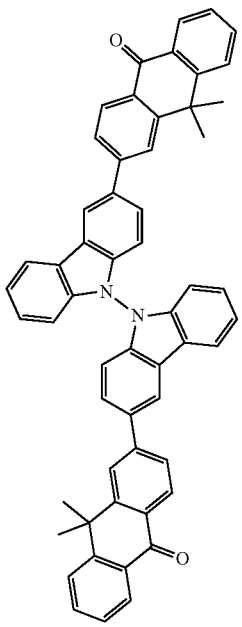
H42
H41
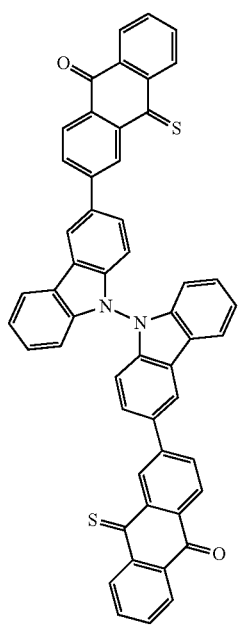
H43
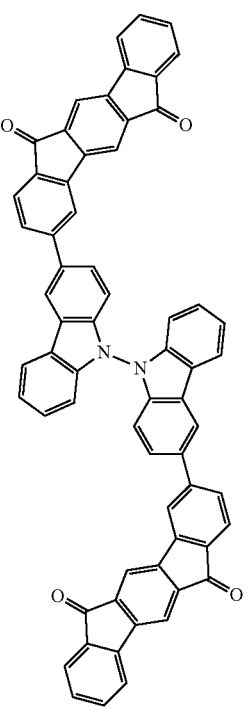

H44
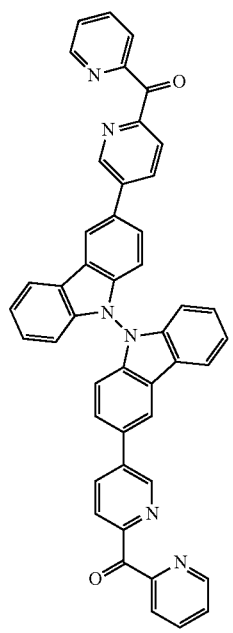
H45
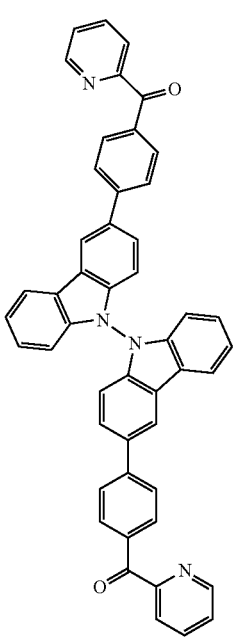
H46
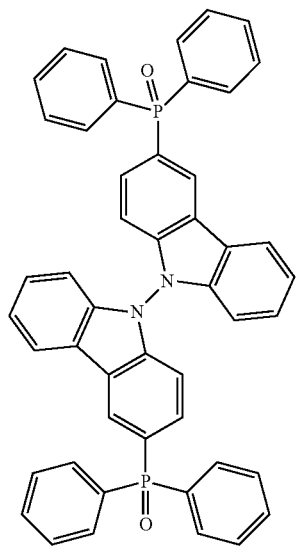
H47
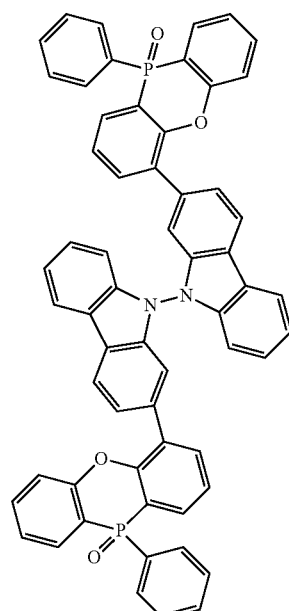
H48
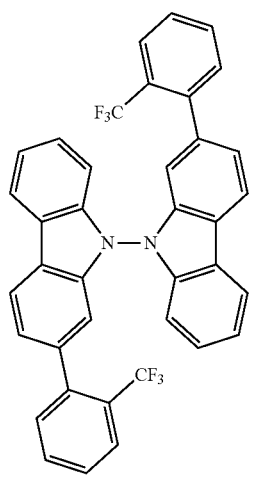

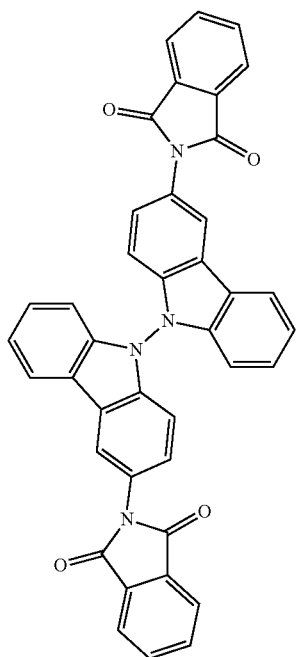
H49
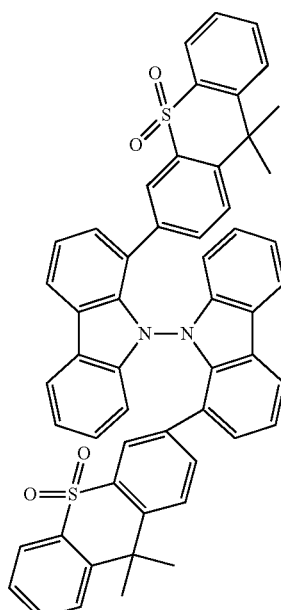
H51
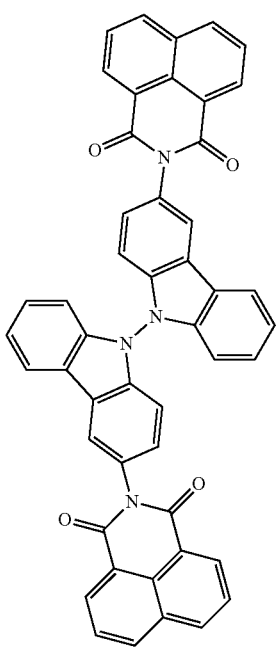
H50
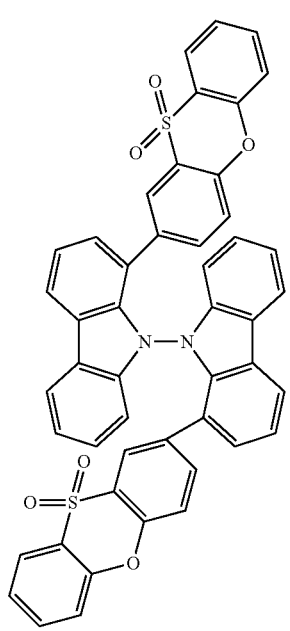
H52

H53
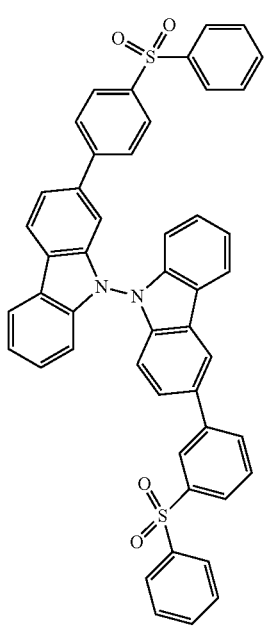
H54
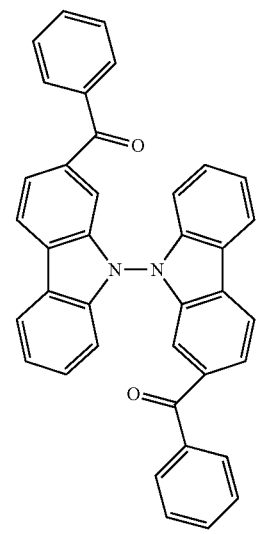
H55
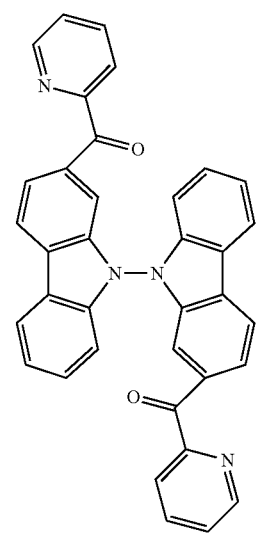
H56
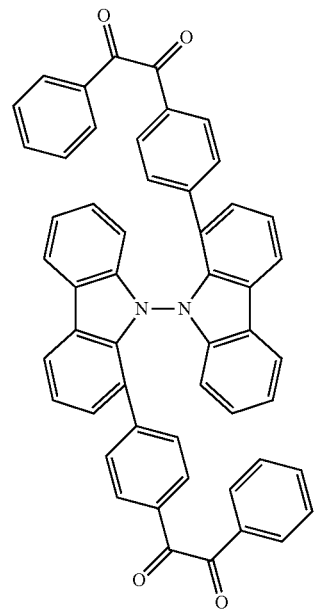
H57
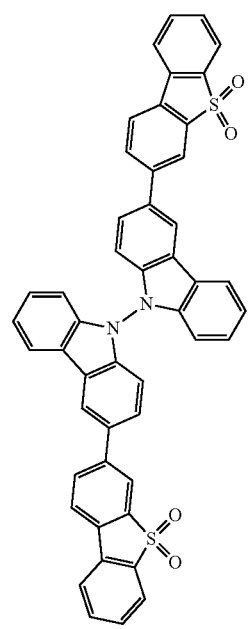

H58
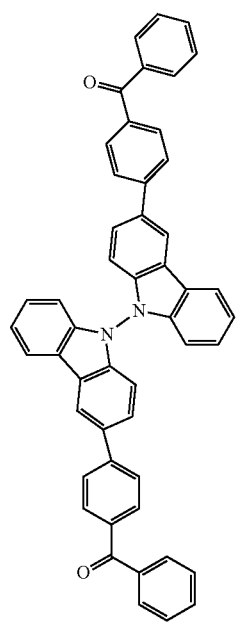
H59
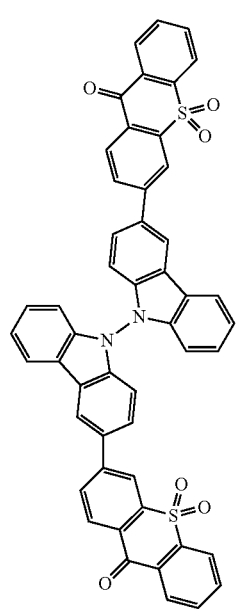
H60
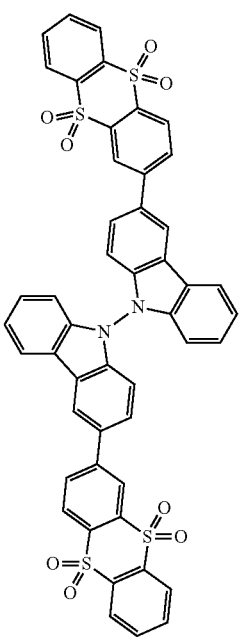
H61
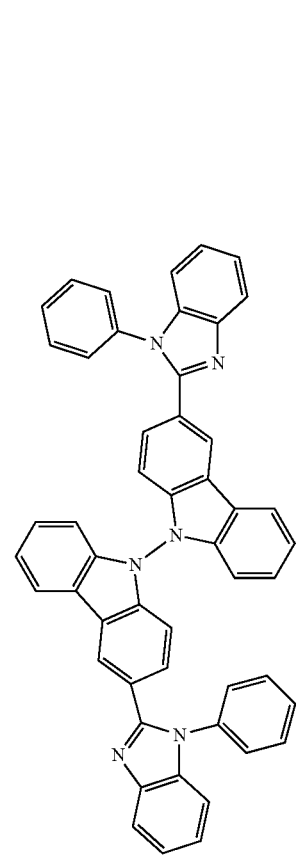

53
-continued
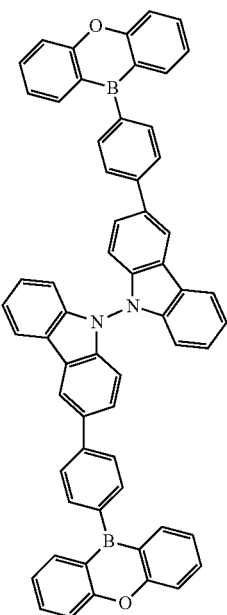
H62
54
-continued
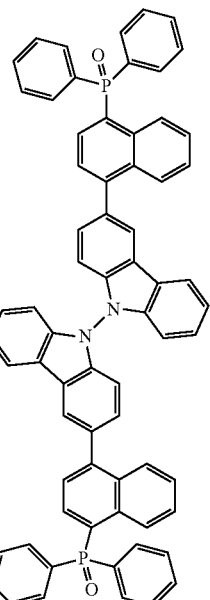
H64
H63
H65
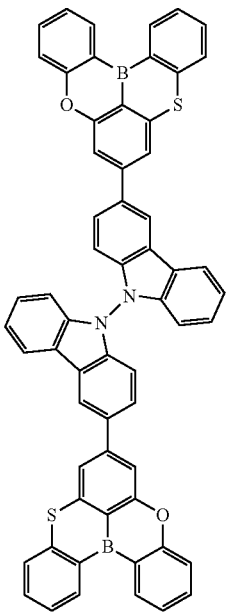

H66
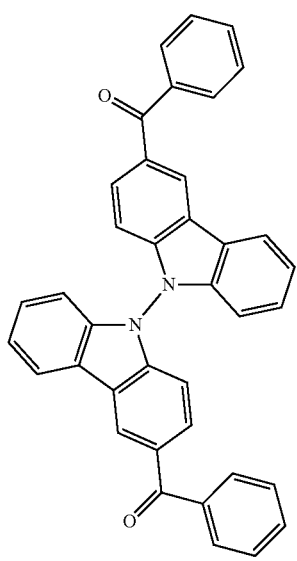
H68
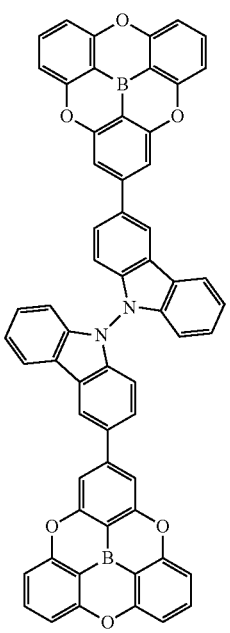
H67
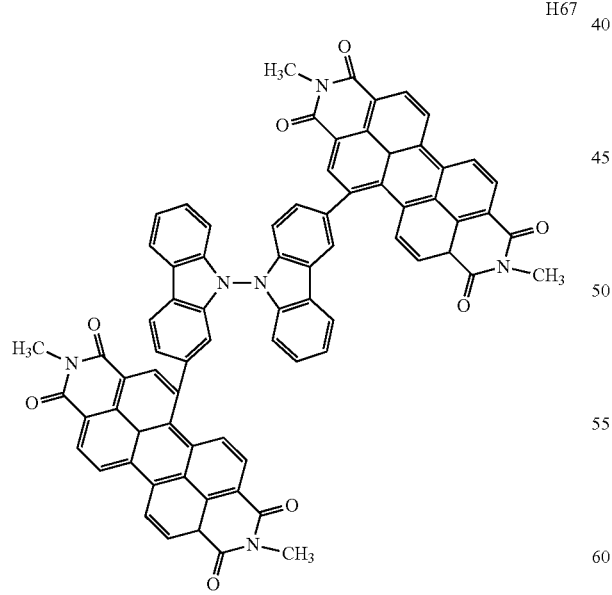
H69
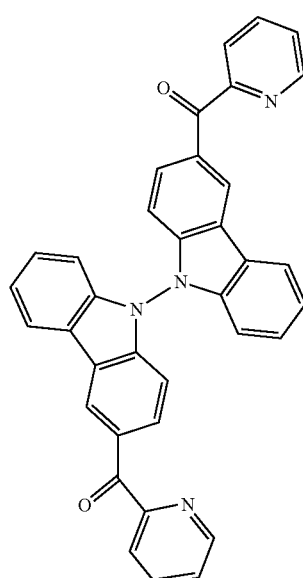

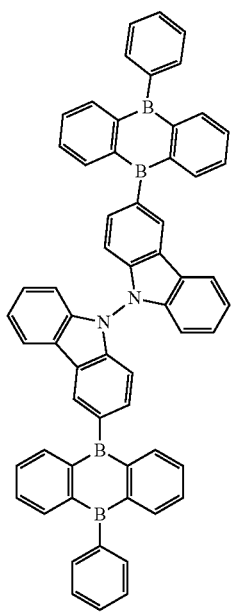 H70
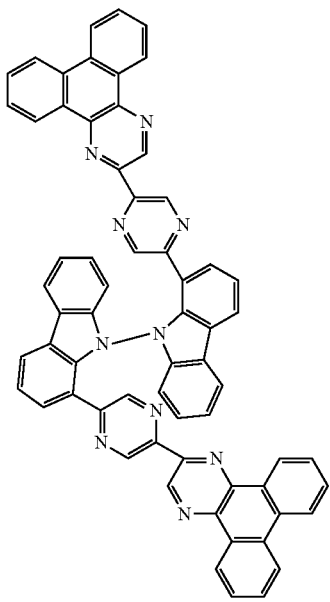 H72
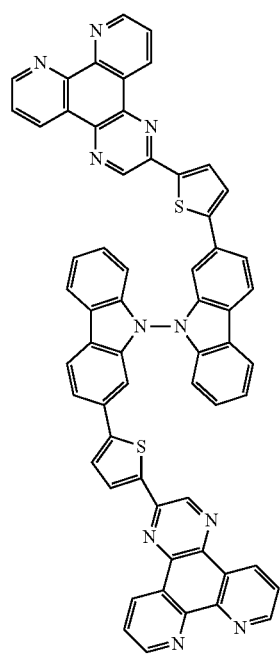 H71
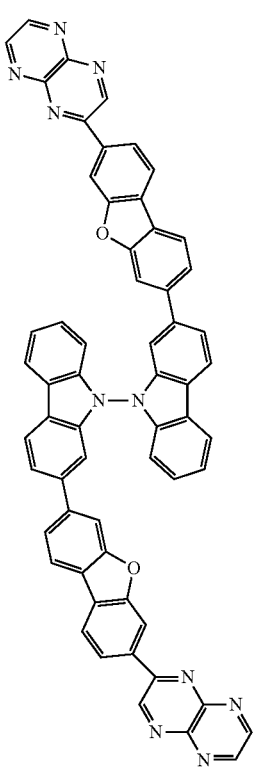 H73

H74
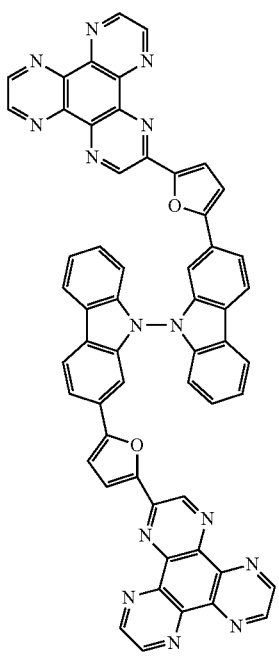
H75
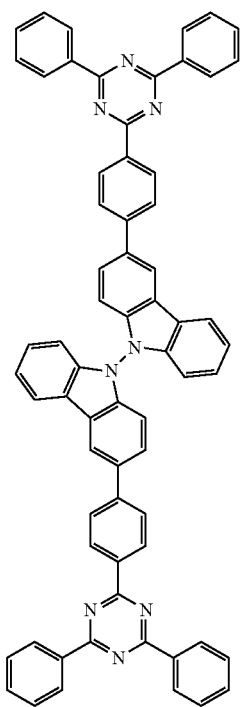
H76
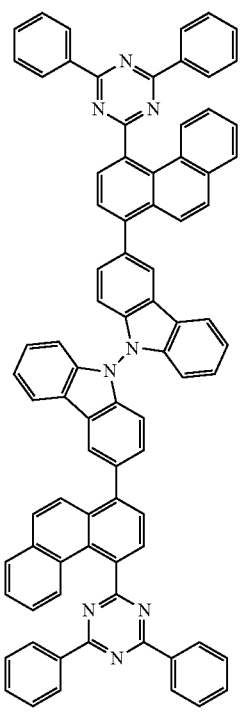
H77
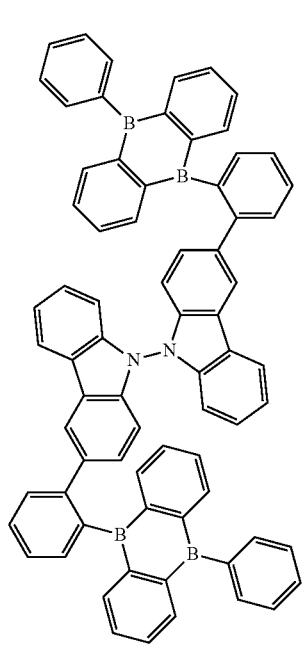

-continued

H78
H79

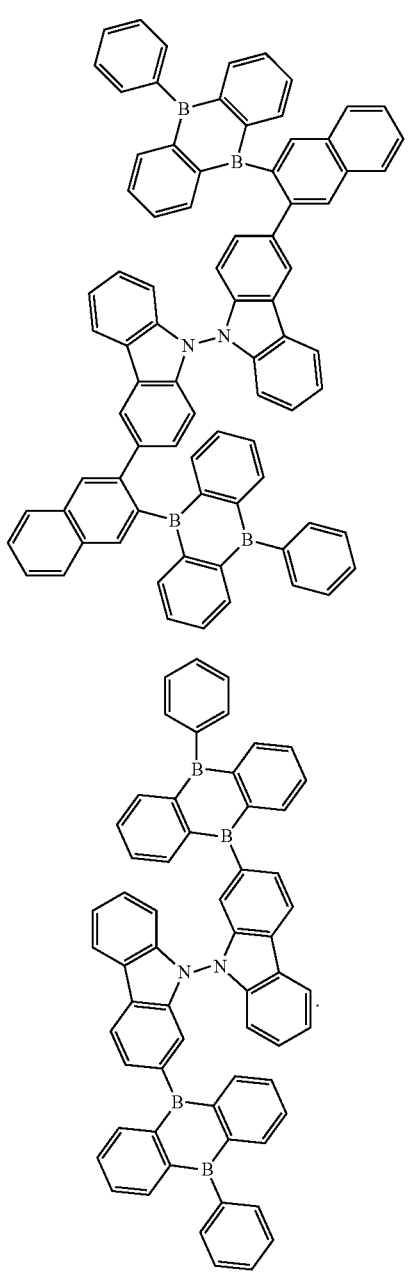

According to one embodiment of the present disclosure, the compound is any one selected from H12, H33, H44, H46, H60, and H79.

According to another embodiment of the present disclosure, an organic light emitting display device is provided, and the device includes an organic electroluminescence apparatus, and the organic electroluminescence apparatus includes:

an organic functional layer including one or more organic film layers, and at least one of the organic film layers serves as a luminescent layer; and the luminescent layer includes a luminescent material, and the luminescent material includes any one or more of the compounds provided by the present disclosure.

According to one embodiment of the present disclosure, the compound is used as a host material of the luminescent layer.

According to one embodiment of the present disclosure, the organic electroluminescence apparatus includes a substrate, an anode, a cathode, and an organic functional layer, and the anode and the cathode are arranged oppositely, and the organic functional layer is located between the anode and the cathode; and the organic functional layer includes an electron injection layer, an electron transport layer, a luminescent layer, a hole transport layer, and a hole injection layer.

The organic electroluminescence apparatus according to one embodiment of the present disclosure is shown in FIG. 1, and the apparatus includes a substrate 1, an ITO anode 2, a hole injection layer 3, a first hole transport layer 4, a second hole transport layer 5, a luminescent layer 6, a first electron transport layer 7, a second electron transport layer 8, a cathode 9, and a cap layer 10 which are arranged sequentially.

According to one embodiment of the present disclosure, the compound is used as the host material of the luminescent layer, the guest material is selected from a fluorescent material (for example BczVBi, coumarin-6, DCJTB, pyrene compounds, anthracene compounds, and the like), a thermally activated delayed fluorescent material, or a phosphorescence material, the difference between HOMO of the host material and HOMO of the guest material is less than 0.6 eV, or the difference between LUMO of the host material and LUMO of the guest material is less than 0.6 eV.

According to one embodiment of the present disclosure, the compound is used as the host material of the luminescent layer, the guest material is selected from a fluorescent material (for example BczVBi, coumarin-6, DCJTB, pyrene compounds, anthracene compounds, and the like), or a thermally activated delayed fluorescent material, the singlet-state energy of the guest material is lower than that of the host material, and the difference between the singlet-state energy of the host material and the singlet-state energy of the guest material is less than 1.0 eV.

According to one embodiment of the present disclosure, the compound is used as the host material of the luminescent layer, the guest material is selected from a phosphorescence material, the triplet-state energy of the guest material is lower than that of the host material, and the difference between the triplet-state energy of the host material and the triplet-state energy of the guest material is less than 1.0 eV.

According to one embodiment of the present disclosure, the organic electroluminescence apparatus includes a substrate, an anode, a cathode, and an organic functional layer, and the anode and the cathode are arranged oppositely, and the organic functional layer is located between the anode and the cathode; and the organic functional layer includes an electron injection layer, an electron transport layer, a luminescent layer, a hole transport layer, and a hole injection layer.

The structure of the organic electroluminescence apparatus may include a single luminescent layer and may also include multiple luminescent layers.

The hole injection material, the hole transport material, and the electron barrier material may be selected from materials such as N,N'-diphenyl-N,N'-(1-naphthyl)-1,1'-biphenyl-4,4'-diamine (α-NPD), 4,4',4"-tri(carbazol-9-yl)triphenylamine (TCTA), 1,3-dicarbazol-9-ylbenzene (mCP), 4,4'-di(9-carbazolyl)biphenyl (CBP), 3,3'-di(N-carbazolyl)-1,1'-biphenyl (mCBP), 2,3,6,7,10,11-hexacyano-1,4,5,8,9,12-hexaazatriphenylene (HATCN), 4,4'-cyclohexylbis[N,N-bis(4-methylphenyl)aniline] (TAPC), N,N'-diphenyl-N,N'-(1-naphthyl)-1,1'-biphenyl-4,4'-diamine (α-NPD), N,N'-bis(naphthalen-2-yl)-N,N'-di(phenyl)biphenyl-4,4'-diamine (NPB), poly(3,4-ethylenedioxythiophene)-polystyrene sulfonate (PEDOT:PSS), polyvinyl carbazole (PVK), 9-phenyl-3,9-dicarbazole (CCP), and molybdenum trioxide ($MoO_3$), but not limited to the above several materials.

The hole barrier material, the electron transport material, and the electron injection material may be selected from materials such as 2,8-bis(diphenylphosphinyl)dibenzothiophene (PPT), TSPO1, TPBi, 2,8-bis(diphenylphosphine oxide)dibenzofuran (PPF), bis[2-(diphenylphosphino)phenyl]ether oxide (DPEPO), lithium fluoride (LiF), 4,6-bis(3,5-di(3-pyridin)ylphenyl)-2-methylpyrimidine (B3PYMPM), 4,7-diphenyl-1,10-phenanthroline (Bphen), 1,3,5-tri[(3-pyridyl)-3-phenyl]benzene (TmPyBP), tri[2,4,6-trimethyl-3-(3-pyridyl)phenyl]borane (3TPYMB), 1,3-bis(3,5-dipyridin-3-ylphenyl)benzene (B3PYPB), 1,3-bis[3,5-di(pyridin-3-yl)phenyl]benzene (BMPYPHB), 2,4,6-tri(biphen-3-yl)-1,3,5-triazine (T2T), diphenylbis[4-(pyridin-3-yl)phenyl]silane (DPPS), caesium carbonate (Cs2O3), bis (2-methyl-8-hydroxyquinoline-N1,$O_8$)-(1,1'-biphenyl-4-hydroxy)aluminum (BAlq), 8-hydroxyquinoline-lithium (Liq), and tri(8-hydroxyquinoline) aluminum (Alq3), but not limited to the above several materials.

According to the present disclosure, the material of the anode may be metals, for example copper, gold, silver, ferrum, chromium, nickel, manganese, palladium, platinum, etc.; may be metal oxides, for example metal oxides of indium oxide, zinc oxide, indium tin oxide (ITO), indium-zinc oxide (IZO), etc.; may be alloy; and may be an electric-conductive polymer, for example polyaniline, polypyrrole, poly(3-methylthiophene), and the like. Besides the above-mentioned materials which contribute to hole injection and combinations thereof, the material of the anode also may be other known materials suitable for serving as an anode.

According to the present disclosure, the material of the cathode may be metals, for example aluminum, magnesium, silver, indium, tin, titanium, and the like; may be alloy, for example Mg/Ag; may be a composite material of metals and inorganic compounds, for example multilayer metallic materials, i.e., LiF/Al, $LiO_2$/Al, $BaF_2$/Al, etc. Besides the above-mentioned materials which contribute to electron injection and combinations thereof, the material of the cathode may also be other known materials suitable for serving as a cathode.

According to the present disclosure, the substrate may be a rigid substrate (borosilicate glass, float soda-lime glass, glass having high refractive index, stainless steel, and the like) and may also be a flexible substrate (for example, a polyimide (PI) plastic substrate, a polyethylene terephthalate (PET) plastic substrate, a polyethylene naphthalate (PEN) plastic substrate, a polyethersulfone resin substrate (PES), a polycarbonate (PC) plastic substrate, an ultra-thin flexible glass substrate, a metal foil substrate, and the like).

According to the present disclosure, a production process of the organic electroluminescence apparatus includes the following steps: forming an anode (a first electrode) on a transparent or non-transparent smooth substrate, forming an organic functional layer on the anode, and forming a cathode (a second electrode) on the organic functional layer. The organic functional layer can be formed by applying known film forming methods, such as evaporation, sputtering, spin coating, dipping, and ion plating.

Figure 2:
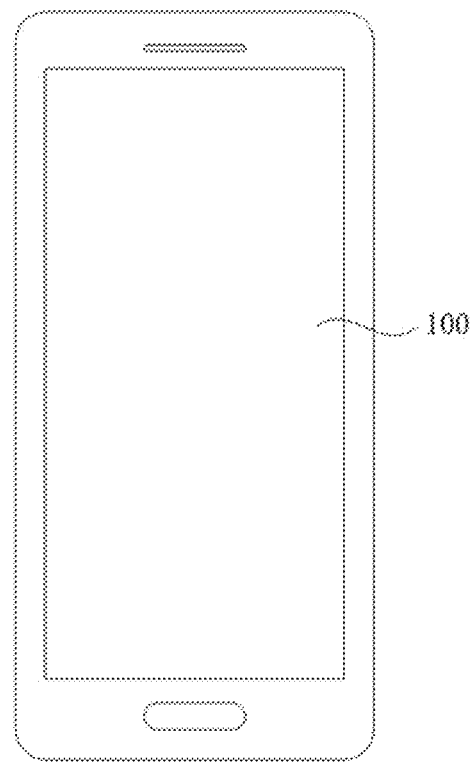
FIG. 2 is a schematic diagram of a mobile phone display screen.

The organic light emitting display device provided by the present disclosure for example may be a mobile phone display screen, a computer display screen, a liquid crystal television display screen, and the like. Particular limitation is not made by the present embodiment. FIG. 2 is a schematic diagram of a mobile phone display screen, and 100 represents the display screen.

Thus, it can be seen that there are many optional factors for the compound, the organic electroluminescence apparatus, and the display device, provided by the present disclosure, and different embodiments can be combined according to the claims of the present disclosure. Embodiments of the present disclosure are only intended to specifically describe the present disclosure, rather than limit the present disclosure. The present disclosure will be further described below with reference to the organic electroluminescence apparatus containing the compound provided by the present disclosure as an embodiment.

Intermediates S1, S3, S5, and S7-S12 come from commercially available products.

Preparation methods for a plurality of intermediates are presented below,

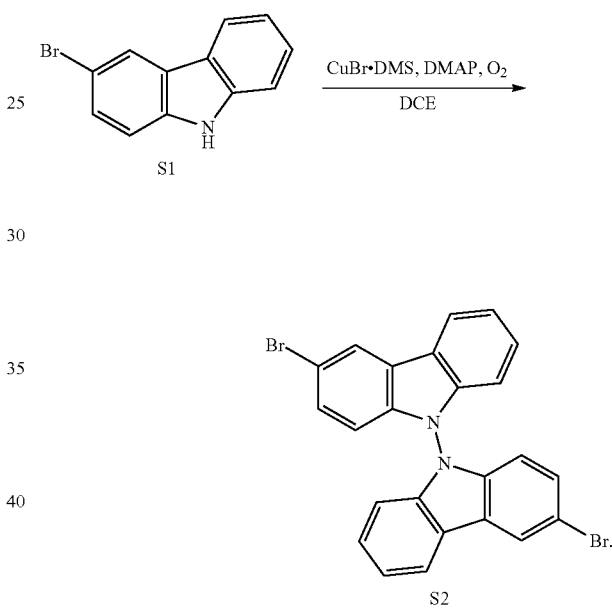

S1 (0.5 mmol), cuprous bromide dimethyl sulfide CuBr.DMS (0.1 mmol) and 4-dimethylaminopyridine DMAP (0.2 mmol) are loaded into a 100 ml flasket containing a stirring rod. O2 purging is performed with an O2 balloon for 10 minutes to replace the gas atmosphere in a reaction bottle. 5 mL of 1,2-dichloroethane (DCE) is added by a syringe. Reactants are stirred in an oil bath at 60° C. for 17 h. After 17 h, the reactants are cooled to room temperature, diluted with 25 mL of dichloromethane (DCM), and washed with 25 mL of a saturated $NH_4Cl$ aqueous solution. Then, organic matters are washed with 10 mL of water, and dried with anhydrous sodium sulfate. Filtering and vacuum concentration are performed to obtain a crude product. Then, the crude product is purified through silica-gel chromatography (n-hexane:dichloromethane=5:1) to obtain a white solid S2 (0.1 mmol, 40%).

MALDI-TOF MS: C24H14Br2N2, m/z calculated value: 488.0; test value: 487.9.

Elemental analysis calculated value: C, 58.81; H, 2.88; Br, 32.60; N, 5.71; test value: C, 58.84; H, 2.91; Br, 32.57; N, 5.68,

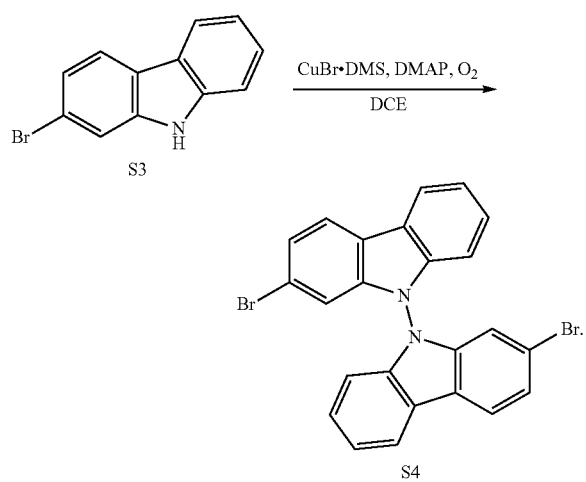

S3 (0.8 mmol), cuprous bromide dimethyl sulfide CuBr.DMS (0.16 mmol), and 4-dimethylaminopyridine DMAP (0.32 mmol) are loaded into a 100 ml flasket containing a stirring rod. 02 purging is performed with an 02 balloon for 10 minutes to replace the gas atmosphere in a reaction bottle. 10 mL of 1,2-dichloroethane (DCE) is added by a syringe. Reactants are stirred in an oil bath at 60° C. for 17 h. After 17 h, the reactants are cooled to room temperature, diluted with 45 mL of dichloromethane (DCM), and washed with 45 mL of a saturated NH$_4$Cl aqueous solution. Then, organic matters are washed with 15 mL of water, and dried with anhydrous sodium sulfate. Filtering and vacuum concentration are performed to obtain a crude product. Then, the crude product is purified through silica-gel chromatography (n-hexane:dichloromethane=5:1) to obtain a white solid S4 (0.15 mmol, 38%).

MALDI-TOF MS: C24H14Br2N2, m/z calculated value: 488.0; test value: 488.2.

Elemental analysis calculated value: C, 58.81; H, 2.88; Br, 32.60; N, 5.71; test value: C, 58.83; H, 2.90; Br, 32.56; N, 5.67,

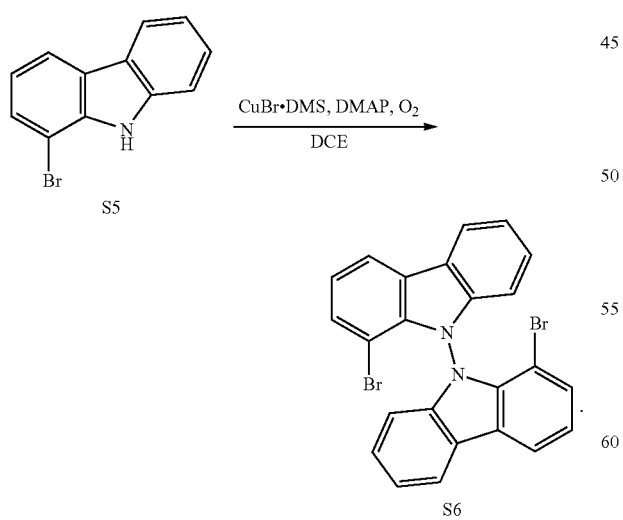

S5 (2 mmol), cuprous bromide dimethyl sulfide CuBr.DMS (0.4 mmol), and 4-dimethylaminopyridine DMAP (0.8 mmol) are loaded into a 250 ml flasket containing a stirring rod. 02 purging is performed with an 02 balloon for 10 minutes to replace the gas atmosphere in a reaction bottle. 25 mL of 1,2-dichloroethane (DCE) is added by a syringe. Reactants are stirred in an oil bath at 60° C. for 17 h. After 17 h, the reactants are cooled to room temperature, diluted with 80 mL of dichloromethane (DCM), and washed with 80 mL of a saturated NH$_4$Cl aqueous solution. Then, organic matters are washed with 40 mL of water, and dried with anhydrous sodium sulfate. Filtering and vacuum concentration are performed to obtain a crude product. Then, the crude product is purified through silica-gel chromatography (n-hexane:dichloromethane=5:1) to obtain a white solid S6 (0.7 mmol, 35%).

MALDI-TOF MS: C24H14Br2N2, m/z calculated value: 488.0; test value: 488.1.

Elemental analysis calculated value: C, 58.81; H, 2.88; Br, 32.60; N, 5.71; test value: C, 58.82; H, 2.90; Br, 32.54; N, 5.66.

Preparation methods and results of a plurality of specific compounds are presented below.

Preparation Example 1 Synthesis of H12

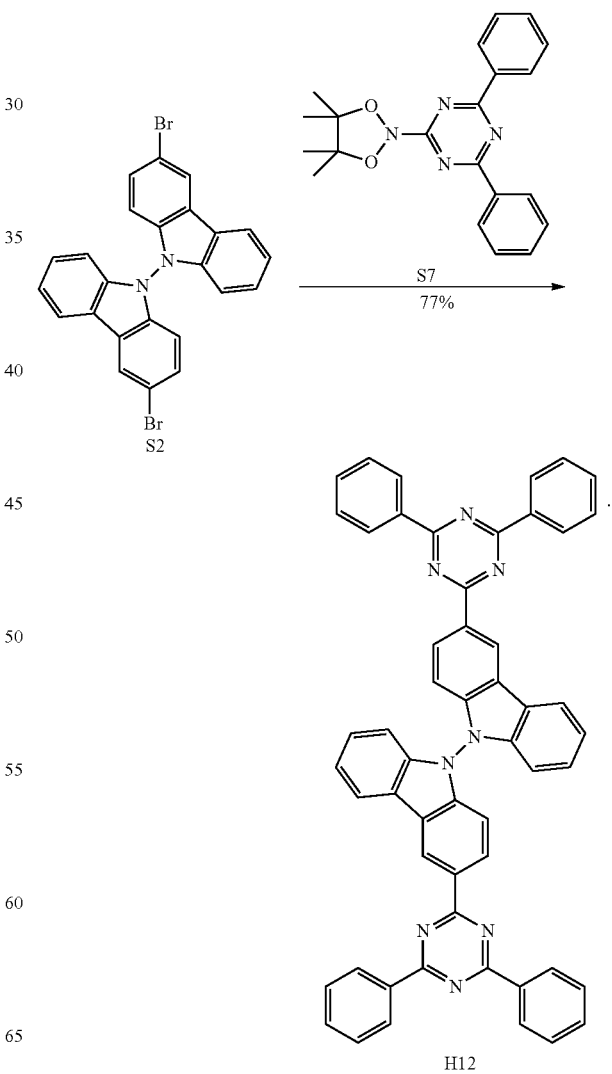

The compounds S2 (1.5 mmol), S7 (3.2 mmol), [Pd₂(dba)₃].CHCl₃ (0.1 mmol), and HP(tBu)₃.BF₄ (0.2 mmol) are weighed and added into a 100 mL two-neck flask under protection of nitrogen gas. 30 mL of toluene (N₂ is introduced for 15 min in advance to remove oxygen gas) is injected into the two-neck flask, then 2.5 mL of 1M K₂CO₃ aqueous solution (N₂ is introduced for 15 min in advance to remove oxygen gas) is dropwise added, and stirred at room temperature overnight. After the end of the reaction, 20 mL of deionized water is added, and then several droplets of 2M HCl are dripped. Extraction is performed with dichloromethane. The organic phase is collected, and dried with anhydrous Na₂SO₄. The dried solution is filtered, and the solvent is removed with a rotary evaporator to obtain a crude product. The crude product is purified through a silica-gel chromatographic column to finally obtain a solid H12 (1.16 mmol, 71%).

MALDI-TOF MS: m/z calculated value: C54H34N8: 794.3; measured value: 794.4; Elemental analysis calculated value: C, 81.59; H, 4.31; N, 14.10; test value: C, 81.62; H, 4.32; N, 14.06.

Preparation Example 2 Synthesis of H33 aqueous solution (N₂ is introduced for 15 min in advance to remove oxygen gas) is dropwise added, and stirred at room temperature overnight. After the end of the reaction, 25 mL of deionized water is added, and then several droplets of 2M HCl are dripped. Extraction is performed with dichloromethane. The organic phase is collected, and dried with anhydrous Na₂SO₄. The dried solution is filtered, and the solvent is removed with a rotary evaporator to obtain a crude product. The crude product is purified through a silica-gel chromatographic column to finally obtain a solid H33 (1.32 mmol, 68%).

MALDI-TOF MS: m/z calculated value: C40H20F6N4: 670.2; measured value: 670.3; Elemental analysis calculated value: C, 71.64; H, 3.01; F, 17.00; N, 8.35; test value: C, 71.67; H, 3.03; F, 19.97; N, 8.33.

Preparation Example 3 Synthesis of H44

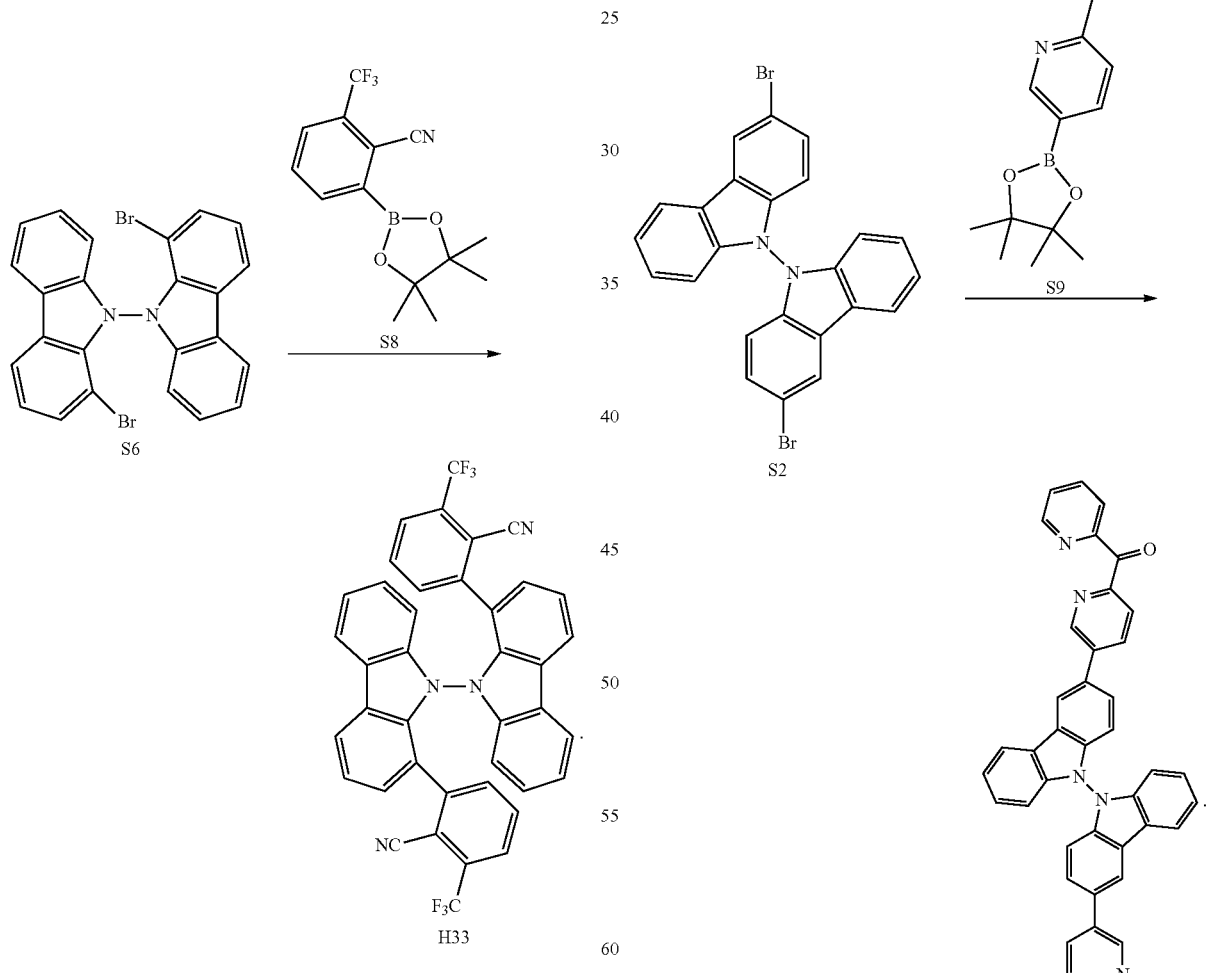

The compounds S6 (1.95 mmol), S8 (4.16 mmol), [Pd₂(dba)₃].CHCl₃ (0.12 mmol), and HP(tBu)₃.BF₄ (0.24 mmol) are weighed and added into a 250 mL two-neck flask under protection of nitrogen gas. 50 mL of toluene (N₂ is introduced for 15 min in advance to remove oxygen gas) is injected into the two-neck flask, then 3.5 mL of 1M K2CO3

The compounds S2 (2.73 mmol), S9 (5.82 mmol), [Pd$_2$(dba)$_3$].CHCl$_3$ (0.18 mmol), and HP(tBu)$_3$.BF$_4$ (0.36 mmol) are weighed and added into a 250 mL two-neck flask under protection of nitrogen gas. 80 mL of toluene (N$_2$ is introduced for 15 min in advance to remove oxygen gas) is injected into the two-neck flask, then 5 mL of 1M K2CO3 aqueous solution (N$_2$ is introduced for 15 min in advance to remove oxygen gas) is dropwise added, and stirred at room temperature overnight. After the end of the reaction, 35 mL of deionized water is added, and then several droplets of 2M HCl are dripped. Extraction is performed with dichloromethane. The organic phase is collected, and dried with anhydrous Na$_2$SO$_4$. The dried solution is filtered, and the solvent is removed with a rotary evaporator to obtain a crude product. The crude product is purified through a silica-gel chromatographic column to finally obtain a solid H44 (1.72 mmol, 63%).

MALDI-TOF MS: m/z calculated value: C46H28N6O2: 696.2; measured value: 696.3; Elemental analysis calculated value: C, 79.30; H, 4.05; N, 12.06; 0, 4.59; test value: C, 79.33; H, 4.07; N, 12.03; 0, 4.57.

Preparation Example 4 Synthesis of H46

M, 1.98 mmol) is dropwise added into the solution, and this temperature is maintained for 1 h. S10 (4.2 mmol) is dropwise added into a lithiation solution of the above-mentioned S2, and stirred for 1 h at −80° C. The solution is slowly warmed to room temperature, and stirred overnight. A plurality of droplets of anhydrous ethyl alcohol are added, and reduced-pressure distillation is performed to remove the volatile solvent to obtain a crude product. The crude product is dissolved in 50 mL of dichloromethane, and 10 mL of hydrogen peroxide aqueous solution with the mass concentration of 30% is dropwise added into the solution. Stirring is performed at room temperature overnight. Extraction is performed by adopting dichloromethane, and the organic phase is collected. The organic phase is washed with clean water for 3 times. Reduced-pressure distillation is performed to remove the solvent to obtain a crude product. The crude product is refined by using column chromatography (n-hexane:dichloromethane=6:1) to obtain a solid H46 (1.2 mmol, 70%).

Characterization results: MALDI-TOF MS: m/z, calculated value: C48H34N2O2P2: 732.2; test value: 732.4.

Elemental analysis calculated value: C, 78.68; H, 4.68; N, 3.82; 0, 4.37; P, 8.45; test value: C, 78.70; H, 4.71; N, 3.80; 0, 4.36; P, 8.43.

Preparation Example 5 Synthesis of H60

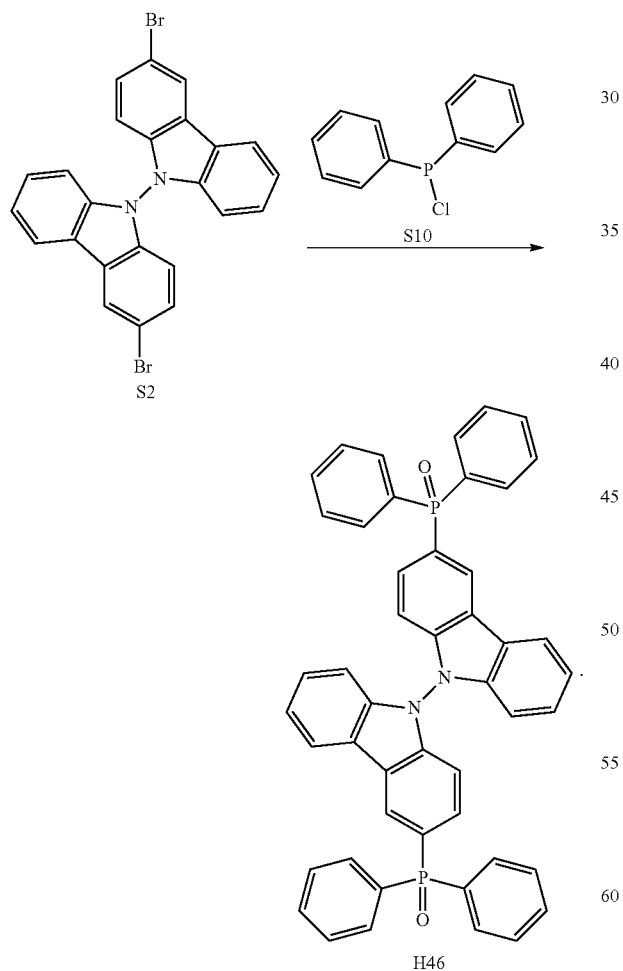

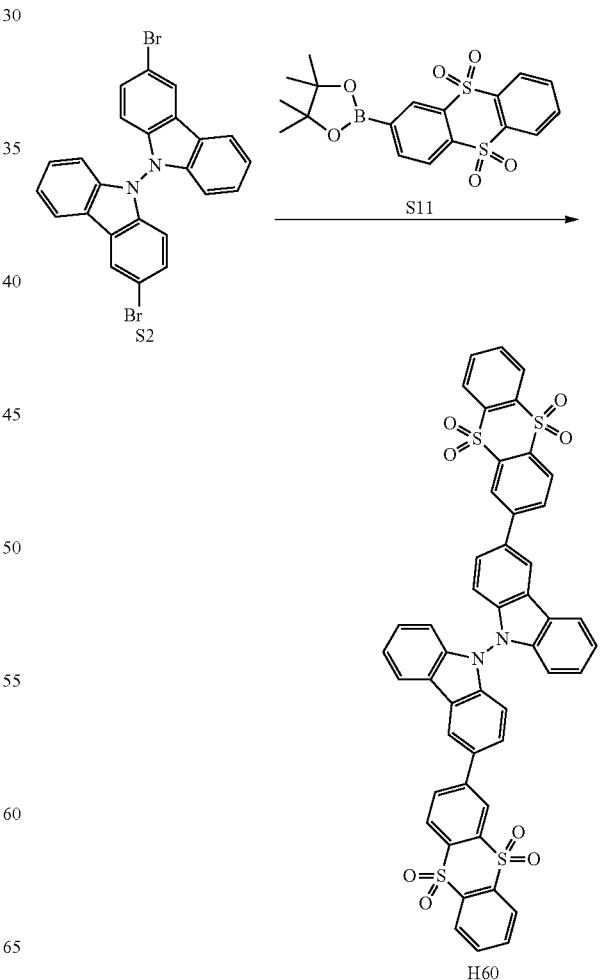

S2 (1.25 g, 1.72 mmol) is weighed and dissolved in 60 mL of anhydrous THE in a nitrogen gas atmosphere, and the solution is cooled to −80° C. 0.8 mL of n-BuLi solution (2.5

The compounds S2 (3.28 mmol), S11 (7.00 mmol), [Pd₂(dba)₃].CHCl₃ (0.22 mmol), and HP(tBu)₃.BF₄ (0.44 mmol) are weighed and added into a 250 mL two-neck flask under protection of nitrogen gas. 100 mL of toluene (N₂ is introduced for 15 min in advance to remove oxygen gas) is injected into the two-neck flask, then 6 mL of 1M K2CO3 aqueous solution (N₂ is introduced for 15 min in advance to remove oxygen gas) is dropwise added, and stirred at room temperature overnight. After the end of the reaction, 50 mL of deionized water is added, and then several droplets of 2M HCl are dripped. Extraction is performed with dichloromethane. The organic phase is collected, and dried with anhydrous Na₂SO₄. The dried solution is filtered, and the solvent is removed with a rotary evaporator to obtain a crude product. The crude product is purified through a silica-gel chromatographic column to finally obtain a solid H60 (2.2 mmol, 67%).

MALDI-TOF MS: m/z calculated value: C48H28N2O8S4: 888.1; measured value: 888.3;

Elemental analysis calculated value: C, 64.85; H, 3.17; N, 3.15; 0, 14.40; S, 14.43; test value: C, 64.88; H, 3.19; N, 3.13; 0, 14.38; S, 14.42.

Preparation Example 6 Synthesis of H79

S4 (2.4 mmol) is dissolved in diethyl ether (150 mL) at −78° C., and a n-hexane solution of n-BuLi (3 mmol) is dropwise added into the solution. The reaction solution is continuously stirred for 2 h, slowly warmed to room temperature, and stirred for 1 h at room temperature. Then, the reaction solution is cooled to −78° C. again, and 45 mL of a toluene solution of S12 (5.8 mmol) is dropwise added under stirring. The solution is slowly warmed to room temperature, and stirred overnight. Reduced-pressure distillation is performed to remove all solvents, and a crude product is collected. The crude product is respectively washed with methanol (3×60 mL) and pentane (3×60 mL), and a crude product is collected again. The crude product is purified through a silica-gel chromatographic column by taking n-hexane:trichloromethane (5:1) as the eluant to finally obtain a solid H79 (1.4 mmol, 58%).

Characterization results: MALDI-TOF MS: m/z, calculated value: C60H40B4N2: 832.4; test value: 832.4.

Elemental analysis calculated value: C, 86.59; H, 4.84; B, 5.20; N, 3.37; test value: C, 86.62; H, 4.85; B, 5.18; N, 3.35.

Other compounds are also obtained by adopting similar synthesis methods.

Performance Test.

Examples 1~8

In view of the compounds H12, H28, H31, H46, H56, H60, H63, and H79, optimization and calculation are performed by using density functional theory (DFT) and utilizing Gaussian 09 program package in B3LYP/6-31G(d) calculation level, to obtain distribution conditions of HOMO and LUMO in molecular frontier orbits; and meantime, singlet energy levels S1 and triplet energy levels T1 of molecules are subjected to analog calculation on the basis of time-dependent density functional theory (TDDFT).

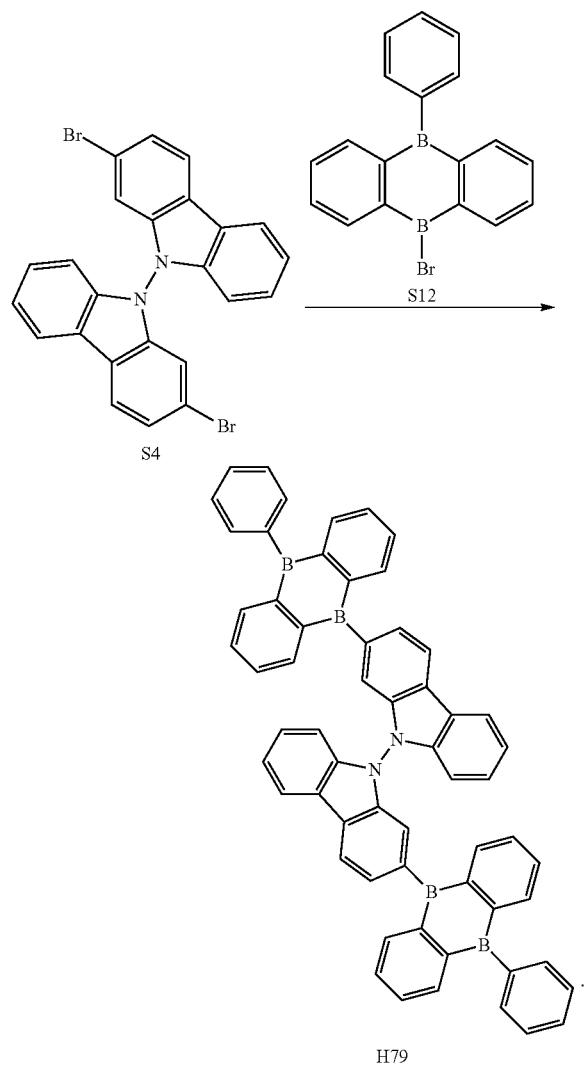

TABLE 1

Related performance data of compounds

| Example | Compound | HOMO (ev) | LUMO (ev) | S₁ (ev) | T₁ (ev) | Eg (ev) |
|---|---|---|---|---|---|---|
| 1 | H12 | −5.35 | −1.95 | 3.42 | 3.12 | 3.27 |
| 2 | H28 | −5.45 | −2.29 | 3.49 | 2.78 | 3.16 |
| 3 | H31 | −5.56 | −2.36 | 3.42 | 2.94 | 3.20 |
| 4 | H46 | −5.63 | −2.24 | 3.62 | 3.15 | 3.39 |
| 5 | H56 | −5.48 | −2.32 | 3.24 | 2.65 | 3.16 |
| 6 | H60 | −5.58 | −2.40 | 3.60 | 2.87 | 3.18 |
| 7 | H63 | −5.46 | −2.52 | 3.48 | 2.96 | 2.94 |
| 8 | H79 | −5.85 | −3.22 | 3.02 | 2.59 | 2.63 |

Related data of the Examples 1~8 are shown in Table 1. It can be seen from Table 1 that, all the compounds have high singlet and triplet energy levels and are suitable for serving as the host material of the luminescent layer. (In Table 1, S₁ represents singlet energy level, T₁ represents triplet energy level, and Eg represents HOMO-LUMO energy level difference).

The organic electroluminescence apparatus provided by the present disclosure is shown in FIG. 1 and includes a substrate 1, an ITO anode 2, a hole injection layer 3, a first hole transport layer 4, a second hole transport layer 5, a luminescent layer 6, a first electron transport layer 7, a second electron transport layer 8, a cathode 9 (a silver electrode), and a cap layer (CPL) 10.

Example 9

The present embodiment provides an organic electroluminescence apparatus, and specific preparation steps are as follows:

1) cutting a glass substrate to a size of 50 mm×50 mm×0.7 mm, subjecting the cut glass substrate to ultrasonic to clean for 30 minutes respectively in acetone, isopropyl alcohol, and deionized water, and then cleaning the glass substrate for 30 minutes in the presence of UV ozone. Mounting the obtained glass substrate with an indium tin oxide (ITO) anode on a vacuum evaporation equipment;

2) evaporating a hole injection layer material compound 1 on the ITO anode layer 2 through vacuum evaporation, and the obtained layer has a thickness of 10 nm and is used as a hole injection layer 3;

3) vacuum evaporating a hole transport layer material compound 2 on the hole injection layer 3, and the obtained layer has a thickness of 100 nm and is used as a first hole transport layer 4;

4) vacuum evaporating a hole transport type material compound 3 on the first hole transport layer 4, and the obtained layer has a thickness of 10 nm and is used as a second hole transport layer 5;

5) a luminescent layer 6 on the second hole transport layer 5, and the compound H12 is used as the host material, the compound 4 is used as the doping material, the doping ratio is 3% (a mass ratio), and the thickness is 30 nm;

6) vacuum evaporating an electron transport type material compound 5 on the luminescent layer 6, and the obtained layer has a thickness of 10 nm and is used as a first electron transport layer 7;

7) vacuum evaporating an electron transport material compound 6 on the first electron transport layer 7, and the obtained layer has a thickness of 30 nm and is used as a second electron transport layer 8;

8) vacuum evaporating a silver electrode on the second electron transport layer 8 through vacuum evaporation, and the silver electrode has a thickness of 15 nm and is used as a cathode 9; and 9) vacuum evaporating the hole transport layer material compound 2 on the cathode 9, and the obtained layer has a thickness of 80 nm and is used as a cap layer 10.

Compound 1

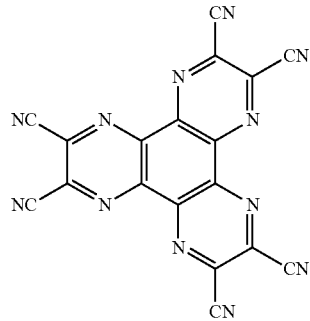

Compound 2

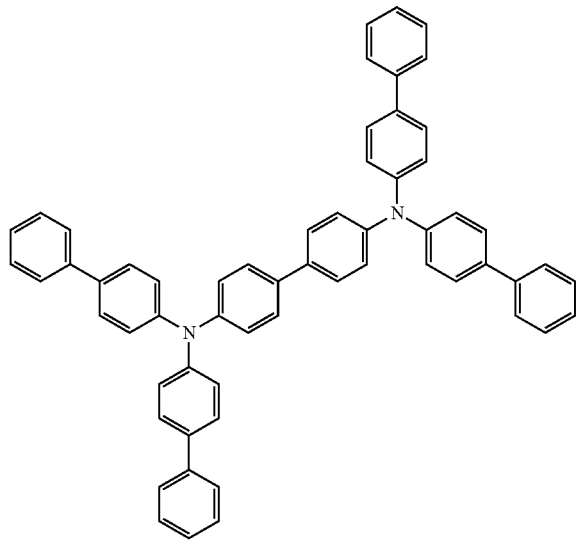

Compound 3

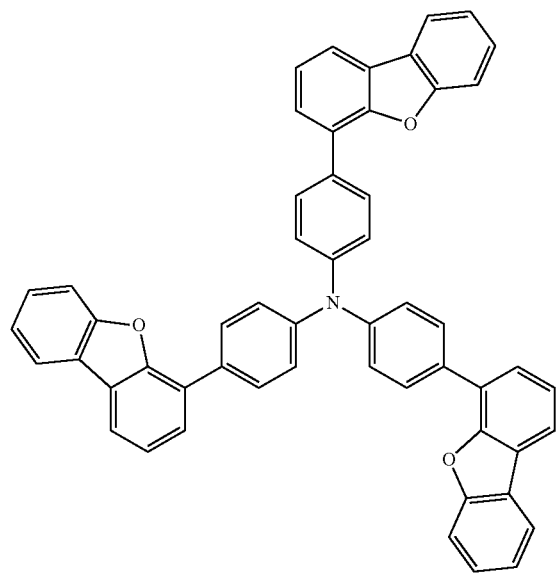

Comparative Compound 1

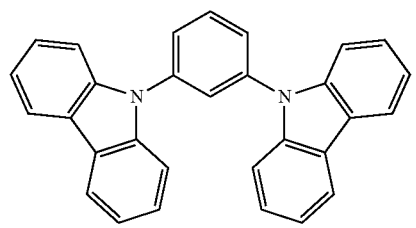

-continued

Compound 4

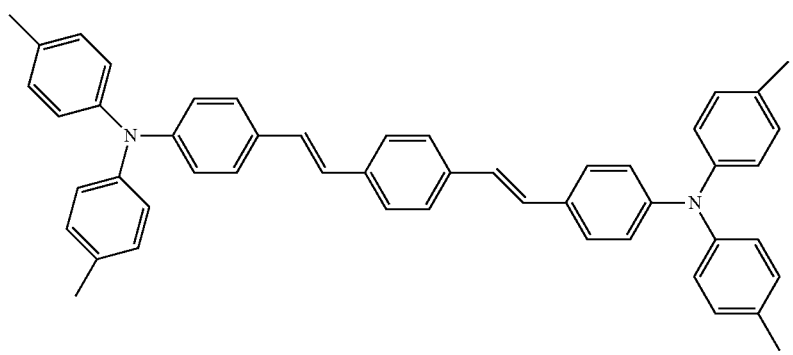

Compound 5

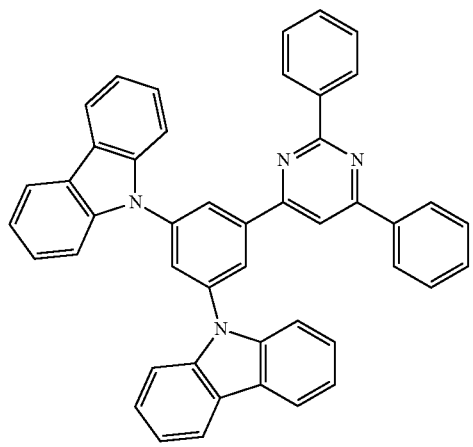

Compound 6

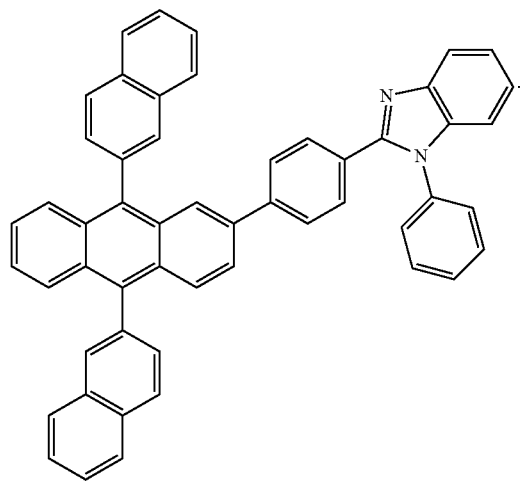

Example 10

The difference from the example 9 lies in that the compound H12 is replaced with H28.

Example 11

The difference from the example 9 lies in that the compound H12 is replaced with H31.

Example 12

The difference from the example 9 lies in that the compound H12 is replaced with H46.

Example 13

The difference from the example 9 lies in that the compound H12 is replaced with H56.

Example 14

The difference from the example 9 lies in that the compound H12 is replaced with H60.

Example 15

The difference from the example 9 lies in that the compound H12 is replaced with H63.

Example 16

The difference from the example 9 lies in that the compound H12 is replaced with H79.

Example 17

The difference from the example 9 lies in that the compound 4 is replaced with green material Ir(ppy)3.

Example 18

The difference from the example 9 lies in that the compound H12 is replaced with H28, and the compound 4 is replaced with green luminescent material Ir(ppy)3.

Example 19

The difference from the example 9 lies in that the compound H12 is replaced with H31, and the compound 4 is replaced with green luminescent material Ir(ppy)3.

Example 20

The difference from the example 9 lies in that the compound H12 is replaced with H60, and the compound 4 is replaced with green luminescent material Ir(ppy)3.

Example 21

The difference from the example 9 lies in that the compound H12 is replaced with H63, and the compound 4 is replaced with green luminescent material Ir(ppy)3.

Comparative Example 1

The difference from the example 9 lies in that the compound H12 is replaced with the comparative compound 1.

Comparative Example 2

The difference from the example 9 lies in that the compound H12 is replaced with the comparative compound 1, and the compound 4 is replaced with green luminescent material Ir(ppy)3.

Performance parameter results of the examples 9~21 and the comparative examples 1~2 are shown in Table 2.

TABLE 2

| Apparatus | Host material | Guest material | $V_{on}$ [V] | $CE_{(10mA/cm^2)}$ (cd A$^{-1}$) |
| --- | --- | --- | --- | --- |
| Example 9 | H12 | Compound 4 | 3.42 | 5.83 |
| Example 10 | H28 | Compound 4 | 3.56 | 5.92 |
| Example 11 | H31 | Compound 4 | 3.63 | 5.48 |
| Example 12 | H46 | Compound 4 | 3.58 | 5.82 |
| Example 13 | H56 | Compound 4 | 3.72 | 5.76 |
| Example 14 | H60 | Compound 4 | 3.75 | 5.34 |
| Example 15 | H63 | Compound 4 | 3.65 | 5.67 |
| Example 16 | H79 | Compound 4 | 3.78 | 5.45 |
| Example 17 | H12 | Ir(ppy)3 | 4.12 | 107.9 |
| Example 18 | H31 | Ir(ppy)3 | 4.16 | 104.3 |
| Example 19 | H56 | Ir(ppy)3 | 4.13 | 112.7 |
| Example 20 | H63 | Ir(ppy)3 | 4.09 | 115.3 |
| Example 21 | H79 | Ir(ppy)3 | 4.18 | 110.5 |
| Comparative Example 1 | Comparative compound 1 | Compound 4 | 3.95 | 4.82 |
| Comparative Example 2 | Comparative compound 1 | Ir(ppy)3 | 4.35 | 95.6 |

It can be seen from Table 2 that, when the blue luminescent material compound 4 is used as the guest material of the luminescent layer, compared with the comparative compound 1 as the host material, the compound provided by the present disclosure as the host material has the advantages that the obtained organic electroluminescence apparatus has lower driving voltage and higher luminous efficiency, which is mainly benefited from that the host material of the present disclosure has higher triplet energy level and good bipolar transmission performance.

When the green luminescent material compound Ir(ppy)3 is used as the guest material of the luminescent layer, compared with the comparative compound 1 as the host material, the compound provided by the present disclosure as the host material has the advantages that it is improved in terms of driving voltage and luminous efficiency, which is mainly benefited from that the host material of the present disclosure has a higher triplet energy level and good bipolar transmission performance.

What is claimed is:

1. A compound, wherein the compound has a structure represented by Formula (I):

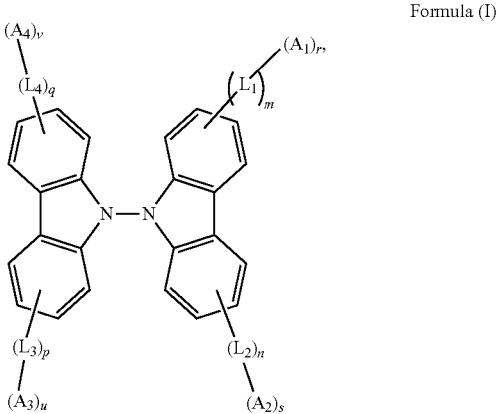

Formula (I)

wherein, m, n, p, q, r, s, u, and v are each independently selected from 0 or 1, at least one of r and s is 1, at least one of u and v is 1, $L_1$, $L_2$, $L_3$, and $L_4$ are each independently selected from substituted or unsubstituted C6-C40 aryl, or substituted or unsubstituted C3-C40 heterocyclyl, and $A_1$, $A_2$, $A_3$, and $A_4$ are each independently selected from an electron acceptor unit.

2. The compound according to claim 1, wherein r and u are selected from 1, and s and v are selected from 0.

3. The compound according to claim 1, wherein r, s, u, and v are all selected from 1.

4. The compound according to claim 1, wherein the C6-C40 aryl is selected from one or more of phenyl, biphenyl, terphenyl, naphthyl, binaphthyl, anthryl, bianthryl, diphenylanthryl, benzodihydroanthryl, phenanthryl, dihydrophenanthryl, triphenylene, pyrenyl, fluorenyl, difluorenyl, fluoranthenyl, indenofluorenyl, cyclopentanophenanthryl, spirofluorenyl, benzofluorenyl, indenoanthryl, dibenzofluorenyl, naphthoanthryl, and benzoanthryl; or the C3-C40 heterocyclyl is selected from one or more of thienyl, thiazolyl, pyridyl, furyl, pyranyl, pyrrolyl, pyrazolyl, imidazolyl, oxazolyl, oxadiazolyl, triazolyl, thiadiazolyl, pyridazinyl, pyrimidinyl, pyrazinyl, triazinyl, benzofuranyl, dibenzofuranyl, benzothienyl, dibenzothienyl, phenoxazinyl, phenazinyl, phenothiazinyl, thiaoxazinyl, thianthrenyl, indolyl, benzimidazolyl, benzothiazolyl, purinyl, quinolyl, isoquinolyl, quinoxalyl, and phenanthrolinyl.

5. The compound according to claim 1, wherein $A_1$, $A_2$, $A_3$, and $A_4$ are each independently selected from any one or more of a nitrogen-containing heterocyclic substituent, a cyano substituent, a triaryl boron substituent, a benzophenone substituent, an aromatic heterocyclic ketone substituent, and a sulfone substituent.

6. The compound according to claim 5, wherein the nitrogen-containing heterocyclic substituent is selected from any one or more of structures below:

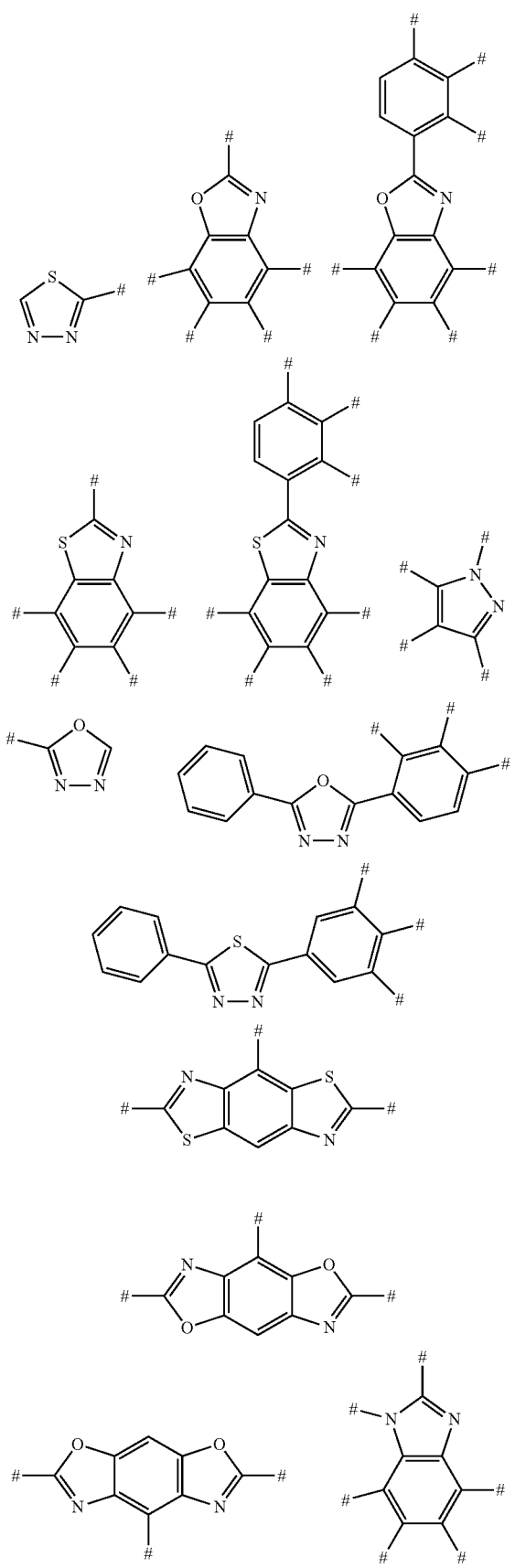
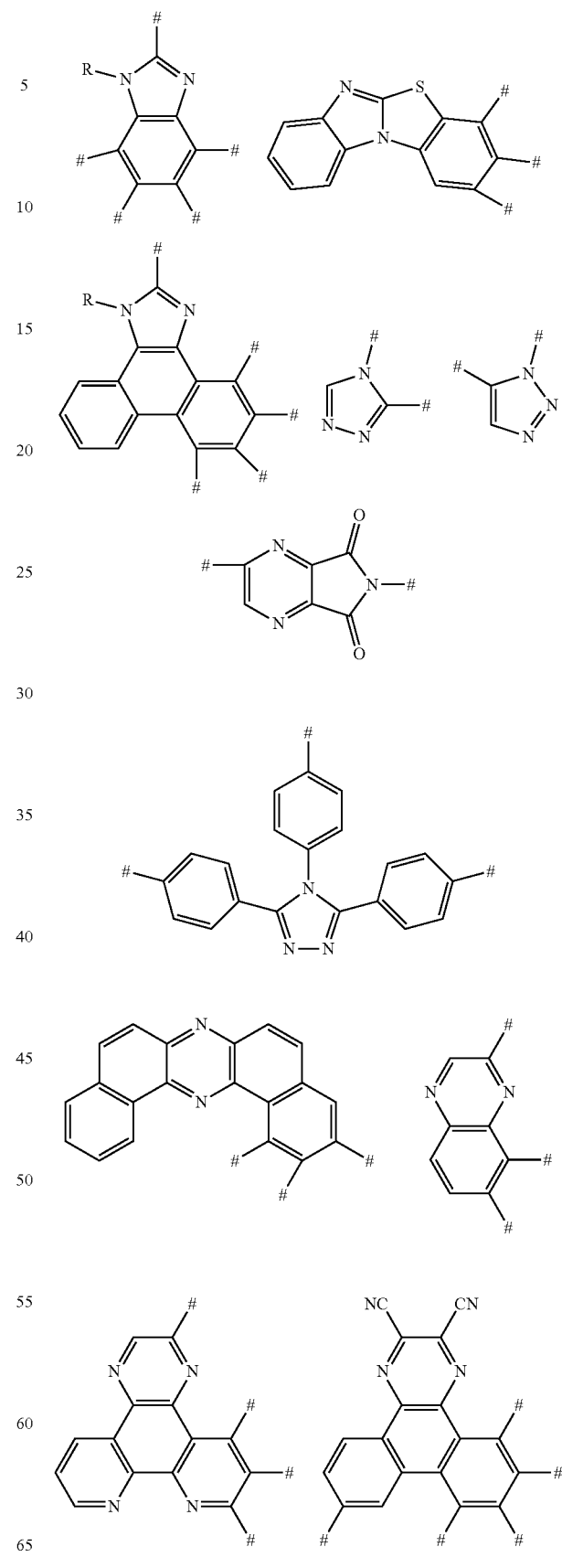

-continued
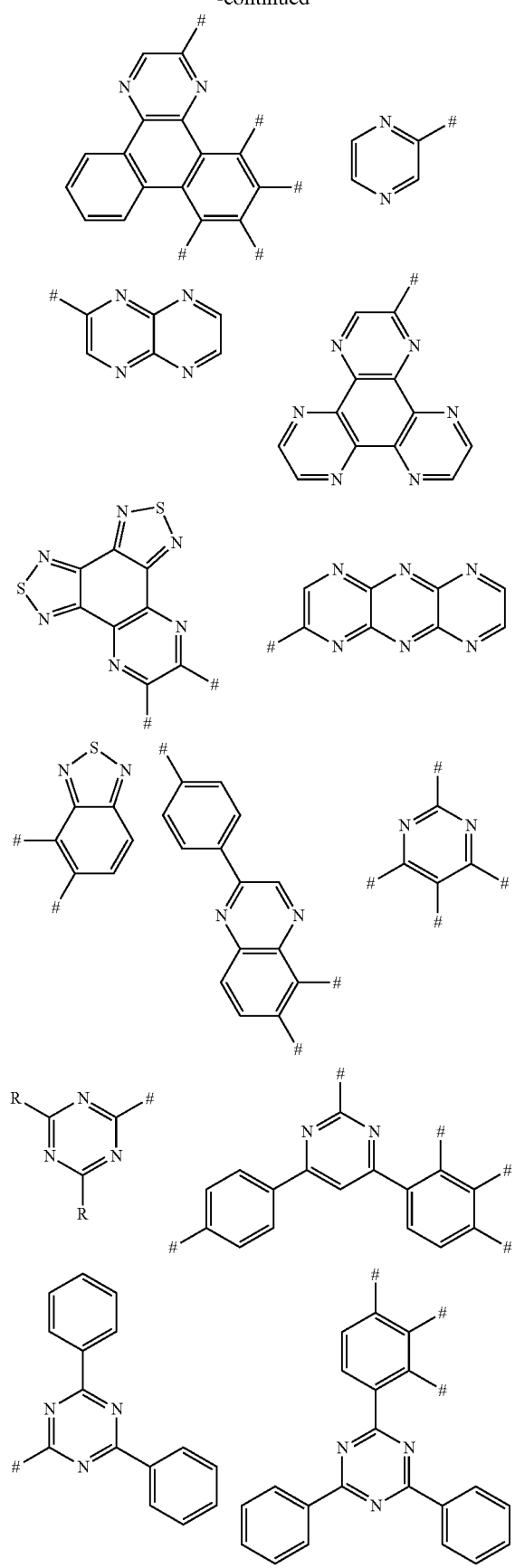
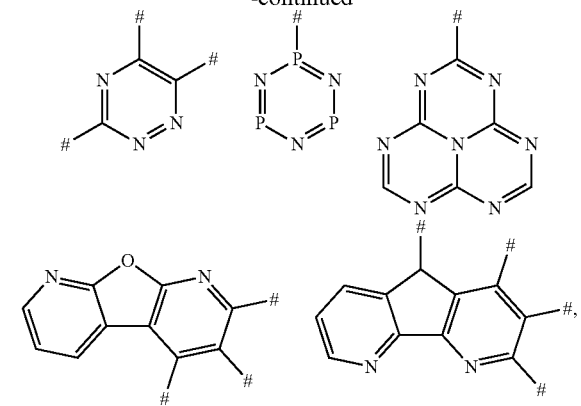
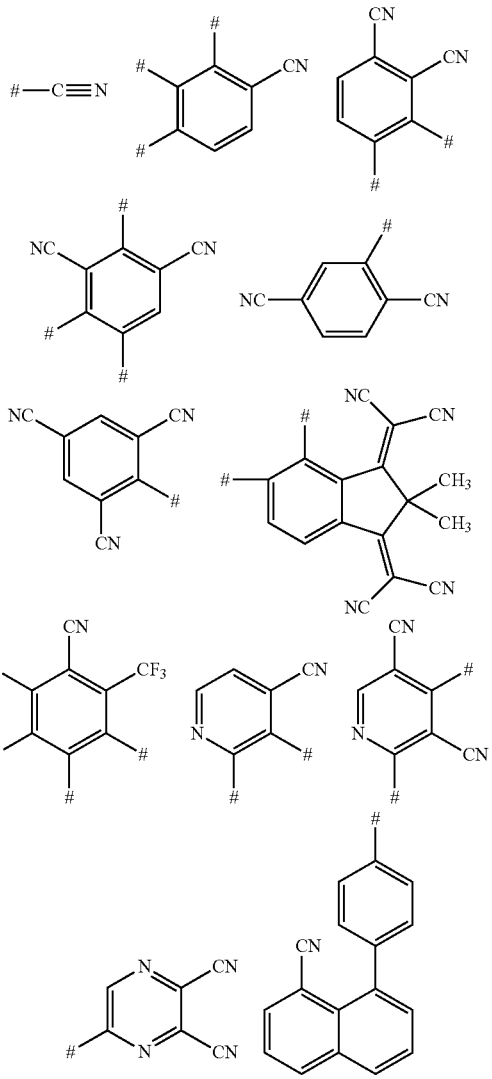
wherein, # represents a connection position; and R is selected from a group of a hydrogen atom, C1-20 alkyl, C1-20 alkoxy, C4-8 cycloalkyl, C6-40 aryl, and C4-40 heteroaryl.
7. The compound according to claim 5, wherein the cyano substituent is selected from one or more of structures below:

-continued

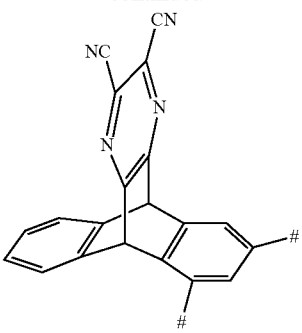

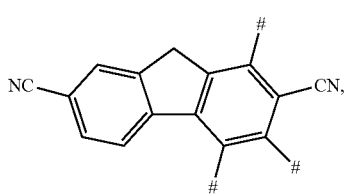

wherein, # represents a connection position.

8. The compound according to claim 5, wherein the aryl boron substituent is selected from one or more of structures below:

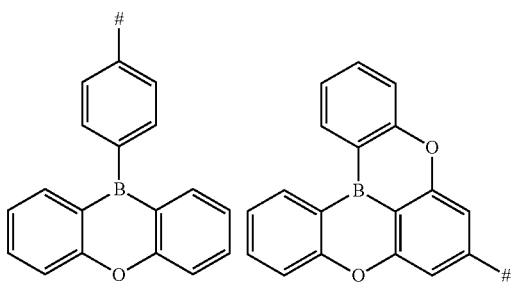

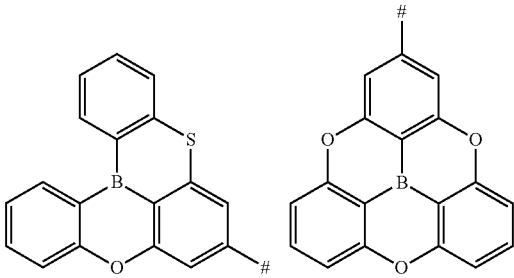

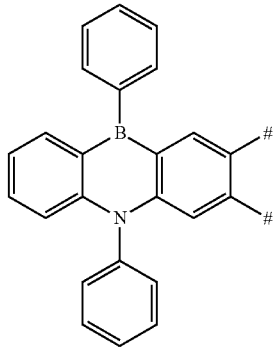

-continued

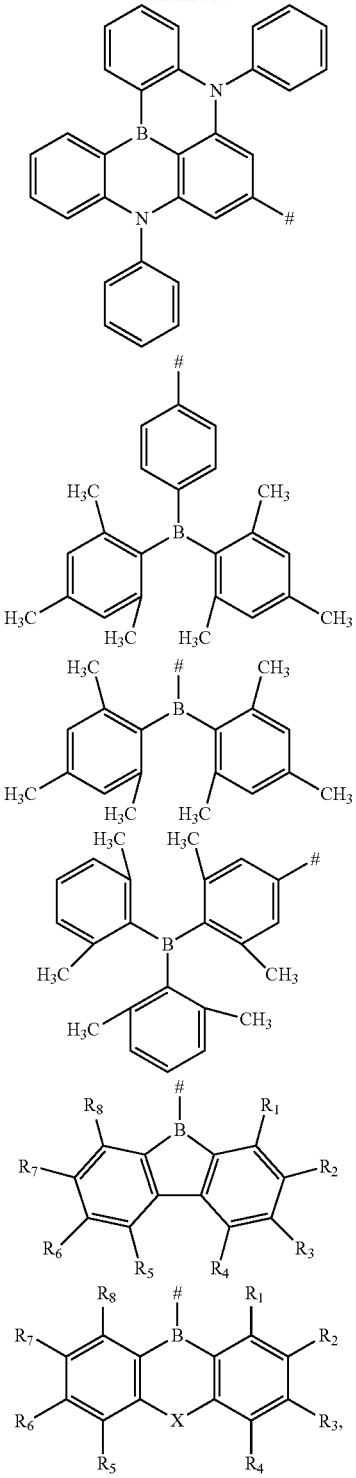

wherein, # represents a connection position; X is selected from a group of $BR_9$, O, S, or $NR_9$; and $R_1$-$R_9$ are each independently selected from C1-20 alkyl, C1-20 alkoxy, C6-40 aryl, and C4-40 heteroaryl.

9. The compound according to claim 5, wherein the aryl ketone substituent and the aromatic heterocyclic ketone substituent are selected from one or more of structures below:

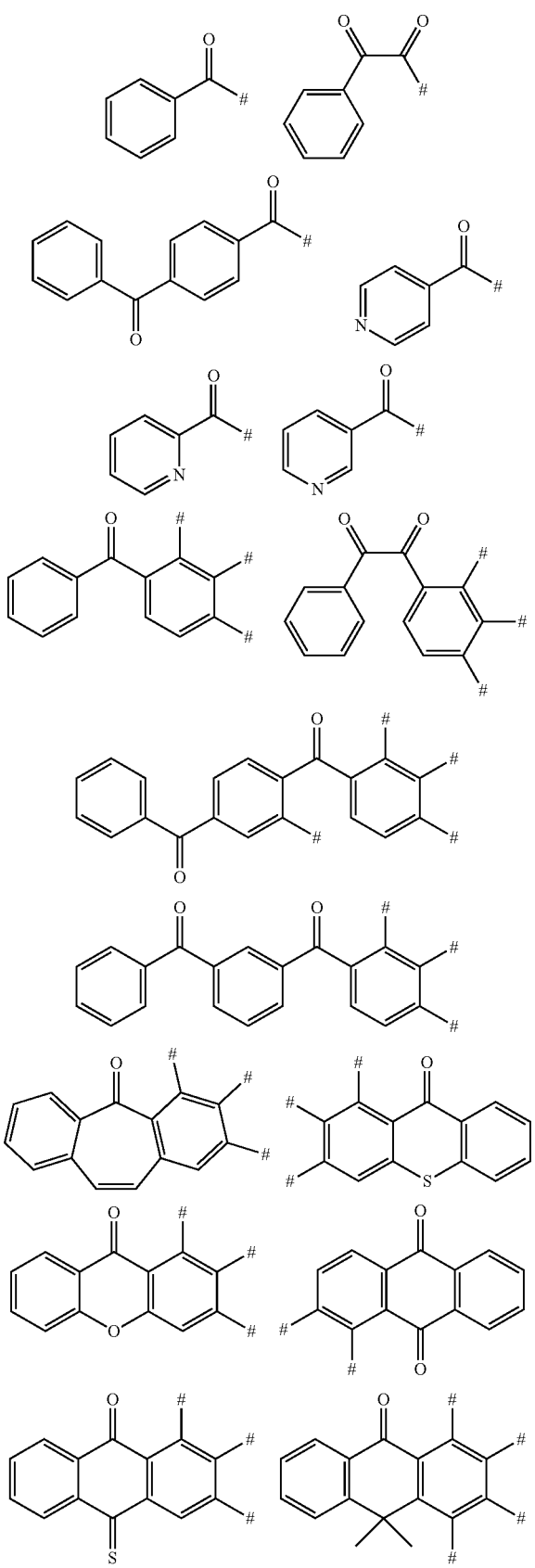
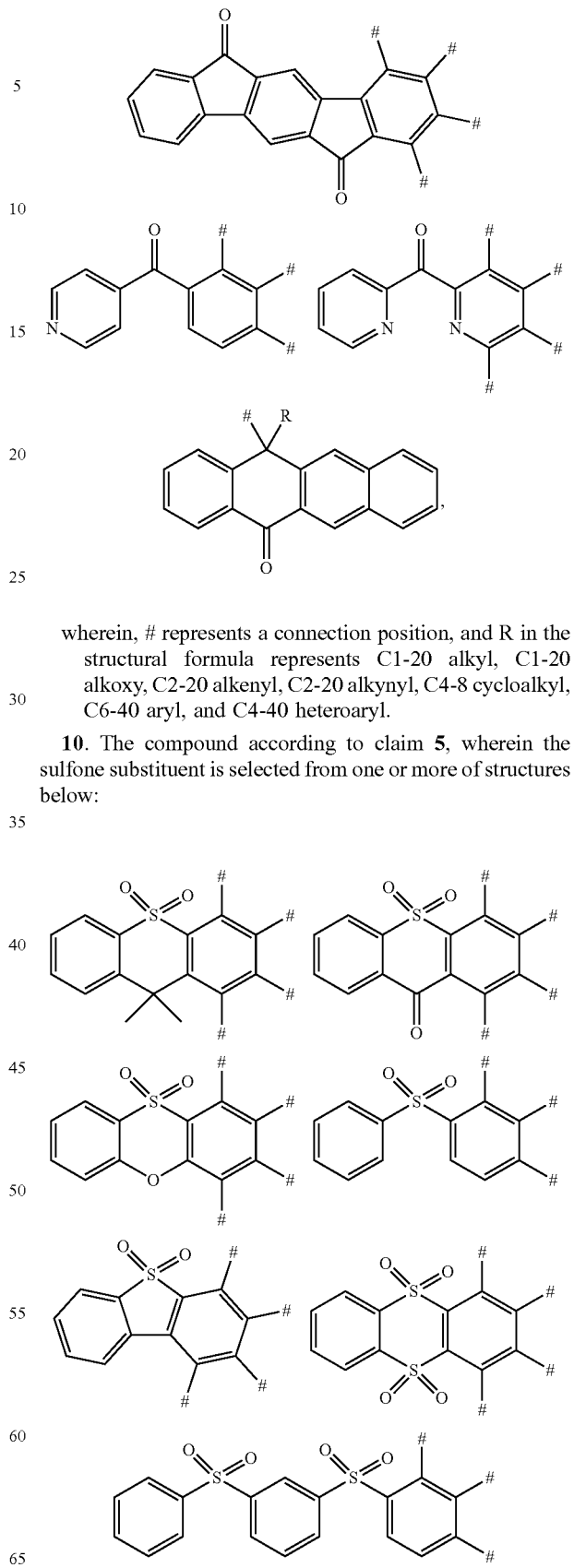
wherein, # represents a connection position, and R in the structural formula represents C1-20 alkyl, C1-20 alkoxy, C2-20 alkenyl, C2-20 alkynyl, C4-8 cycloalkyl, C6-40 aryl, and C4-40 heteroaryl.
10. The compound according to claim 5, wherein the sulfone substituent is selected from one or more of structures below:

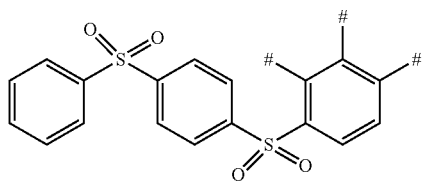

wherein, # represents a connection position.

11. The compound according to claim 5, wherein $A_1$, $A_2$, $A_3$ and $A_4$ are each independently selected from one or more of structures below:

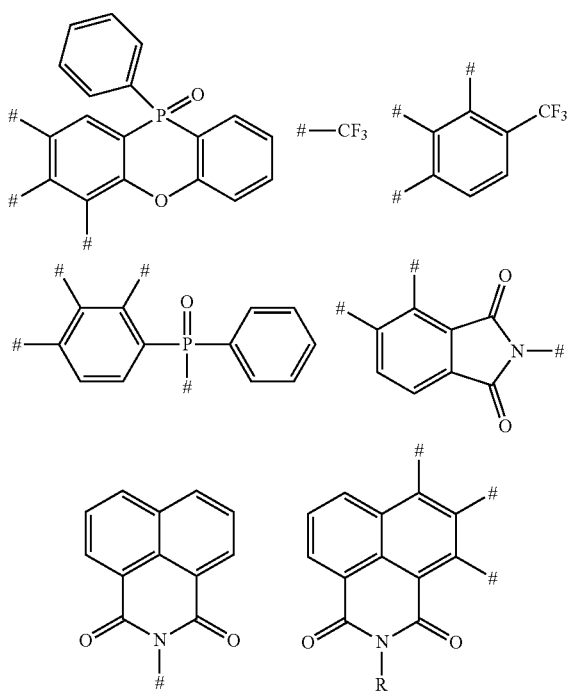

wherein, # represents a connection position, and R in each structural formula each independently represents C1-20 alkyl, C1-20 alkoxy, C2-20 alkenyl, C2-20 alkynyl, C4-8 cycloalkyl, C6-40 aryl, and C4-40 heteroaryl.

12. The compound according to claim 2, wherein the C6-C40 aryl is selected from one or more of phenyl, biphenyl, terphenyl, naphthyl, binaphthyl, anthryl, bianthryl, diphenylanthryl, benzodihydroanthryl, phenanthryl, dihydrophenanthryl, triphenylene, pyrenyl, fluorenyl, difluorenyl, fluoranthenyl, indenofluorenyl, cyclopentanophenanthryl, spirofluorenyl, benzofluorenyl, indenoanthryl, dibenzofluorenyl, naphthoanthryl, and benzoanthryl; and the C3-C40 heterocyclyl is selected from one or more of thienyl, thiazolyl, pyridyl, furyl, pyranyl, pyrrolyl, pyrazolyl, imidazolyl, oxazolyl, oxadiazolyl, triazolyl, thiadiazolyl, pyridazinyl, pyrimidinyl, pyrazinyl, triazinyl, benzofuranyl, dibenzofuranyl, benzothienyl, dibenzothienyl, phenoxazinyl, phenazinyl, phenothiazinyl, thiaoxazinyl, thiaanthryl, indolyl, benzimidazolyl, benzothiazolyl, purinyl, quinolyl, isoquinolyl, quinoxalyl, and phenanthrolinyl.

13. The compound according to claim 2, wherein $A_1$, $A_2$, $A_3$, and $A_4$ are each independently selected from one or more of structures below:

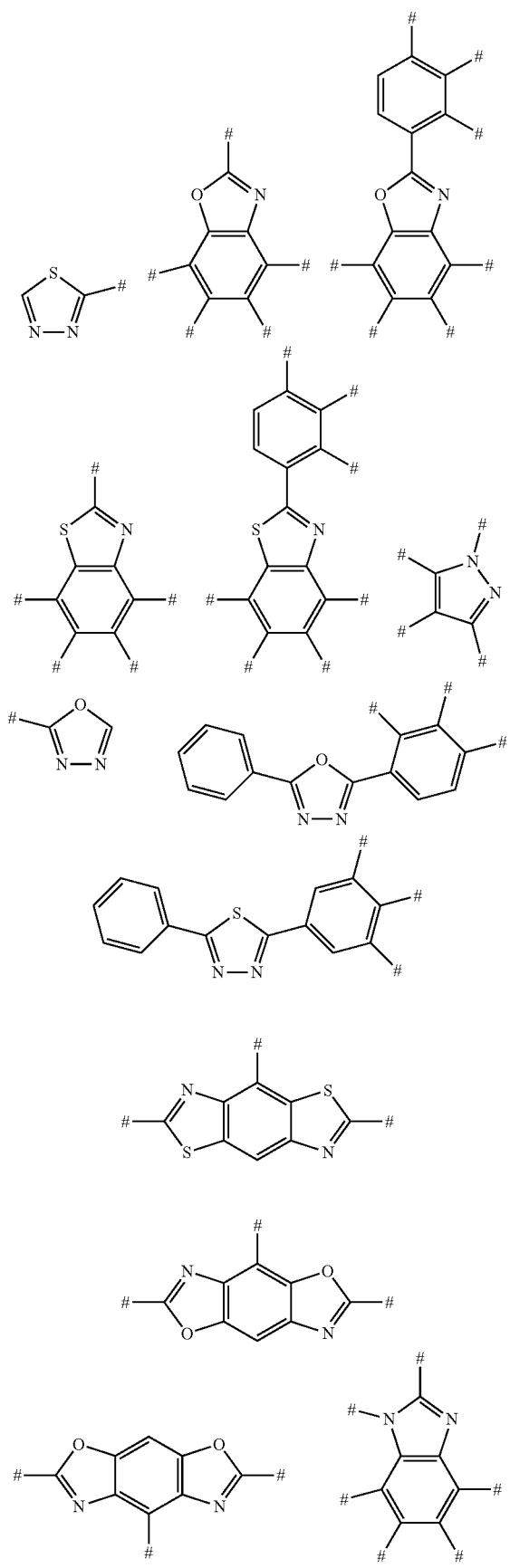
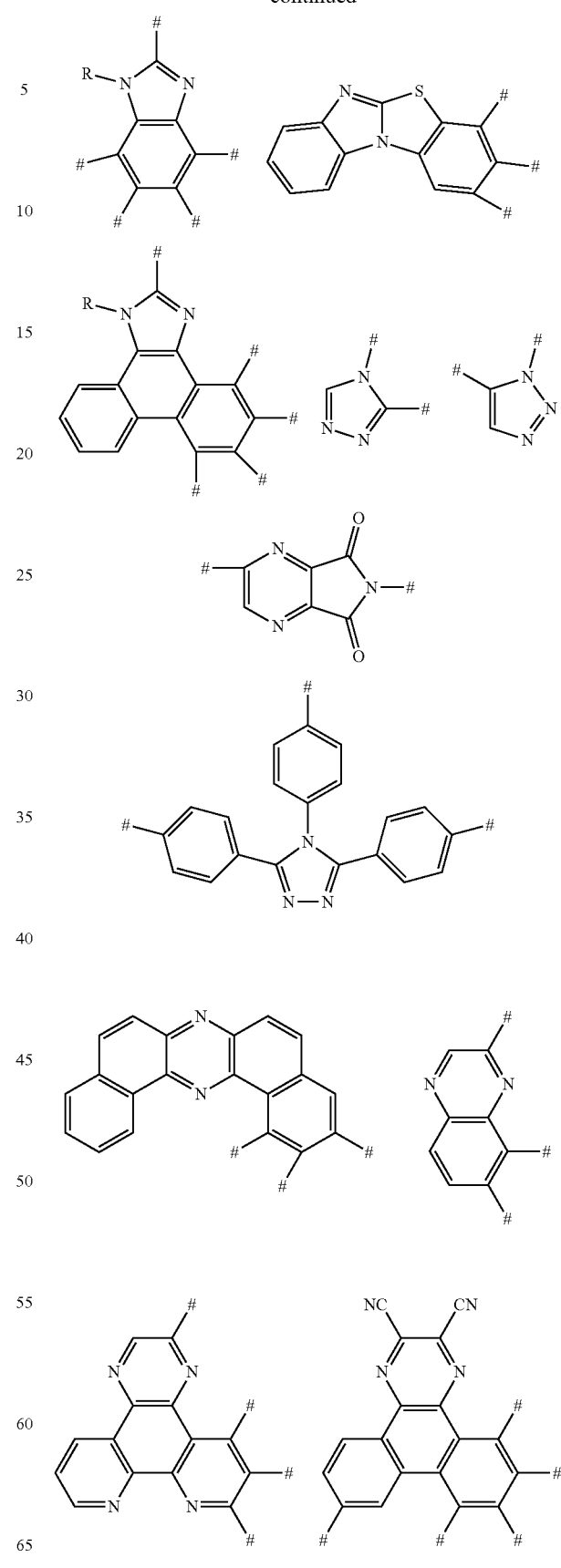

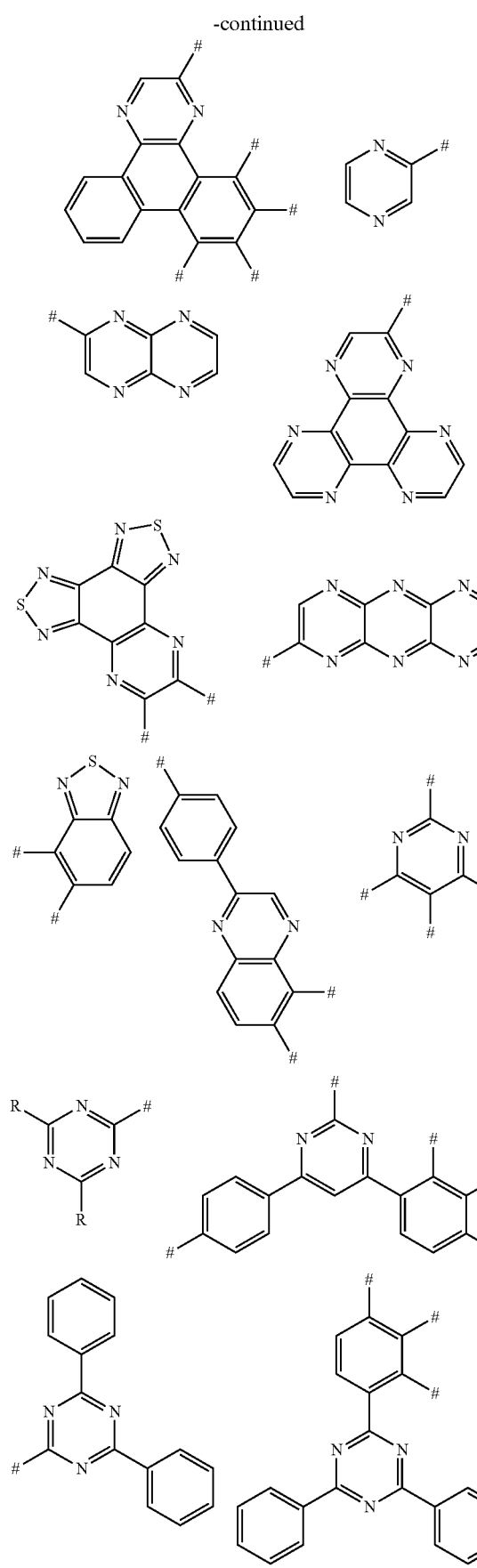
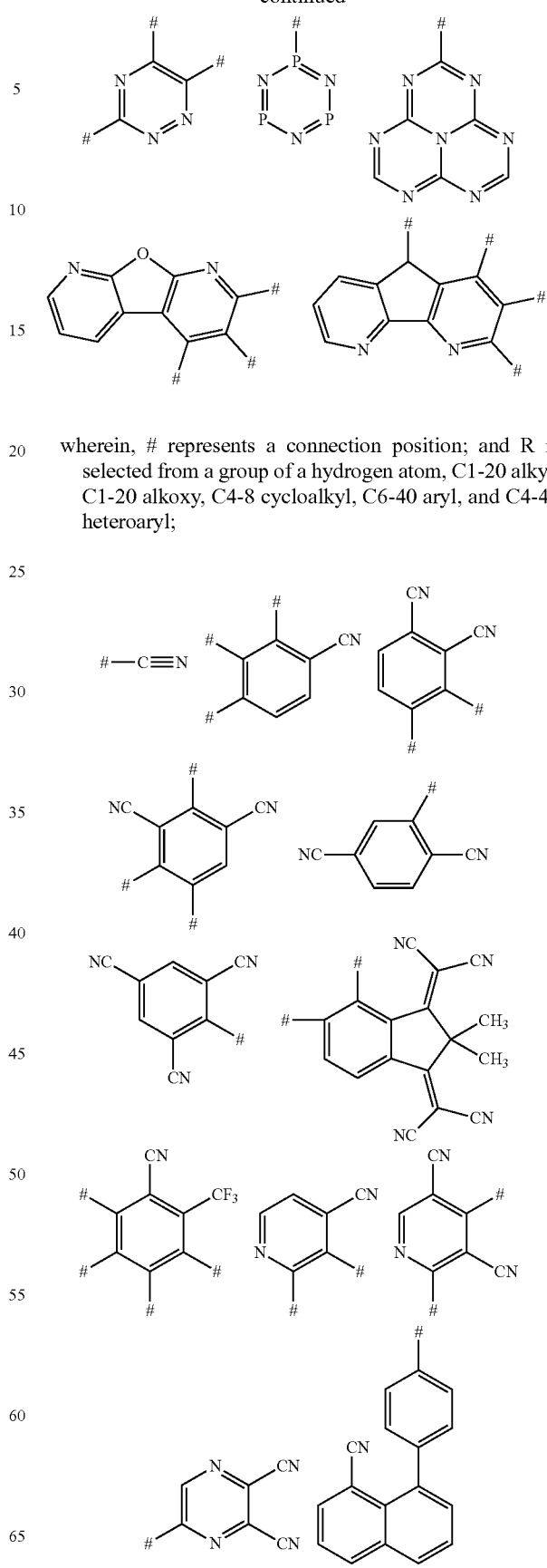
wherein, # represents a connection position; and R is selected from a group of a hydrogen atom, C1-20 alkyl, C1-20 alkoxy, C4-8 cycloalkyl, C6-40 aryl, and C4-40 heteroaryl;

-continued
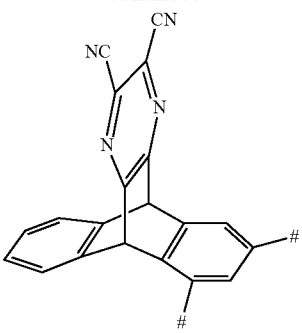
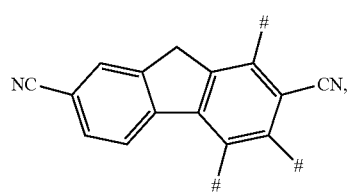
wherein, # represents a connection position;
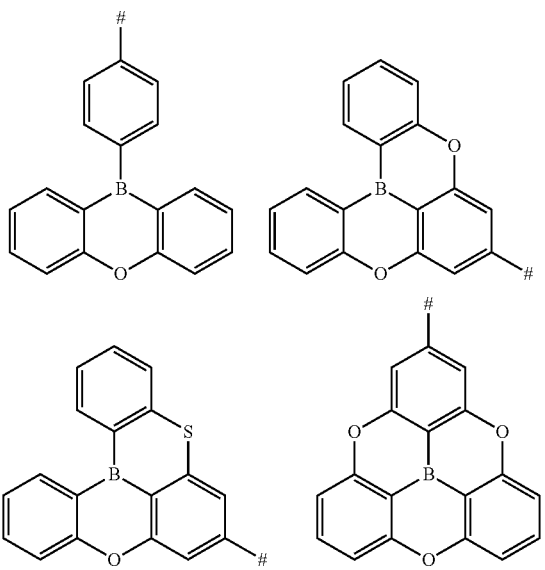
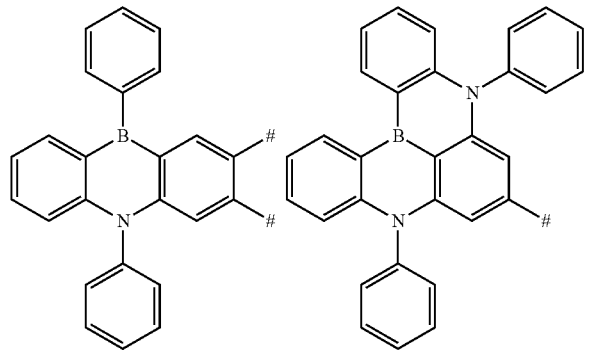
-continued
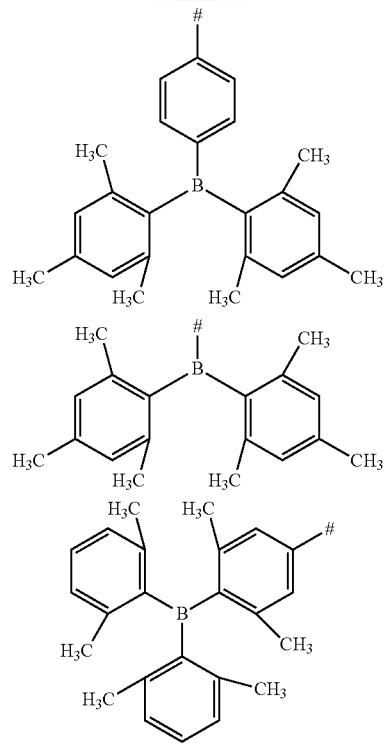
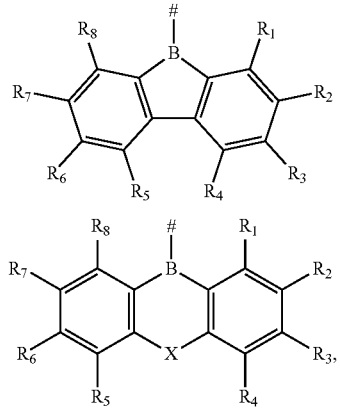
wherein, # represents a connection position; X is selected from BR$_9$, O, S, or NR$_9$; and R$_1$-R$_9$ are each independently selected from a group of C1-20 alkyl, C1-20 alkoxy, C6-40 aryl, and C4-40 heteroaryl;
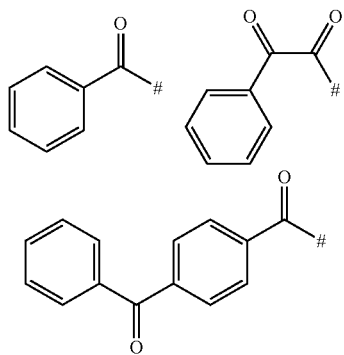

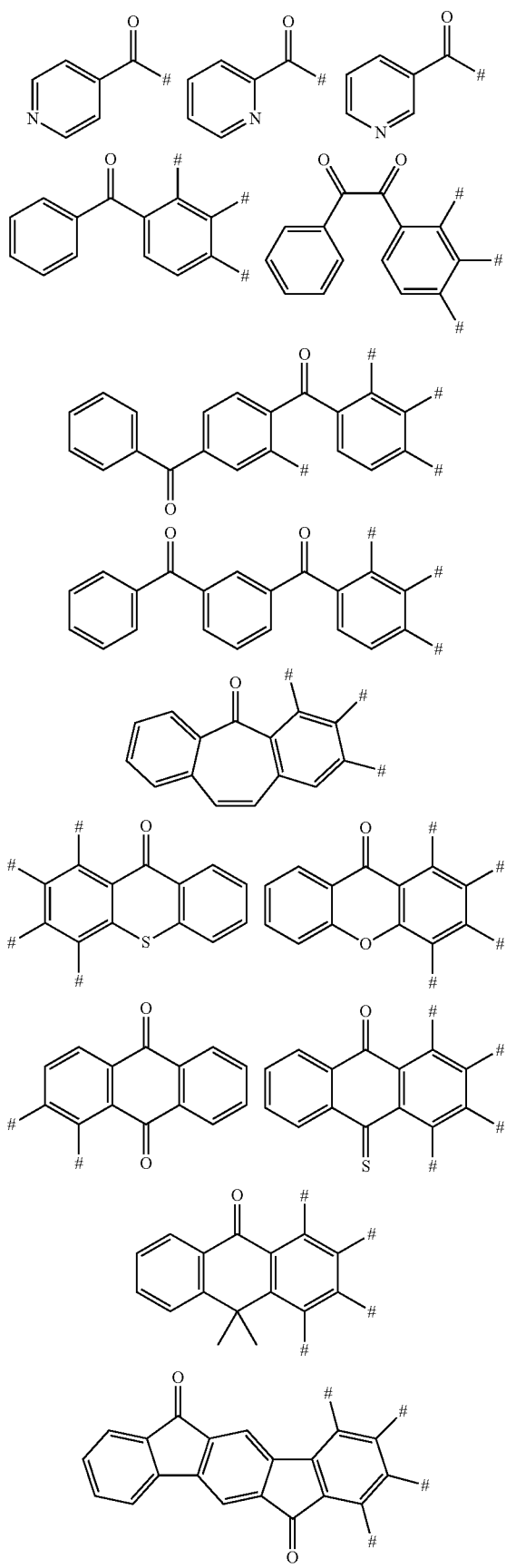
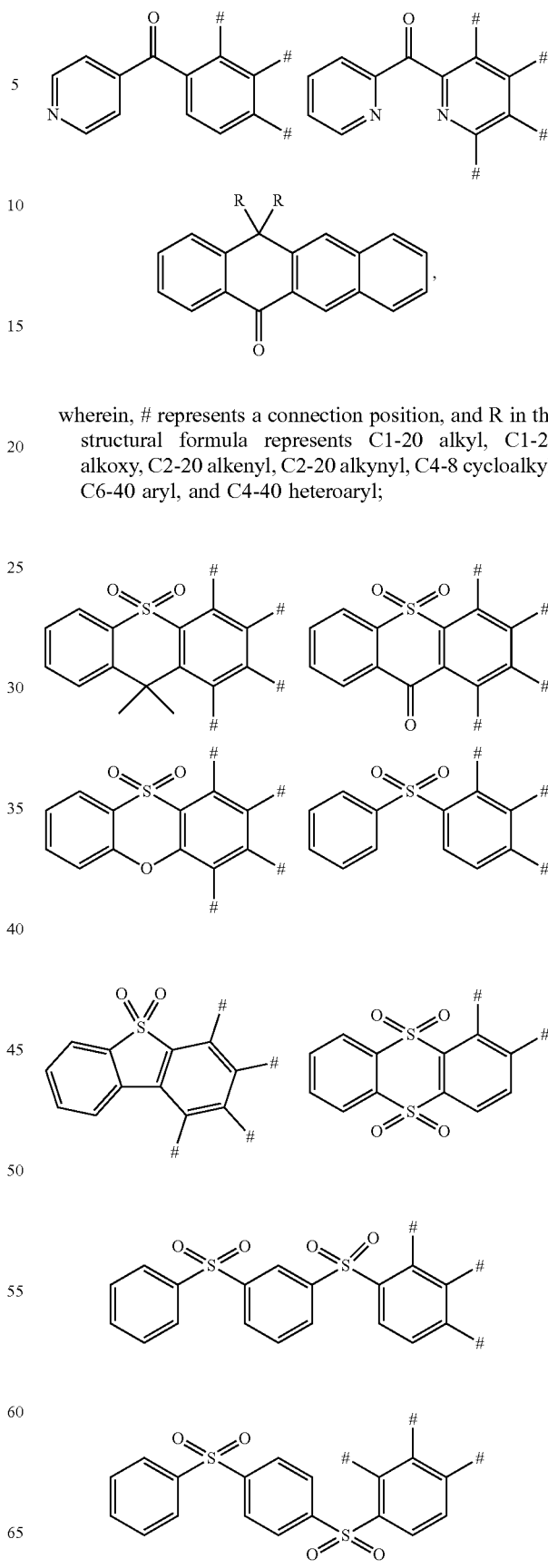
wherein, # represents a connection position, and R in the structural formula represents C1-20 alkyl, C1-20 alkoxy, C2-20 alkenyl, C2-20 alkynyl, C4-8 cycloalkyl, C6-40 aryl, and C4-40 heteroaryl;

97
-continued

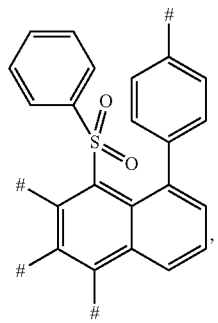

wherein, # represents a connection position;

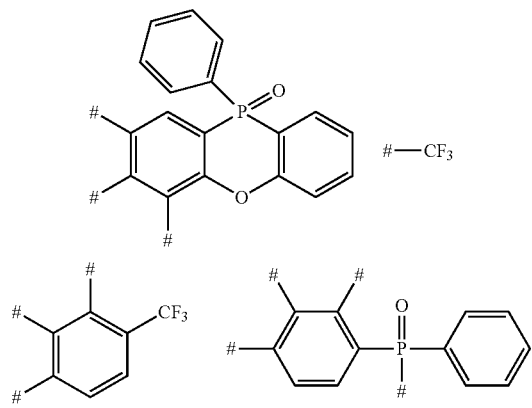

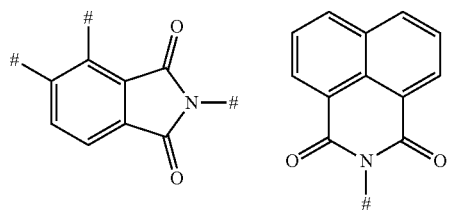

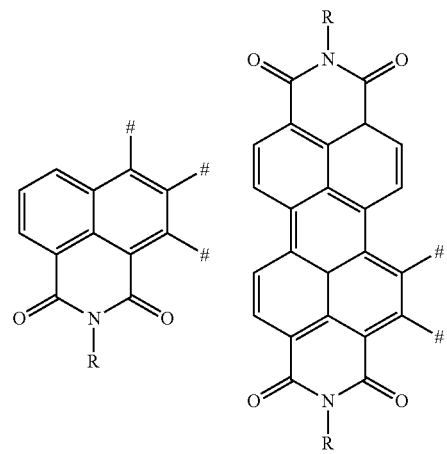

98
-continued

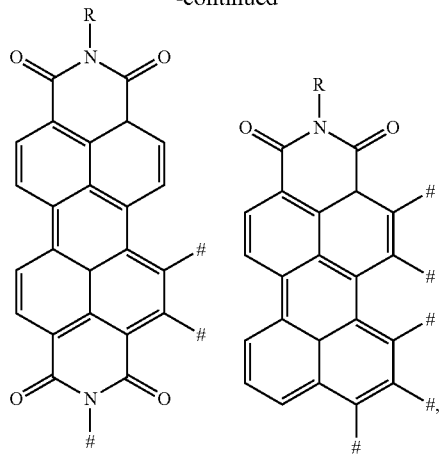

wherein, # represents a connection position, and R in each structural formula each independently represents C1-20 alkyl, C1-20 alkoxy, C2-20 alkenyl, C2-20 alkynyl, C4-8 cycloalkyl, C6-40 aryl, and C4-40 heteroaryl.

14. The compound according to claim 3, wherein the C6-C40 aryl is selected from a group of phenyl; and the C6-C40 heterocyclyl is selected from one or more of thienyl, thiazolyl, pyridyl, furyl, pyranyl, pyrrolyl, pyrazolyl, imidazolyl, oxazolyl, oxadiazolyl, triazolyl, thiadiazolyl, pyridazinyl, pyrimidinyl, pyrazinyl, and triazinyl.

15. The compound according to claim 3, wherein $A_1$, $A_2$, $A_3$, and $A_4$ are each independently selected from one or more of

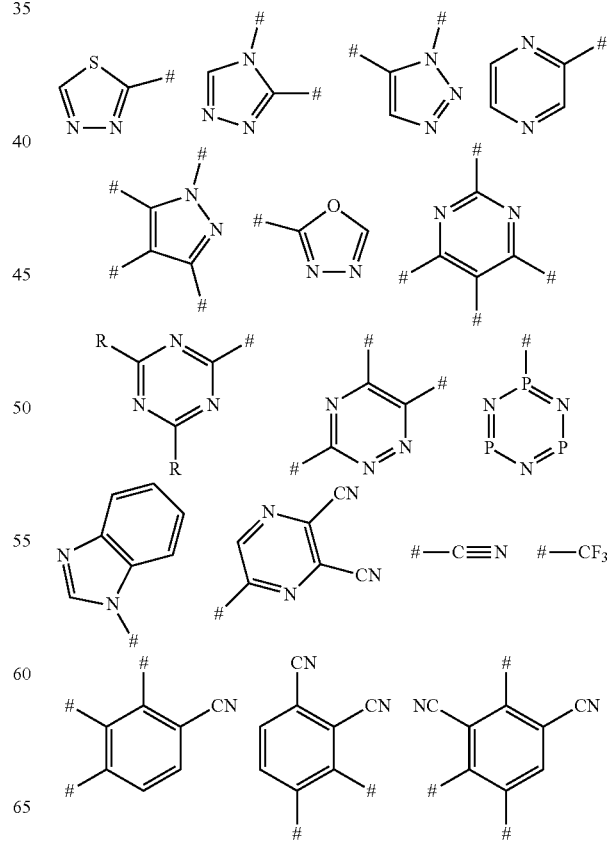

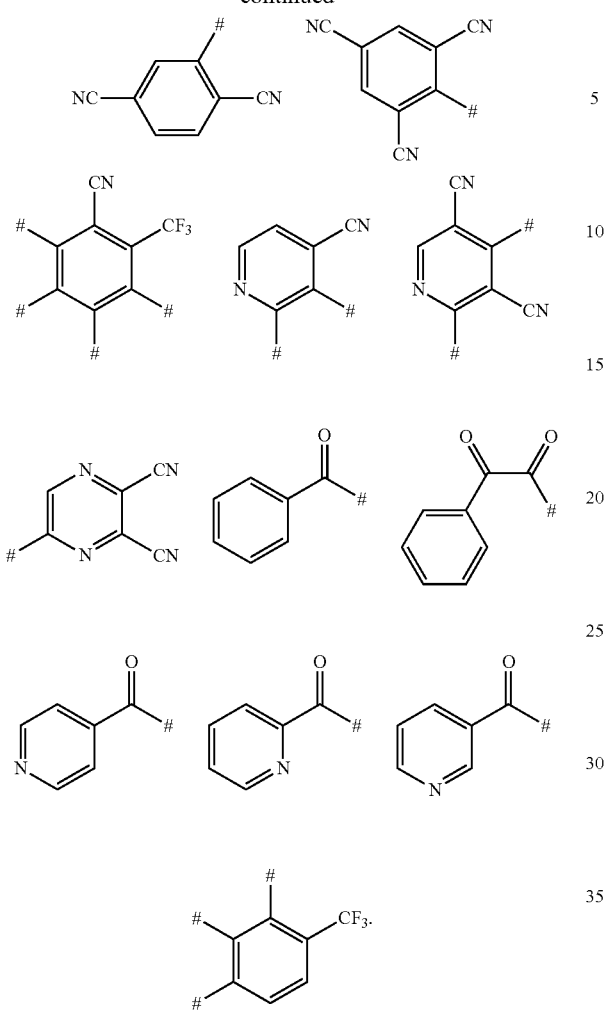
16. The compound according to claim 1, wherein the compound is selected from
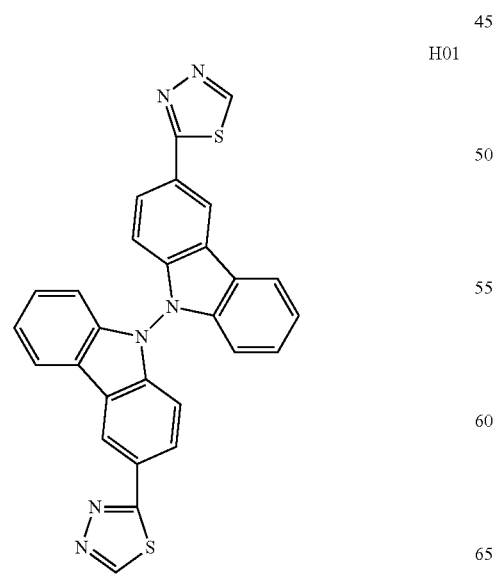
H01
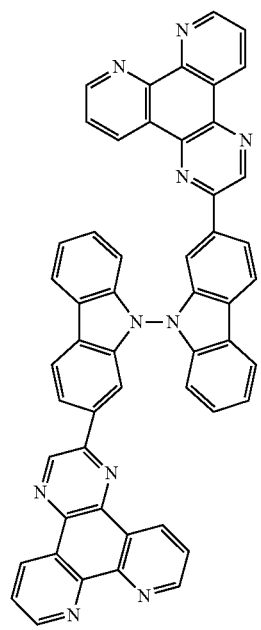
H02
H03

101
-continued
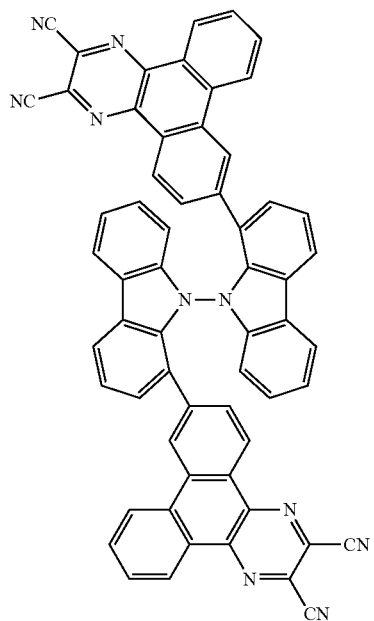
H04
102
-continued
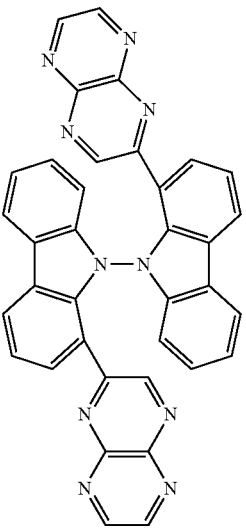
H06
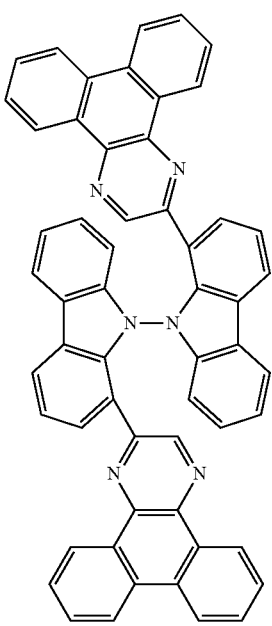
H05
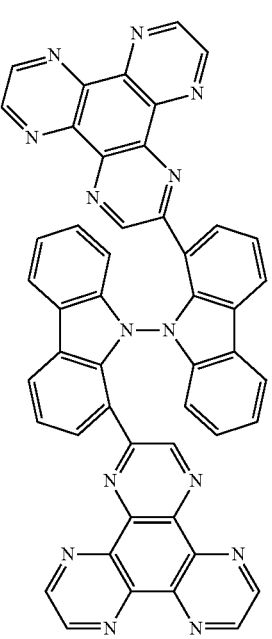
H07

103
-continued
H08
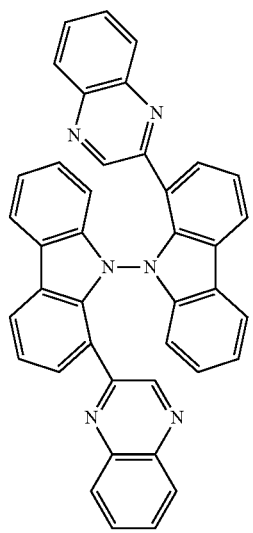
H09
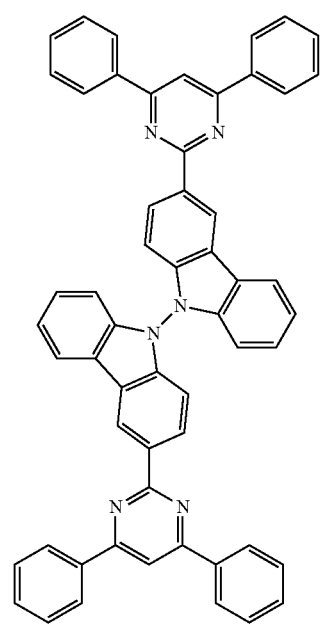
104
-continued
H10
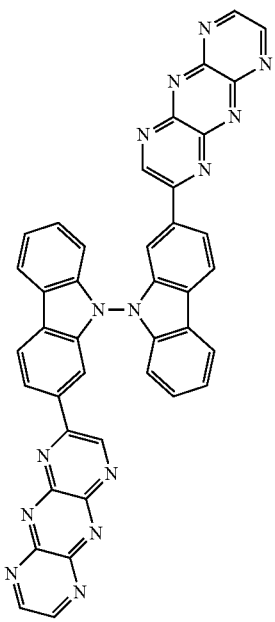
H11
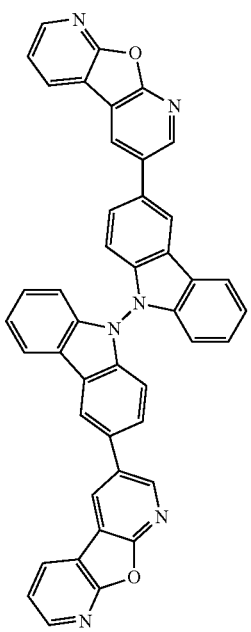

H12
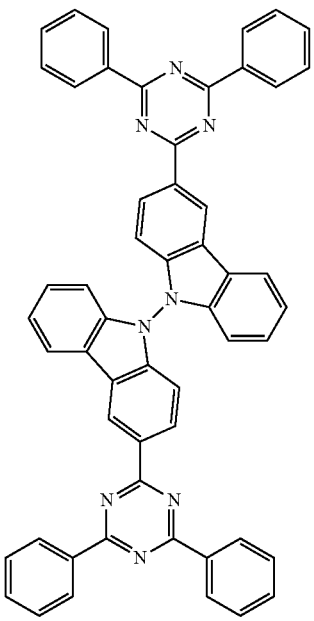
H13
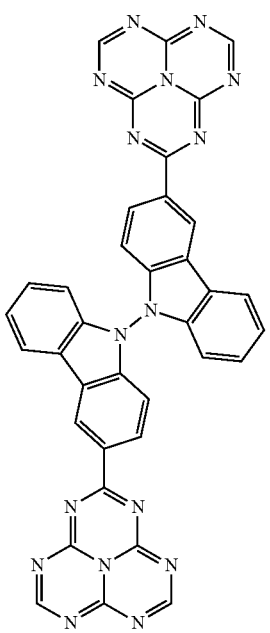
H14
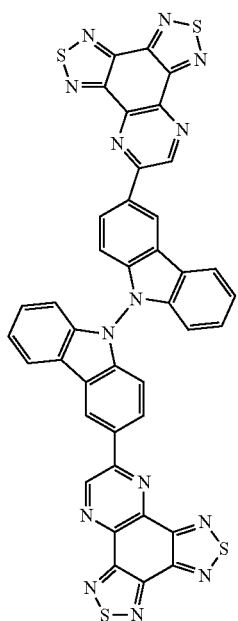
H15
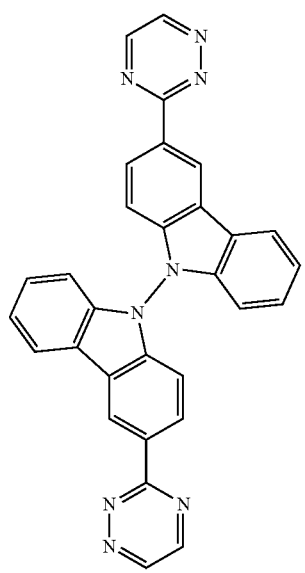

H16
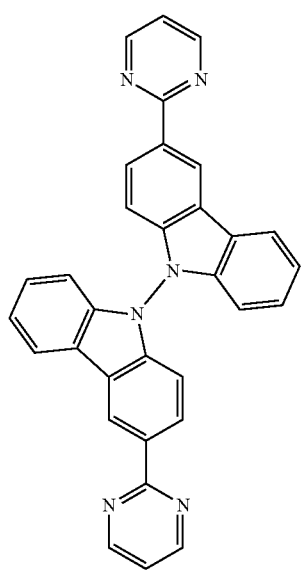
H17
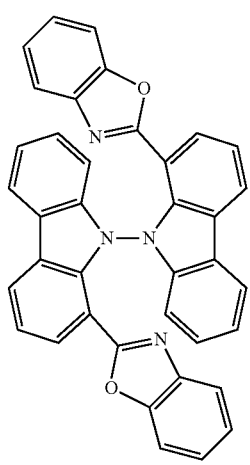
H18
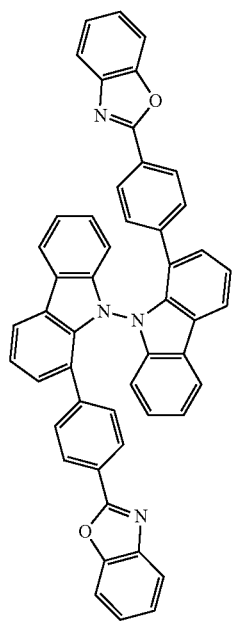
H19
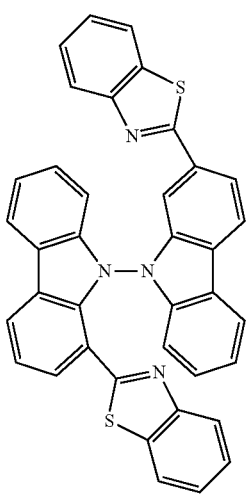
H20
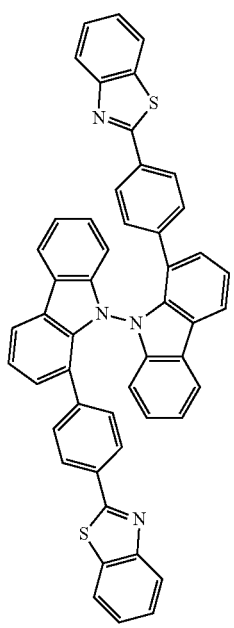

109
-continued
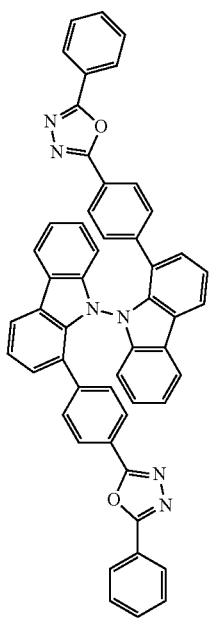
H21
110
-continued
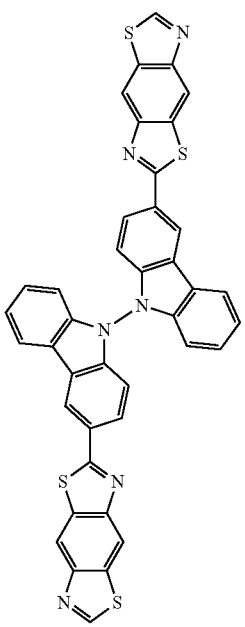
H23
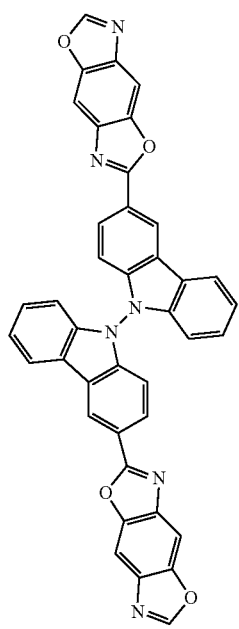
H22
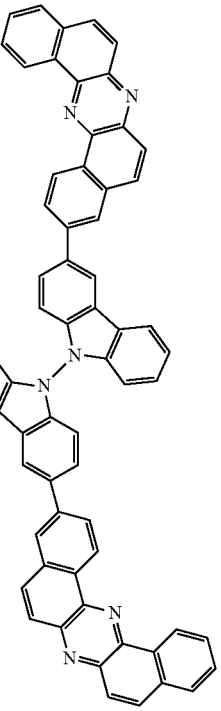
H24

111
-continued
112
-continued
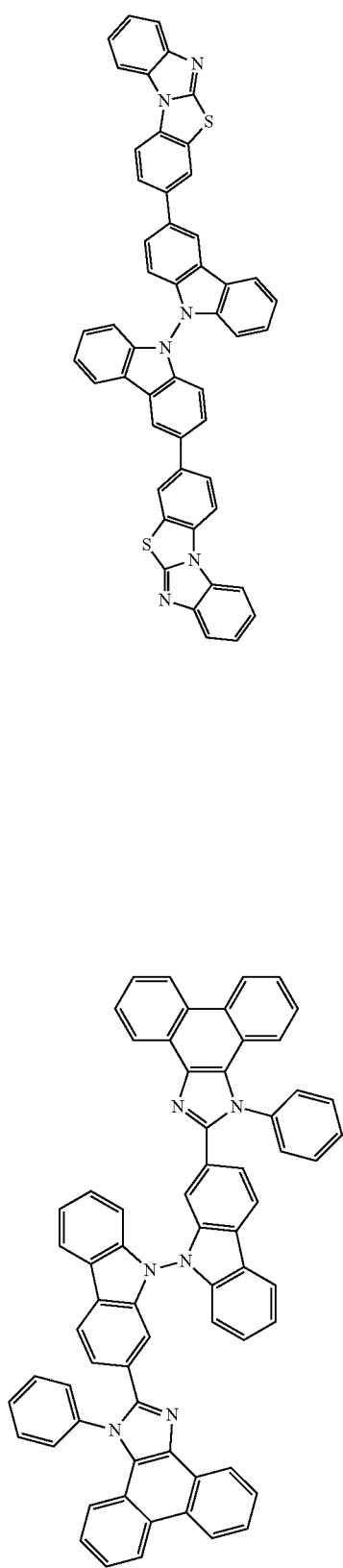
H25
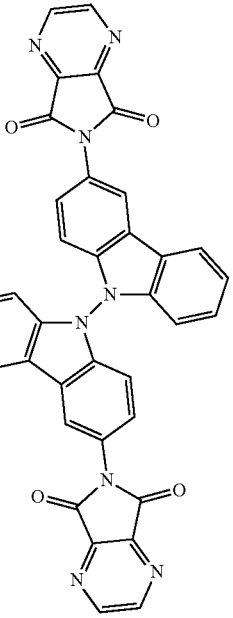
H27
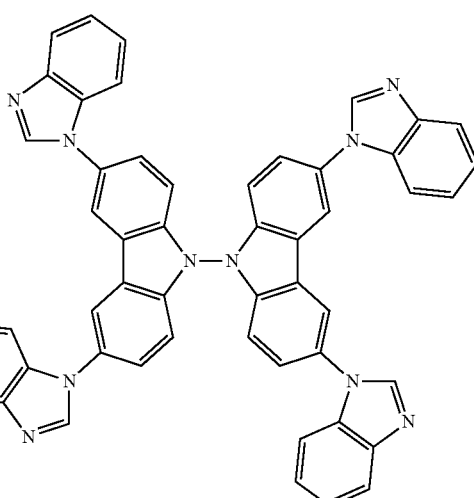
H28
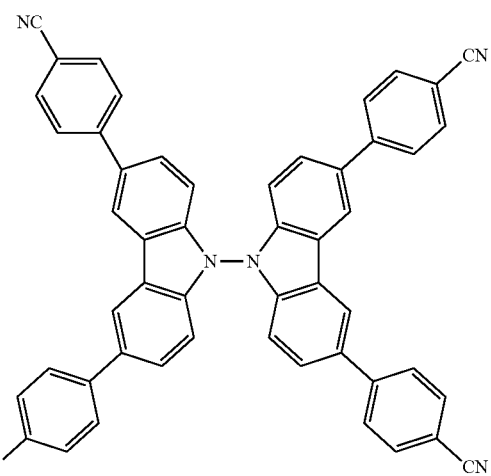
H29
H26

113
-continued
H30
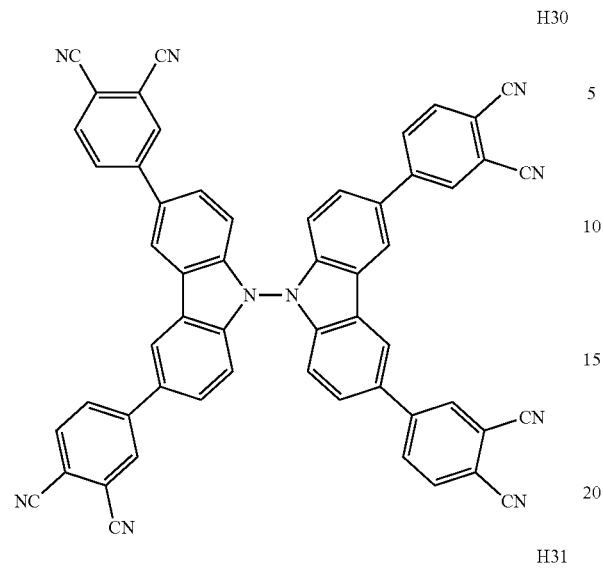
H31
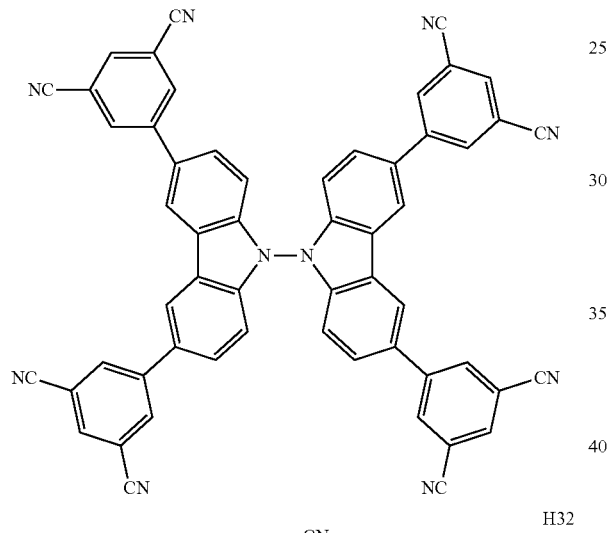
H32
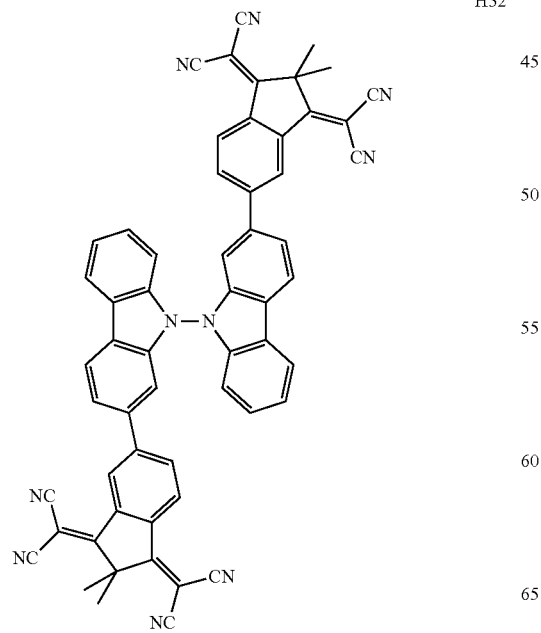
114
-continued
H33
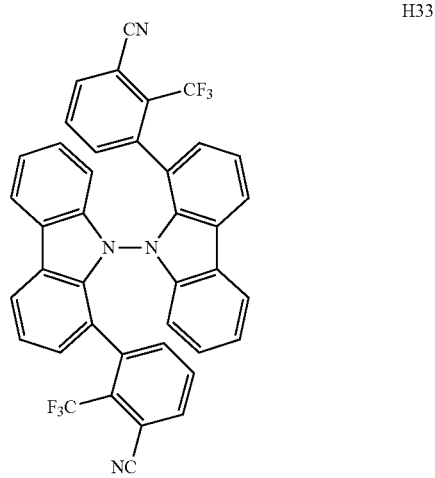
H34
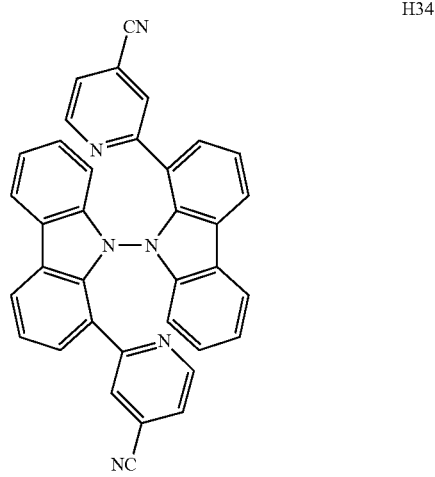
H35
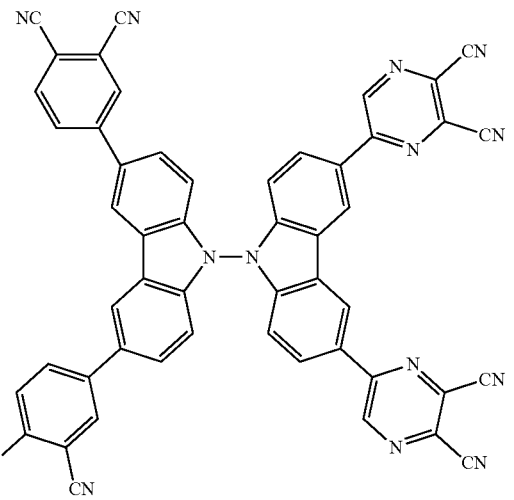

115 -continued
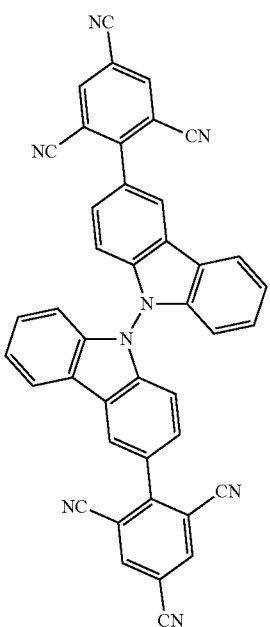
H36
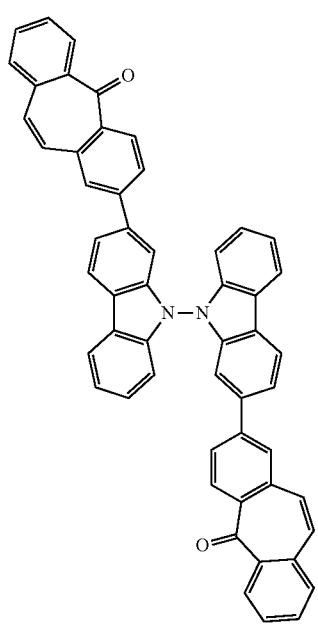
H37
116 -continued
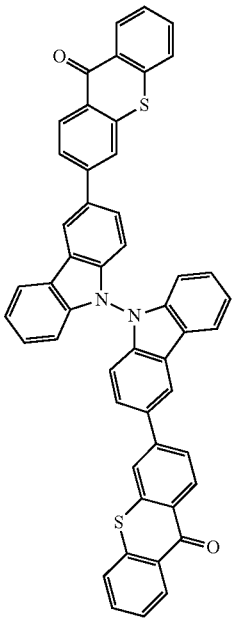
H38
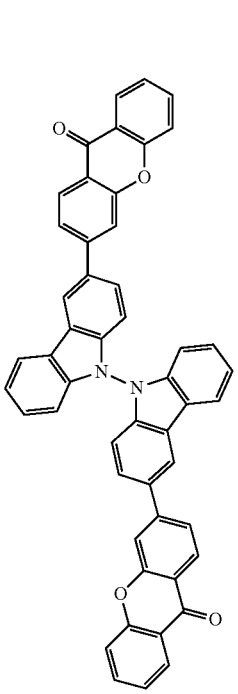
H39

H40
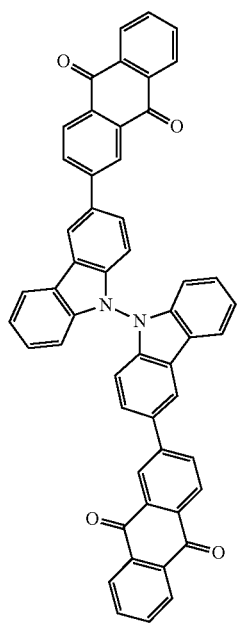
H41
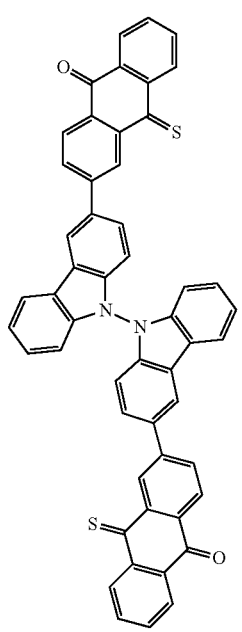
H42
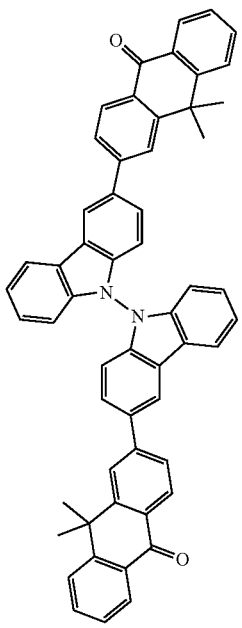
H43
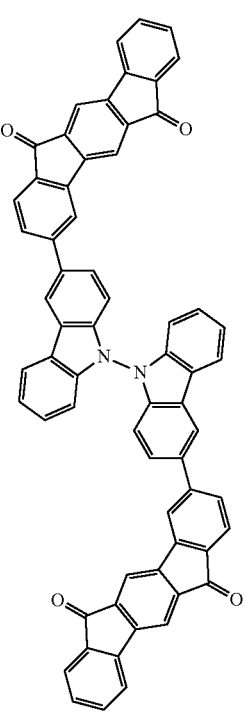

H44
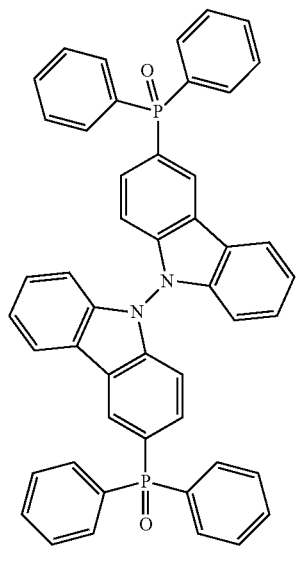
H45
H46
H47
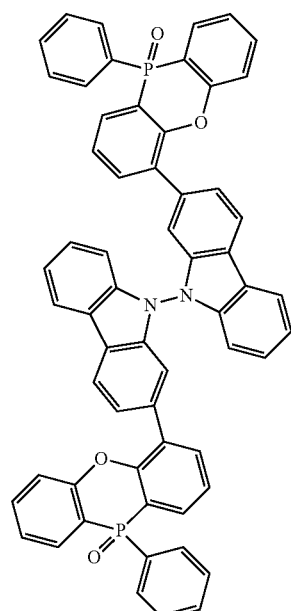
H48
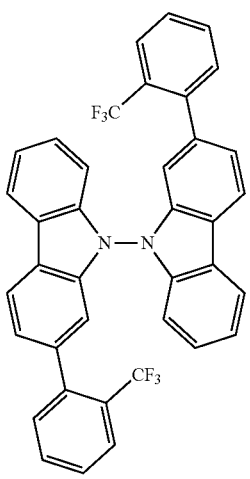

H49
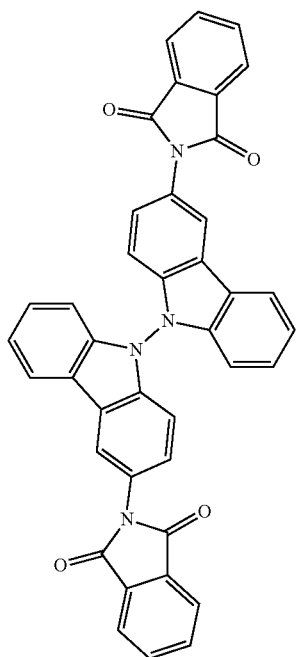
H50
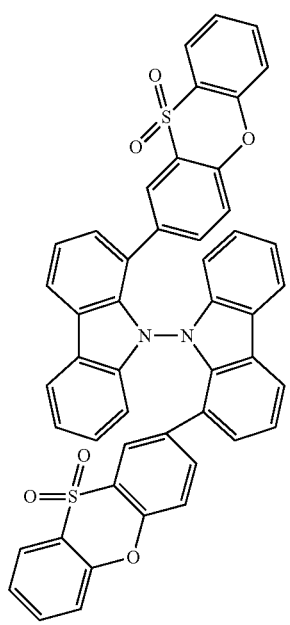
H51
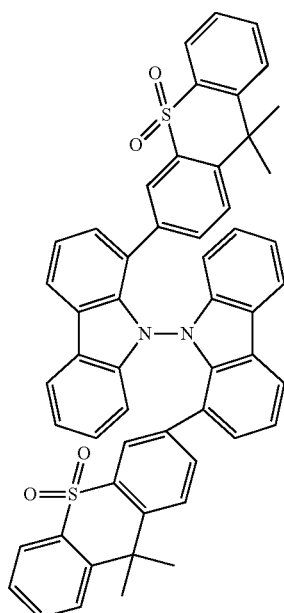
H52
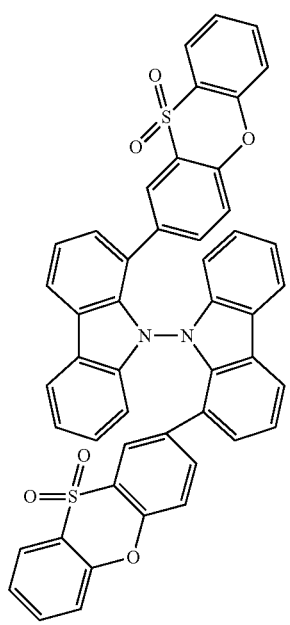

123
-continued
H53
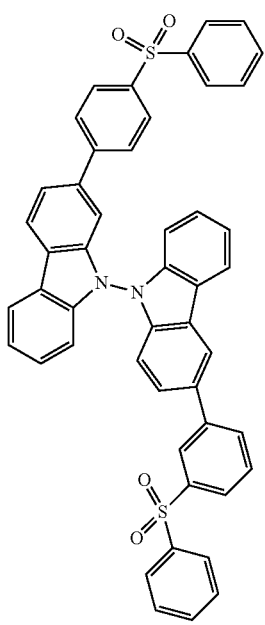
H54
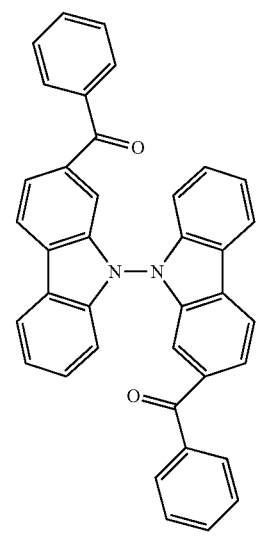
H55
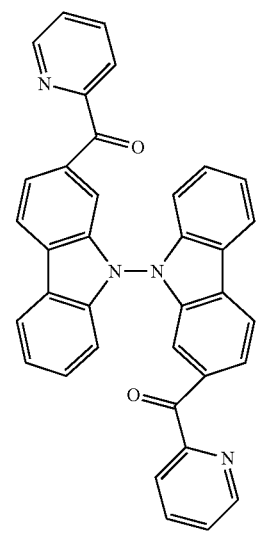
124
-continued
H56
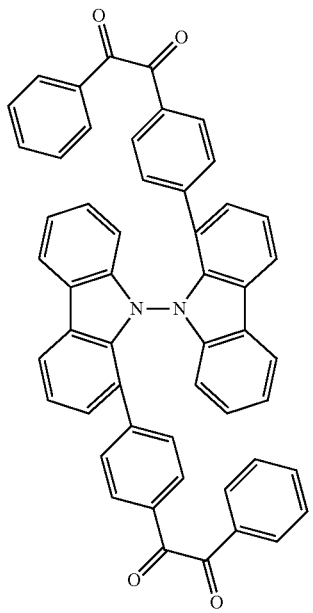
H57
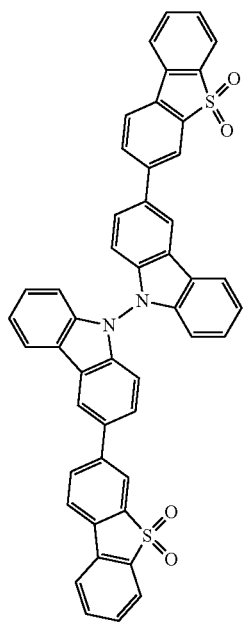

H58
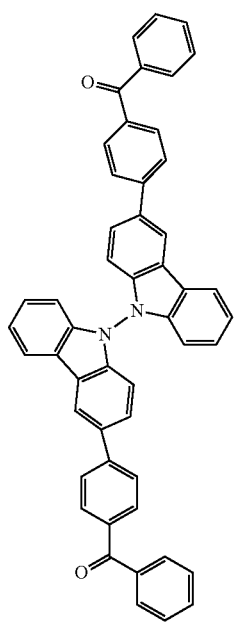
H59
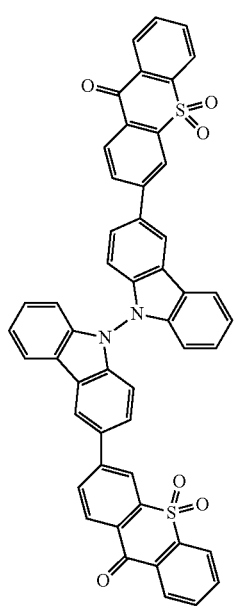
H60
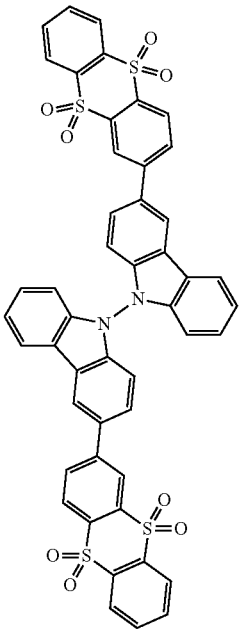
H61
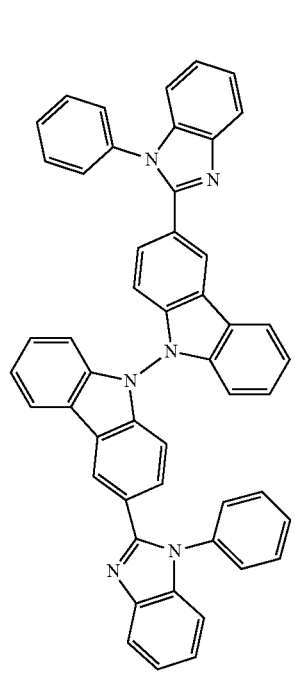

127
-continued
H62
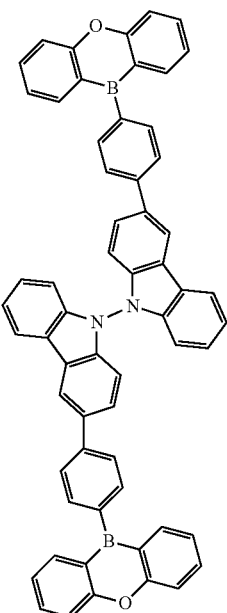
128
-continued
H64
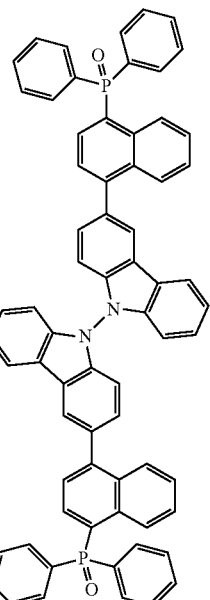
H63
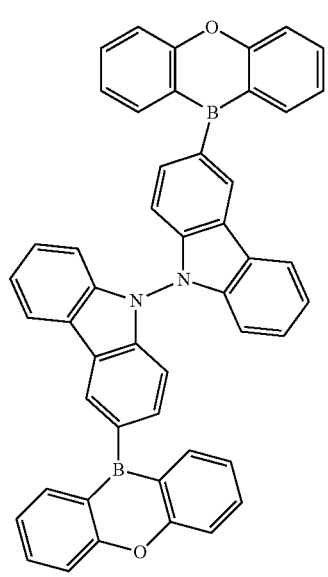
H65
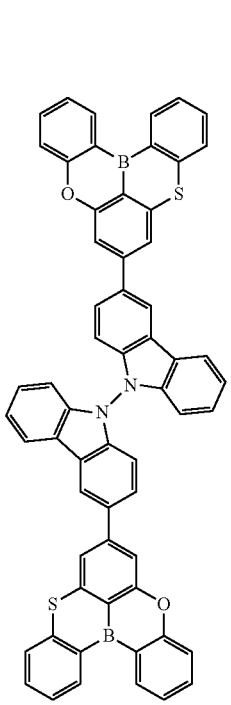

H66
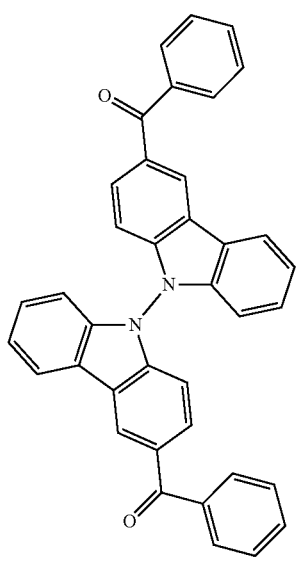
H68
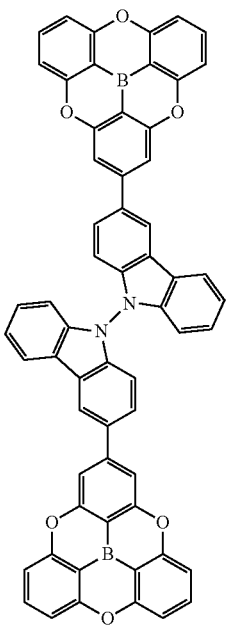
H67
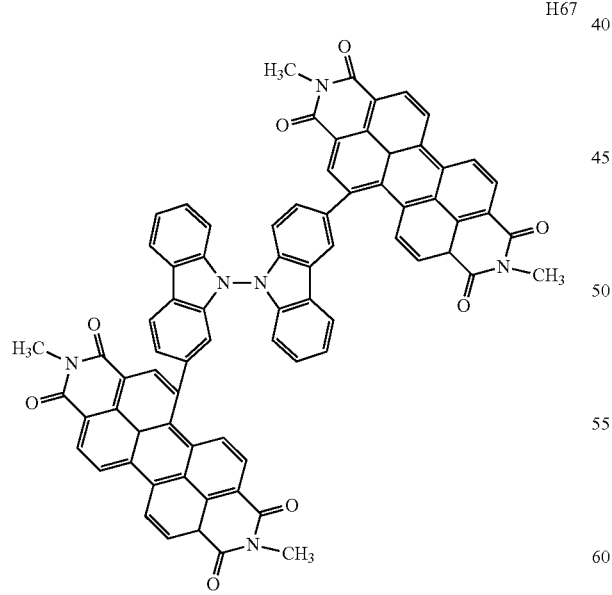
H69
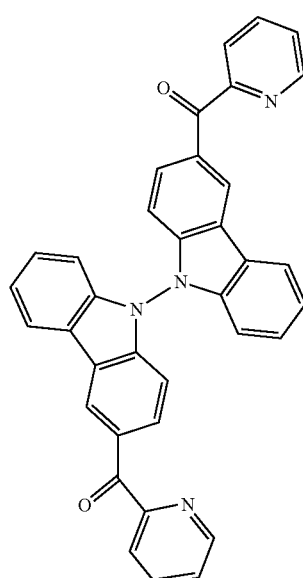

-continued
H70
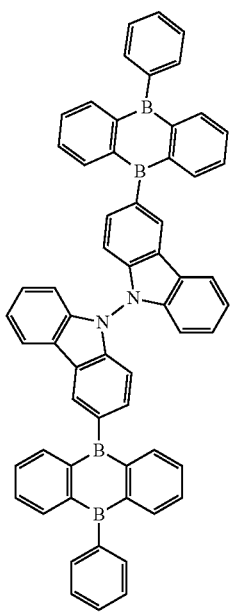
H71
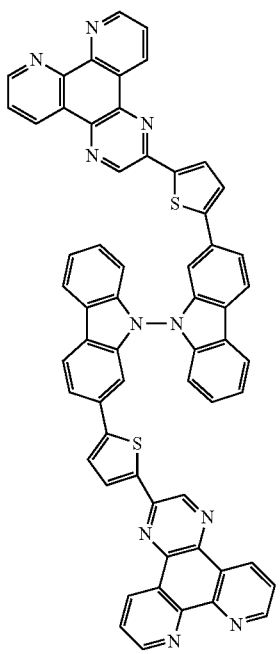
-continued
H72
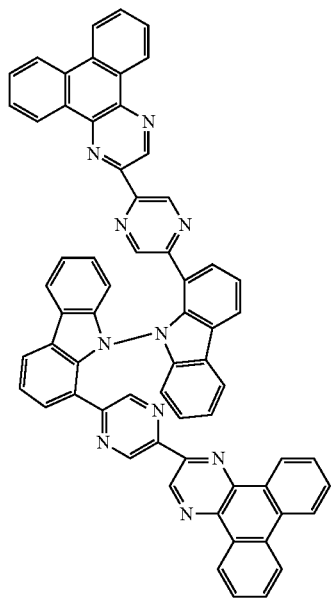
H73
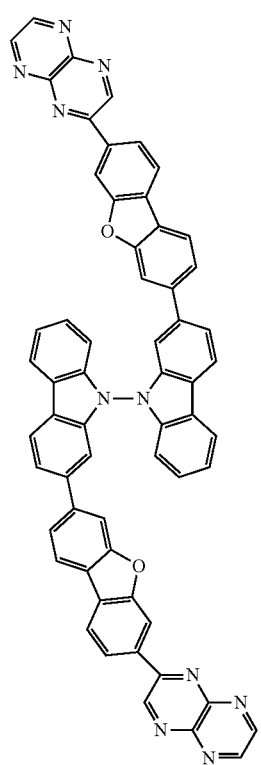

H74
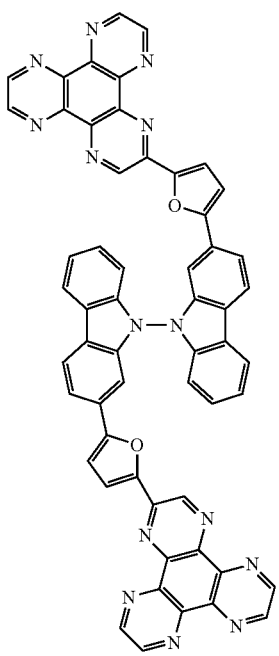
H75
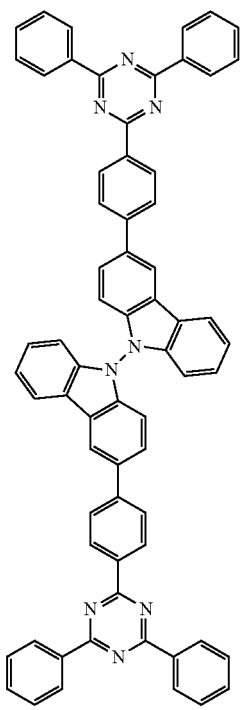
H76
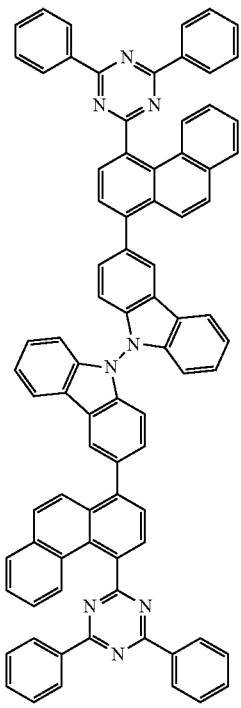
H77
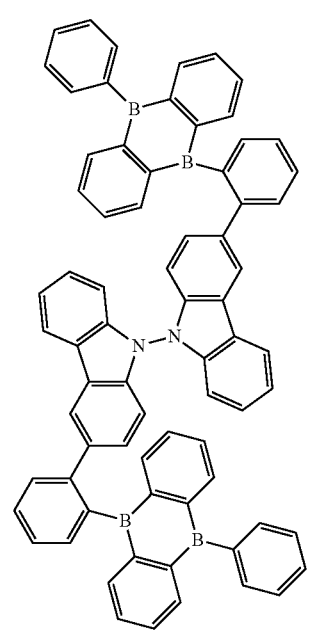

-continued

H78

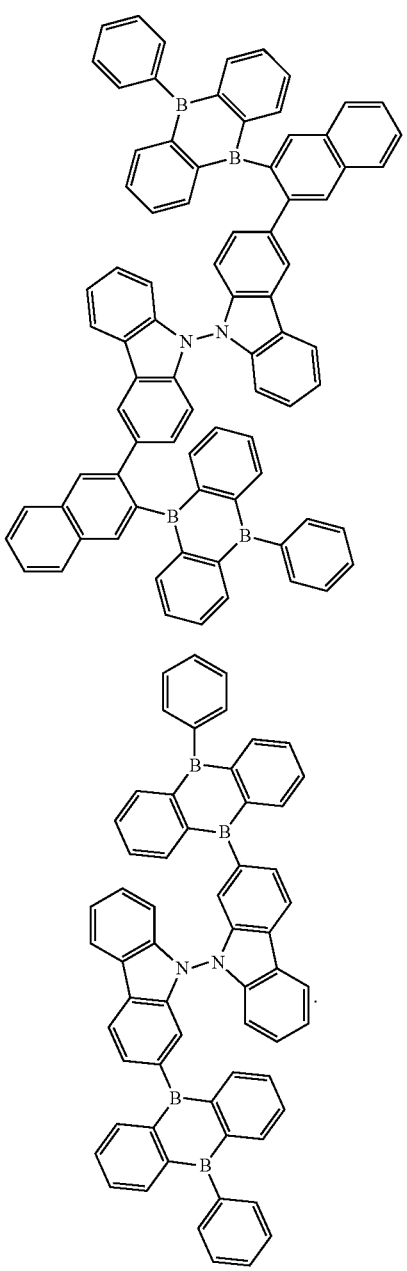

H79

17. An organic light emitting display device, wherein the organic light emitting display device comprises an organic electroluminescence apparatus, and the organic electroluminescence apparatus comprises:

an organic functional layer comprising one or more organic film layers, and at least one of the organic film layers is a luminescent layer; and the luminescent layer comprises a luminescent material, and the luminescent material comprises any one or more of the compounds according to claim 1;

wherein the compound is a host material of the luminescent layer.

18. The organic light emitting display device according to claim 17, wherein a guest material is selected from a fluorescent material, a thermally activated delayed fluorescent material, or a phosphorescence material, the difference between HOMO of the host material and HOMO of the guest material is less than 0.6 eV, or the difference between LUMO of the host material and LUMO of the guest material is less than 0.6 eV.

19. The organic light emitting display device according to claim 18, wherein the guest material is selected from a fluorescent material, or a thermally activated delayed fluorescent material, singlet-state energy of the guest material is lower than that of the host material, and difference between the singlet-state energy of the host material and the singlet-state energy of the guest material is less than 1.0 eV.

20. The organic light emitting display device according to claim 18, wherein the guest material is selected from a phosphorescence material, the triplet-state energy of the guest material is lower than that of the host material, and the difference between the triplet-state energy of the host material and the triplet-state energy of the guest material is less than 1.0 eV.

* * * * *